(12) United States Patent
Chen

(10) Patent No.: US 6,867,253 B1
(45) Date of Patent: Mar. 15, 2005

(54) TEAR RESISTANT, CRYSTALLINE MIDBLOCK COPOLYMER GELS AND ARTICLES

(75) Inventor: John Y. Chen, Pacifica, CA (US)

(73) Assignee: Applied Elastomerics, Inc., South San Francisco, CA (US)

( * ) Notice: Subject to any disclaimer, the term of this patent is extended or adjusted under 35 U.S.C. 154(b) by 269 days.

(21) Appl. No.: 09/721,213

(22) Filed: Nov. 21, 2000

Related U.S. Application Data

(63) Continuation-in-part of application No. 09/285,809, filed on Apr. 1, 1999, now abandoned, and a continuation-in-part of application No. 09/274,498, filed on Mar. 28, 1999, now Pat. No. 6,420,475, and a continuation-in-part of application No. 09/130,545, filed on Aug. 8, 1998, now Pat. No. 6,627,275, and a continuation-in-part of application No. 08/984,459, filed on Dec. 3, 1997, now Pat. No. 6,324,703, and a continuation-in-part of application No. PCT/US97/17534, filed on Sep. 30, 1997, and a continuation-in-part of application No. 08/909,487, filed on Jul. 12, 1997, now Pat. No. 6,050,871, and a continuation-in-part of application No. 08/863,794, filed on May 27, 1997, now Pat. No. 6,117,176, and a continuation-in-part of application No. 08/719,817, filed on Sep. 30, 1996, now Pat. No. 6,148,830, and a continuation-in-part of application No. 08/665,343, filed on Jun. 17, 1996, which is a continuation-in-part of application No. 08/612,586, filed on Mar. 8, 1996, now Pat. No. 6,552,109, and a continuation-in-part of application No. 08/581,191, filed on Dec. 29, 1995, now Pat. No. 5,760,117, and a continuation-in-part of application No. 08/581,188, filed on Dec. 29, 1995, now abandoned, and a continuation-in-part of application No. 08/581,125, filed on Dec. 29, 1995, now Pat. No. 5,962,572, and a continuation-in-part of application No. 08/288,690, filed on Aug. 11, 1994, now Pat. No. 5,633,286, and a continuation-in-part of application No. PCT/US94/07314, filed on Jun. 27, 1994, and a continuation-in-part of application No. PCT/US94/04278, filed on Apr. 19, 1994, said application No. 08/581,188, is a continuation-in-part of application No. 08/288,690, filed on Aug. 11, 1994, now Pat. No. 5,633,286, and a continuation-in-part of application No. PCT/US94/07314, filed on Jun. 27, 1994, and a continuation-in-part of application No. PCT/US94/04278, filed on Apr. 19, 1994, said application No. 08/581,191, is a continuation-in-part of application No. 08/288,690, and a continuation-in-part of application No. PCT/US94/07314, and a continuation-in-part of application No. PCT/US94/04278, said application No. 08/581,125, is a continuation-in-part of application No. 08/288,690, and a continuation-in-part of application No. PCT/US94/07314, filed on Jun. 27, 1994, and a continuation-in-part of application No. PCT/US94/04278.

(51) Int. Cl.$^7$ .......................... C08L 53/00; C08L 73/00
(52) U.S. Cl. ...................... 524/505; 524/507; 524/508; 524/513; 524/515; 623/59; 623/61; 623/63
(58) Field of Search ................................. 524/505, 507, 524/508, 513, 515; 623/59, 61, 63; 525/98

(56) References Cited

U.S. PATENT DOCUMENTS 5,459,193 A * 10/1995 Anderson et al. ........... 524/505

* cited by examiner

*Primary Examiner*—Robert D. Harlan

(57) ABSTRACT

Novel gels and articles are formed from one or more multiblock copolymers having at least one block segment of poly(ethylene) and selected amounts of one or more low viscosity plasticizers, said gels having an amount of crystallinity, glassy components, selected amounts of plasticizers, with or without other additives sufficient to achieve improvements in one or more physical properties including improved crack propagation resistance, improved tea resistance, improved resistance to fatigue and resistance to catastrophic failure not obtainable in amorphous gels and exceptionally lower and/or no tack.

17 Claims, 10 Drawing Sheets

| M1 | Fabric or Cloth |
|---|---|
| G | Gel |
| GM | Gel-Sponge or Gel-Foam |
| M2 | Foam or Sponge |
| M3 | Synthetic Resin or Plastic |
| M4 | Fibre |
| M5 | Concrete |
| M6 | Metal or Metal Sponge |
| M7 | Wood |
| M8 | Wire or Screening |
| M9 | Refractory Material |
| M10 | Other Material |

TEAR RESISTANT, CRYSTALLINE MIDBLOCK COPOLYMER GELS AND ARTICLES

ORIGINS OF INVENTION AND RELATED APPLICATIONS

This application is a continuation-in-part of the following applications: Ser. No. 09/285,809 filed Apr. 1, 1999 (now abandoned); Ser. No. 09/274,498, filed Mar. 28, 1999 (now U.S. Pat. No. 6,420,475); Ser. No. 09/130,545, filed Aug. 8, 1998 (now U.S. Pat. No. 6,627,275 B1); Ser. No. 08/984,459, filed Dec. 3, 1997 (now U.S. Pat. No. 6,324,703 B1); Ser. No. 08/909,487, filed Jul. 12, 1997 (now U.S. Pat. No. 6,050,871); Ser. No. 08/863,794, filed May 27, 1997 (now U.S. Pat. No. 6,117,176); PCT/US97/17534, filed 30 Sep. 1997; U.S. Ser. No: 08/719,817 filed Sep. 30, 1996 (now U.S. Pat. No. 6,148,830), U.S. Ser. No.: 08/665,343 filed Jun. 17, 1996 which is a Continuation-in-part of U.S. Ser. No.: 08/612,586 filed Mar. 8, 1996 (now U.S. Pat. No. 6,552,109); PCT/US94/04278 filed Apr. 19, 1994 (published May 26, 1995 No. WO95/13851) (now U.S. Pat. No. 6,033,283); PCT/US94/07314 filed Jun. 27, 1994 (published Jan. 4, 1996 No. WO 96/00118) (now U.S. Pat. No. 5,868,597); Ser. No. 08/288,690 filed Aug. 11, 1994 (now U.S. Pat. No. 5,633,286); Ser. No. 08/581,188 filed Dec. 29, 1995; Ser. No. 08/581,191 filed Dec. 29, 1995 (now U.S. Pat. No 5,760,117); Ser. No. 08/581,125 filed Dec. 29, 1995 (now U.S. Pat. No. 5,962,527). In turn U.S. Ser. Nos. 08/581,188; 08/581,191; and 08/581,125 are continuation-in-parts of the following applications: Ser. Nos.: 08/288,690; PCT/US94/07314 which is a CIP of PCT/US 94/04278. The subject matter contained in the related applications and patents are specifically incorporated herein by reference.

FIELD OF THE INVENTION

The present invention relates to gels and gel articles.

BACKGROUND OF THE INVENTION

This application is based upon subject matters described in earlier filed and copending related applications and patents (see Related Applications above).

A general view of oriented block copolymers is described in a publication by A. Weill and R. Pixa, in Journal of Polymer Science Symposium, 58,381–394 (1977), titled: "Styrene-diene Triblock Copolymers: Orientation Conditions and Mechanical Properties of the Oriented Materials" describe techniques of orientation of neat SIS and SBS block copolymers and their properties.

Other subject matters of interest are:

Elastomeric Thermoplastic, Vol. 5, pages 416–430, Block Copolymers, Vol. 2, pages 324; Block and Graft Copolymers; Styrene-Diene Block Copolymers, Vol. 15, pages 508–530; and Microphase Structure, can be found in *ENCYCLOPEDIA OF POLYMER SCIENCE AND ENGINEERING*, 1987.

Legge, N. R, et al., Chemistry and Technology of Block Polymers, Ch. 29, pages 394–429, ACS, Organic Coatings and Plastics Chemistry,© 1975.

Legge, N. R., Thermoplastic Elastomers, Rubber Chemistry and Technology, Vol. 60, pages G79–117.

Lindsay, G. A., et al., Morphology of Low Density Polyethylene/EPDM Blends Having Tensile Strength Synergism, source: unknown.

Cowie, J. M. G., et al., Effect of Casting on the Stress-Hardening and Stress-Softening Characteristics of Kraton-G 1650 Copolymer Films, J. Macromol. Sci.-Phys., B16(4), 611–632 (1979).

Futamura, S., et al., Effects of Center Block Structure on the Physical and Rheological Properties of ABA Block Copolymers. Part II. Rheological Properties, Polymer Engineering and Science, August, 1977, Vol. 17, No.8, pages 563–569.

Kururay Co., LTD. MSDS, Kuraray Septon 4055, Hydrogenated Styrene Isoprene/Butadiene Block Copolymer, Apr. 25, 1991.

SUMMARY OF THE INVENTION

The invention comprises gels and articles made from multiblock copolymers having two or more midblock polymer chains which gels exhibit advantages of improved tear propagation resistance. The gels also possess high tensile strength and rapid return from high extension and can exist in an altered state of delay elastomeric recovery as it regains its original shape following high extensions or dynamic deformations. Such combination of properties are not found in gels of substantially the same rigidity made from triblock copolymers. The gels of the present invention also exhibit low set, high dimensional stability, crack, tear, craze, and creep resistance, excellent tensile strength and high elongation, long service life under shear, stress and strain and capable of withstanding repeated dynamic shear, tear and stress forces, excellent processing ability for cast molding, extruding, fiber forming film forming and spinning, non-toxic, nearly tasteless and odorless, soft and strong, optically clear, highly flexible, possessing elastic memory, substantially with little or no plasticizer bleedout. The gels are especially suitable and have advantages where resistance to dynamic stretching, shearing and tearing forces are particularly critical such as those forces acting during dental flossing, while gels in the altered state with delay elastomeric recovery from deformation and extension are excellent for use where energy and vibration damping at high impact, low frequencies, such as in running shoe cushioning designs are essential.

Moreover, the gels can be made with selectively lower gel rigidities while achieving higher tensile strength or can be orientated to achieve high gel rigidities with lower gel tensile strengths.

Generally, the unique tear resistant gels comprises: (I) 100 parts by weight of one or more high viscosity linear multiblock copolymers or star-shaped (or radial) multiblock copolymers having two or more midblock segments or mixtures of two or more such copolymers; optionally in combination with a selected amount of one or more of a (II) polymer or copolymer, and selected amounts of one or more compatible plasticizing oils (III) sufficient to achieve gel rigidities of from less than about 2 gram Bloom to about 1,800 gram Bloom and higher.

The linear and star-shaped multiblock copolymers comprises one or more poly(ethylene) segment containing copolymer(s) which can exhibit crystallinity with glassy end block ($A^n$) of a monoalkenyl arene compounds, more specifically, a monovinyl aromatic compounds, and midblocks (Z) comprising two or more segment polymer chains of poly(ethylene), poly(butylene), poly(propylene), poly(ethylene-butylene), and poly(ethylene-propylene).

The (I) linear copolymers are characterized as having a Brookfield Viscosity cP(mPa•S) value at 5 weight percent solids solution in toluene at 30° C. of from less than about 40 cps to about 150 cps and higher, advantageously from about 40 cps to about 60 cps and higher, more advantageously from about 50 cps to about 80 cps and higher, still more advantageously from about 70 cps to about 110 cps and higher, and even more advantageously from about 90 cps to about 180 cps and higher.

The (I) star-shaped copolymers are characterized as having a Brookfield Viscosity cP(mPa•S) value at 5 weight percent solids solution in toluene at 30° C. of from about 150 cps to about 380 cps and higher, advantageously from about 150 cps to about 260 cps and higher, more advantageously from about 200 cps to about 580 cps and higher, and still more advantageously from about 500 cps to about 1,000 cps and higher.

As used herein, the term "gel rigidity" in gram Bloom is determined by the gram weight required to depress a gel a distance of 4 mm with a piston having a cross-sectional area of 1 square centimeter at 23° C.

As described herein, the conventional term "major" means about 51 weight percent and higher (e.g. 55%, 60%, 65%, 70%, 75%, 80% and the like) and the term "minor" means 49 weight percent and lower (e.g. 2%, 5%, 10%, 15%, 20%, 25% and the like).

The various aspects and advantages will become apparent to those skilled in the art upon consideration of the accompanying disclosure.

DESCRIPTION OF THE DRAWINGS

FIG. 1. Representative components materials of composites forming useful articles of the invention.

DESCRIPTION OF THE INVENTION

Figure 2A:
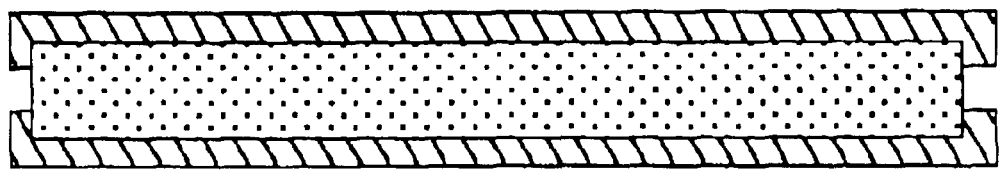
FIG. 2. Representative sectional view of composite articles of the invention (FIG. 2a.=MGM, FIG. 2b.=GMG, FIG. 2c.=MGMGMGM, FIG. 2d.=foam entirely interlocked with composition).

Thermoplastic elastomer gels are described in my patents and published applications: PCT/US97/17534; PCT/US94/04278; PCT/US94/07314; U.S. Pat. Nos. 5,884,639; 5,868, 597; 5,760,117; 5,655,947; 5,624,294; 5,508,334; 5,475, 890; 5,336,708; 5,324,222; 5,262,468; 5,239,723; 5,153, 254; 4,618,213; and 4,369,284. Various patents on thermoplastic elastomers and blends are described in U.S. Pat. Nos. 5,755,243; 3,595,942, Reissue 27,145-28,236; 3,772,234; 4,116,917; 4,687,815; and 4,880,878. Other non-patent publications related to S-EB-S polymers include: (1) W. P. Gergen, "Uniqueness of Hydrogenated Block Copolymers for Elastomeric Applications," presented at the German Rubber Meeting, Wiesbaden, 1983; Kautsch, Gummi, Kunstst. 37, 284 (1984). (2) W. P. Gergen, et al., "Hydrogenated Block Copolymers," Paper No. 57, presented at a meeting of the Rubber Division ACS, Los Angeles, Apr. 25, 1985. Encyclopedia of Polymer Science and Engineering, Vol. 2, pp 324–434, "Block Copolymers". (3) L. Zotteri and et al., "Effect of hydrogenation on the elastic properties of poly(styrene-b-diene-b-styrene) copolymers", Polymer, 1978, Vol. 19, April. (4) J. Kenneth Craver, et al., Applied Polymer Science, Ch. 29, "Chemistry and Technology of Block Polymers", pp. 394–429, 1975. (5) Y. Mahajer and et al., "The influence of Molecular Geometry on the Mechanical Properties of homopolymers and Block Polymers of Hydrogenated Butadiene and Isoprene" reported under U.S. ARO Grant No. DAAG29-78-G0201. (6) J. E. McGrath, et al., "Linear and Star Branched Butadiene-Isoprene Block Copolymers and Their Hydrogenated Derivatives", Chem. Dept, Virginia Polytechnic Institute and State University Blacksturg, Va., reported work supported by Army Research Office. (7) Legge, Norman R., "Thermoplastic Elastomers", Charles Goodyear Medal address given at the 131st Meeting of the Rubber Division, American Chemical Society, Montreal, Quebec, Canada, Vol. 60, G79–G115, May 26–29, 1987. (8) Falk, John Carl, and et al., "Synthesis and Properties of Ethylene-Butylene-1 Block Copolymers", Macromolecules, Vol. 4, No. 2, pp. 152–154, March–April 1971. (9) Morton, Maurice, and et al., "Elastomeric Polydiene ABA Triblock Copolymers within Crystalline End Blocks", University of Arkon, work supported by Grant No. DMR78-09024 from the National Science Foundation and Shell Development Co. (10) Yee, A. F., and et al., "Modification of PS by S-EB-S Block Copolymers: Effect of Block Length", General Electric Corporate Research & Development, Schenectady, N.Y. 12301. (11) Siegfried, D. L, and et al., "Thermoplastic Interpenetrating Polymer Networks of a Triblock Copolymer elastomer and an Ionomeric Plastic Mechanical Behavior", Polymer Engineering and Science, January 1981, Vol. 21, No.1, pp 39–46. (12) Clair, D. J., "S-EB-S Copolymers Exhibit Improved Wax Compatibility", Adhesives Age, November, 1988. (13) Shell Chemical Technical Bulletin SC:1102–89, "Kraton® Thermoplastic Rubbers in oil gels", April 1989. (14) Chung P. Park and George P. Clingerman, "Compatibilization of Polyethylene-Polystyrene Blends with Ethylene-Styrene Random Copolymers", the Dow Chemical Company, May 1996. (15) Steve Hoenig, Bob Turley and Bill Van Volkenburgh, "Material Properties and Applications of Ethylene-Styrene Interpolymers", the Dow Chemical Company, September 1996. (16) Y. Wilson Cheung and Martin J. Guest, "Structure, Thermal Transitions and Mechanical Properties of Ethylene/Styrene Copolymers", the Dow Chemical Company, May 1996. (17) Teresa Plumley Karjaia, Y. Wilson Cheung and Martin J. Guest, "Melt Rheology and Processability of Ethylene/Styrene Interpolymers", the Dow Chemical Company, May 1997. (18) D. C. Prevorsek, et al., "Origins of Damage Tolerance in Ultrastrong Polyethylene Fibers and Composites:, Journal of Polymer Science: Polymer Symposia No. 75, 81–104

(1993). (19) Chen, H., et al, "Classification of Ethylene-Styrene Interpolymers Based on Comonomer Content", J. Appl. Polym. Sci., 1998,70, 109. (20–24) U.S. Pat. Nos. 5,872,201; 5,460,818; 5,244,996; EP 415815A; JP07,278, 230 describes substantially random, more appropriately presudo-random copolymers (interpolymers), methods of making and their uses. (25) Alizadeh, et al., "Effect of Topological Constraints on The Crystallization Behavior of Ethylene/alp[ha-Olefin Copolymers", PMSE, Vol, 81, pp. 248–249, Aug. 22–26, 1999. (26) Guest, et al., "Structure/ Property Relationships of Semi-Crystalline Ethylene-Styrene Interpolymers (ESI)", PMSE, Vol, 81, pp. 371–372, Aug. 22–26, 1999. The above applications, patents and publications are specifically incorporated herein by reference.

Legge's paper teaches the development of (conventional substantially amorphous elastomer mid segment) SEBS triblock copolymers. In the polymerization of butadiene by alkyllithium initiators, 1,4-addition or 1,2-addition polymers, mixtures, can be obtained. In forming styrene butadiene triblock copolymers involving the addition of solvating agents such as ethers just before the final styrene charge is added, any excess of ethers can alter the polybutadiene structure from a 1,4-cis or trans structure to a 1,2- or 3,4-addition polymer. Using difunctional coupling agent would give linear block copolymers and multifuntional agents would give star-shaped or radial block copolymers. Hydrogenation of the 1,4-polybutadiene structure yields polyethylene, while that of the 1,2-polybutadiene yields polybutylene. The resulting polyethylene will be essentially identical with linear, high-density polyethylene with a melting point, Tm, of about 136° C. Hydrogenation of 1,2-polybutadiene would yield atactic poly(1-butene) (polybutylene). The Tg of polybutylene is around −18° C. Random mixtures of ethylene and butylene units in the chain would suppress crystallinity arising from polyethylene sequences. The objective for a good elastomer should be to obtain a saturated olefin elastomeric segment with the lowest possible Tg and the best elastomeric properties. Such an elastomer favored using styrene as the hard-block monomer and selecting the best monomer for hydrogenation of the elastomer mid segment Using a mixture of 1,4- and 1,2-polybutadiene as the base polymer for the mid segment would result in an ethylene/butylene mid segment in the final product. The elements of selection of the midsegment composition is elastomer crystallinity and the elastomer Tg of an ethylene/butylene copolymer. Very low levels of crystallinity can be achieved around 40–50% butylene concentration. The minimum in dynamic hysteresis around 35% butylene concentration in the elastomeric copolymer. A value of 40% butylene concentration in the ethylene/butylene midsegment was chosen for the S-EB-S block copolymers.

Clair's paper teaches that the EB midblock of conventional S-EB-S polymers is a random copolymer of ethylene and 1-butene exhibiting nearly no crystallinity in the midblock. In the preparation of ethylene-butylene (EB) copolymers, the relative proportions of ethylene and butylene in the EB copolymer chain can be controlled over a broad range from almost all ethylene to almost all butylene. When the EB copolymer is nearly all ethylene, the methylene sequences will crystallize exhibiting properties similar to low density polyethylene. In differential scanning calorimeter (DSC) curves, the melting endotherm is seen on heating and a sharp crystallization exotherm is seen on cooling. As the amount of butylene in the EB copolymer is increased, the methylene sequences are interrupted by the ethyl side chains which shorten the methylene sequences length so as to reduce the amount of crystallinity in the EB copolymer. In conventional S-EB-S polymers, the amount of 1-butene is controlled at a high enough level to make the EB copolymer midblock almost totally amorphous so as to make the copolymer rubbery and soluble in hydrocarbon solvents. Clair suggests that an S-EB-S polymer retaining at least some crystallinity in the EB copolymer midblock may be desirable. Therefore, a new family of S-EB-S polymers are developed (U.S. Pat. No. 3,772,234) in which the midblock contains a higher percentage of ethylene. The molecular weights of the new crystalline midblock segment S-EB-S polymers can vary from low molecular weight, intermediate molecular, to high molecular weight; these are designated Shell GR-3, GR-1, and GR-2 respectively. Unexpectly, the highest molecular weight polymer, GR-2 exhibits an anomalously low softening point. A broad melting endotherm is seen in the DSC curves of these polymers. The maximum in this broad endotherm occurs at about 40° C.

Himes, et al., (U.S. Pat. No. 4,880,878) describes SEBS blends with improved resistance to oil absorption.

Papers (14)–(17) describes poly(ethylene-styrene) substantially random copolymers (Dow Interpolymers™): Dow S, M and E Series produced by metallocene catalysts, using single site, constrained geometry addition polymerization catalysts resulting in poly(ethylene-styrene) substantially random copolymers with weight average molecular weight (Mw) typically in the range of $1 \times 10^5$ to $4 \times 10^5$, and molecular weight distributions (Mw/Mn) in the range of 2 to 5.

Paper (18) Prevorsek, et al., using Raman spectroscopy, WAXS, SAXD, and EM analysis interprets damage tolerance of ultrastrong PE fibers attributed to the nano scale composite structure that consists of needle-like-nearly perfect crystals that are covalently bonded to a rubbery matrix with a structure remarkably similar to the structure of NACRE of abalone shells which explains the damage tolerance and impact resistance of PE fibers. PE because of its unique small repeating unit, chain flexibility, ability to undergo solid state transformation of the crystalline phase without breaking primary bonds, and its low glass transition temperature which are responsible for large strain rate effects plays a key role in the damage tolerance and fatigue resistance of structures made of PE fibers.

Figure 2B:
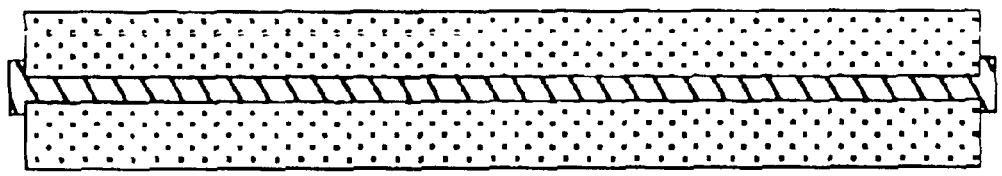
Figure 2C:
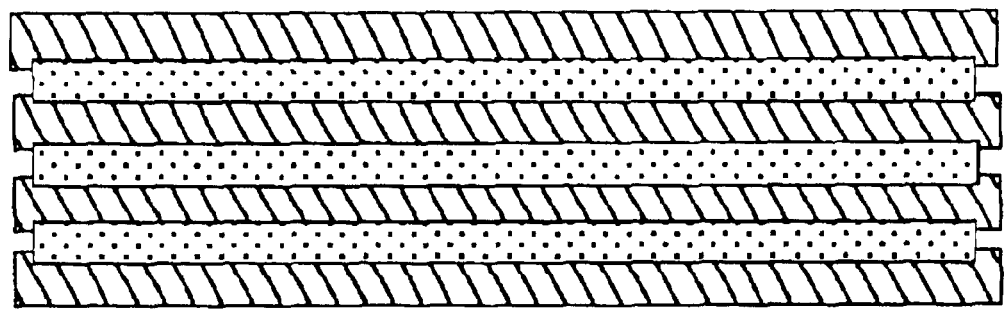
Figure 2D:
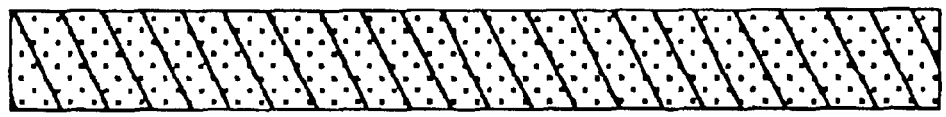
Figure 3A:
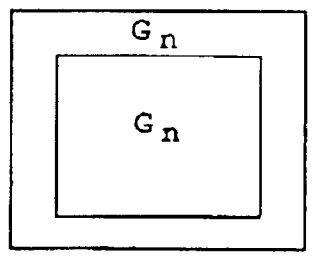
FIGS. 3a–3n. Representative sectional view of composite articles as shown generally by the relationship of $G_n$ and $M_n$ and more specific article examples of $M_1$, $M_2$, $M_3$, and $M_4$ with $G_n$ when the material $M_n$ is n=1 (fabric/cloth), n=2 (foam/sponge), n=3 (synthetic resin/plastic), and n=4 (fibre) as shown in FIGS. 3d, 3e, 3h, and 3j respectively.
Figure 3B:
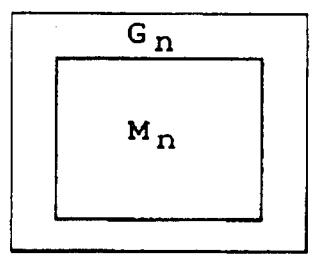
Figure 3C:
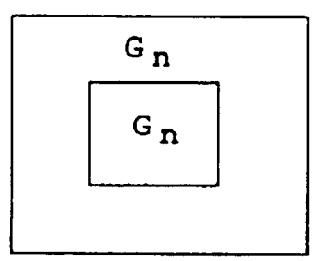
Figure 3D:
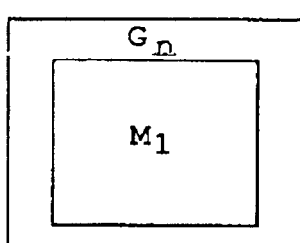
Figure 3E:
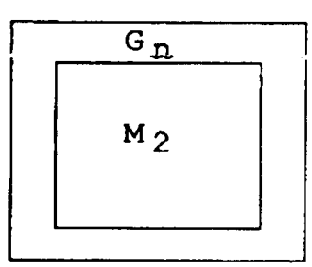
Figure 3F:
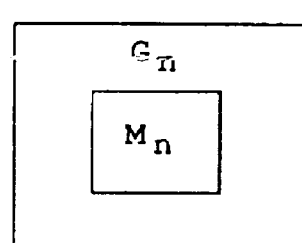
Figure 3G:
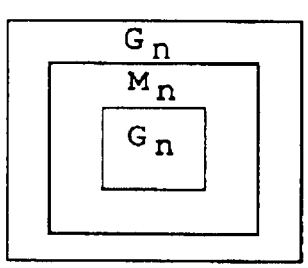
Figure 3H:
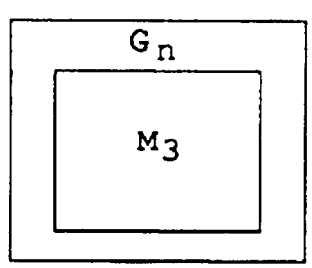
Figure 3I:
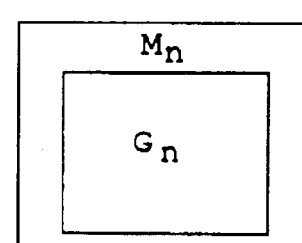
Figure 3J:
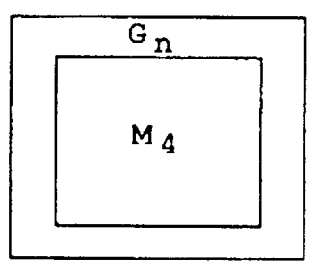
Figure 3K:
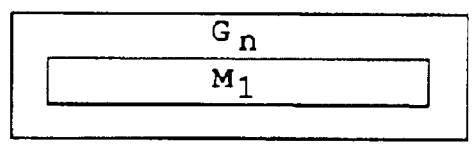
Figure 3L:
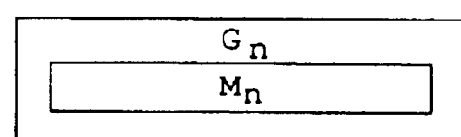
Figure 3M:
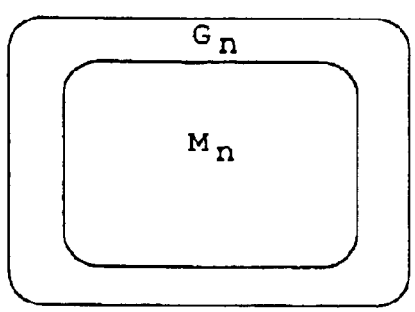
Figure 3N:
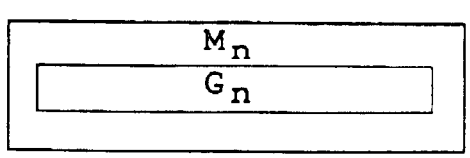
Figure 4A:
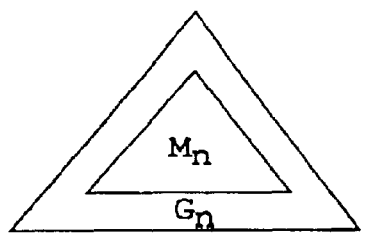
FIGS. 4a–4w. Representative sectional view of composite articles as shown generally by the relationship of $G_n$ and $M_n$ and more specific article examples of $M_1$, $M_2$, $M_3$, and $M_4$ with $G_n$ when the material $M_n$ is n=1 (fabric/cloth), n=2 (foam/sponge), n=3 (synthetic resin/plastic), and n=4 (fibre) as shown in FIGS. 4l, 4m, 4n, and 4q respectively.
Figure 4B:
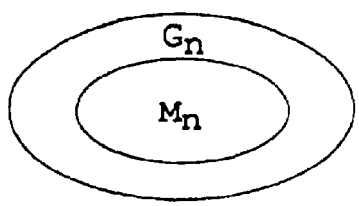
Figure 4C:
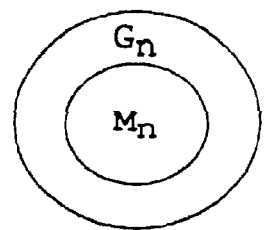
Figure 4D:
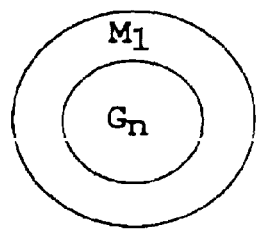
Figure 4E:
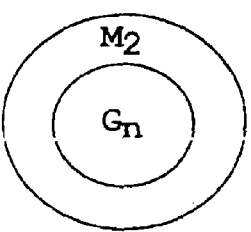
Figure 4F:
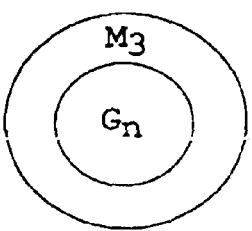
Figure 4G:
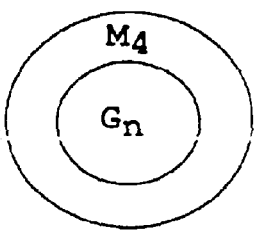
Figure 4H:
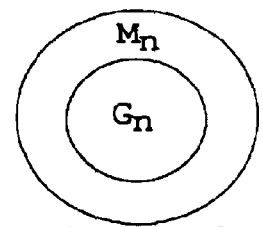
Figure 4I:
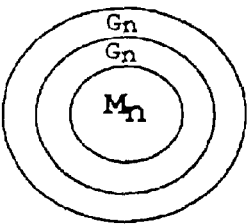
Figure 4J:
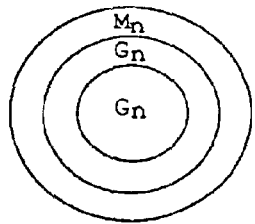
Figure 4K:
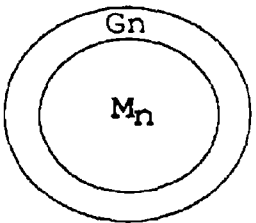
Figure 4L:
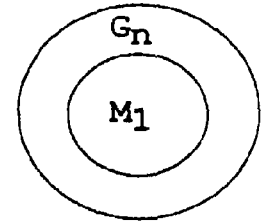
Figure 4M:
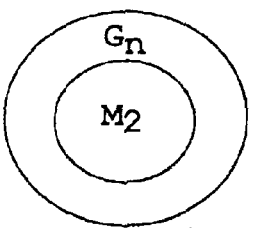
Figure 4N:
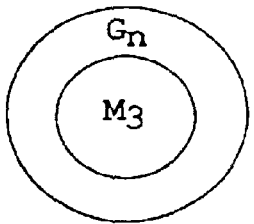
Figure 4O:
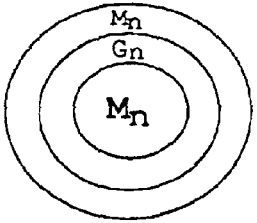
Figure 4P:
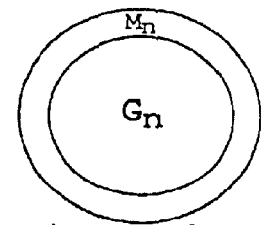
Figure 4Q:
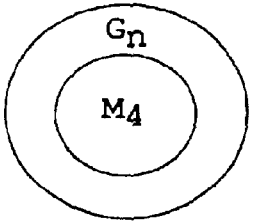
Figure 4R:
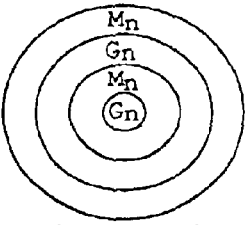
Figure 4S:
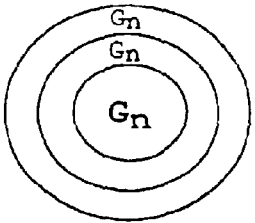
Figure 4T:
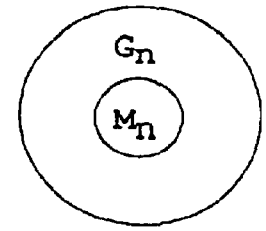
Figure 4U:
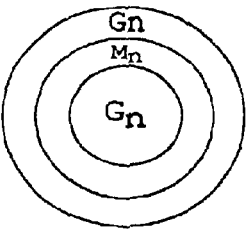
Figure 4V:
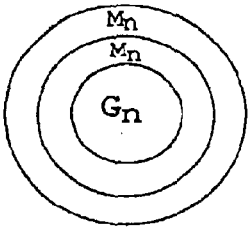
Figure 4W:
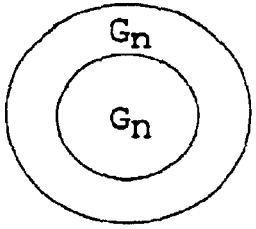
Figure 5:
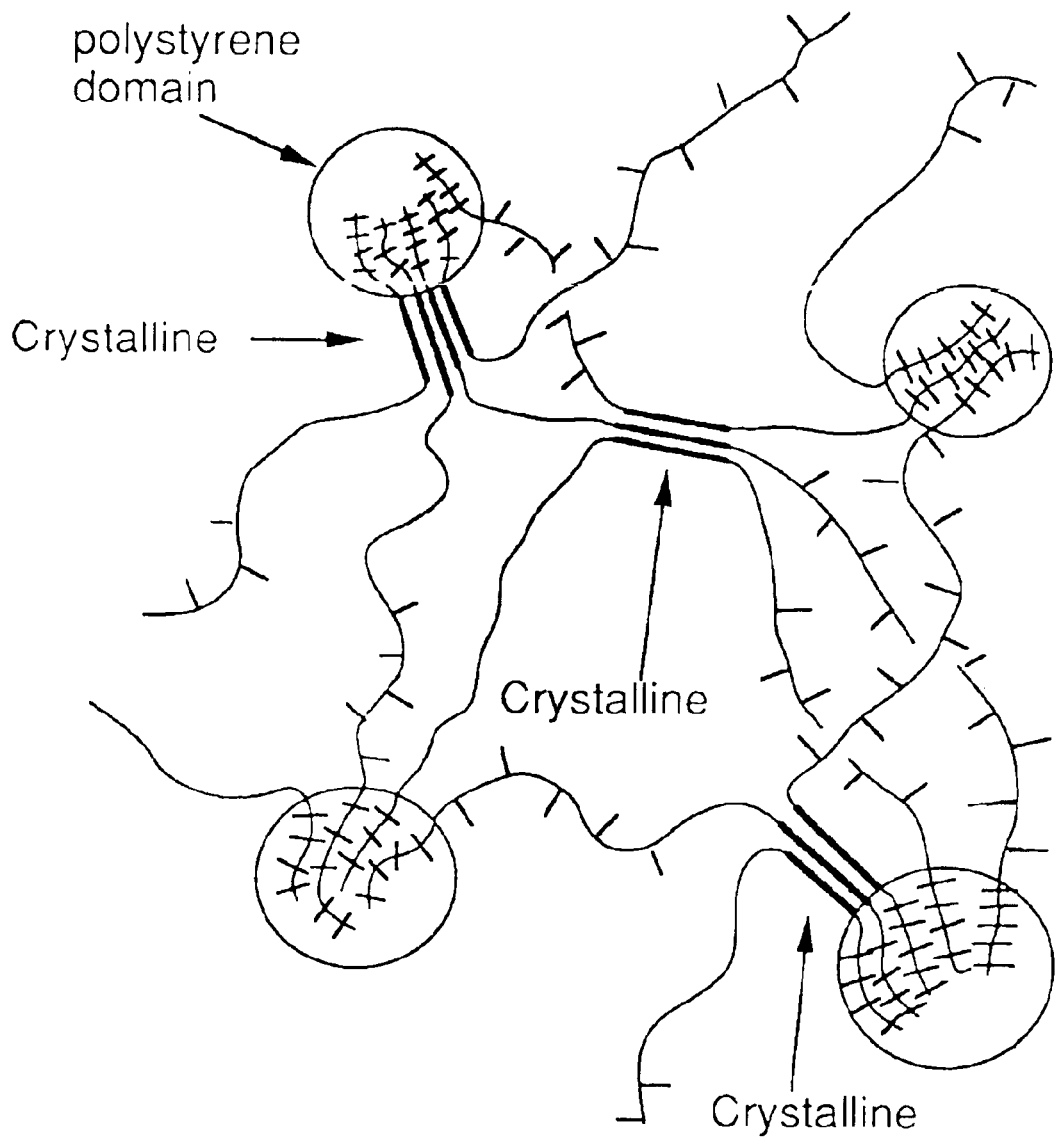
FIG. 5. Representation of S-E-EP-S crystalline polystyrene domain/amorphous structure.
Figure 6:
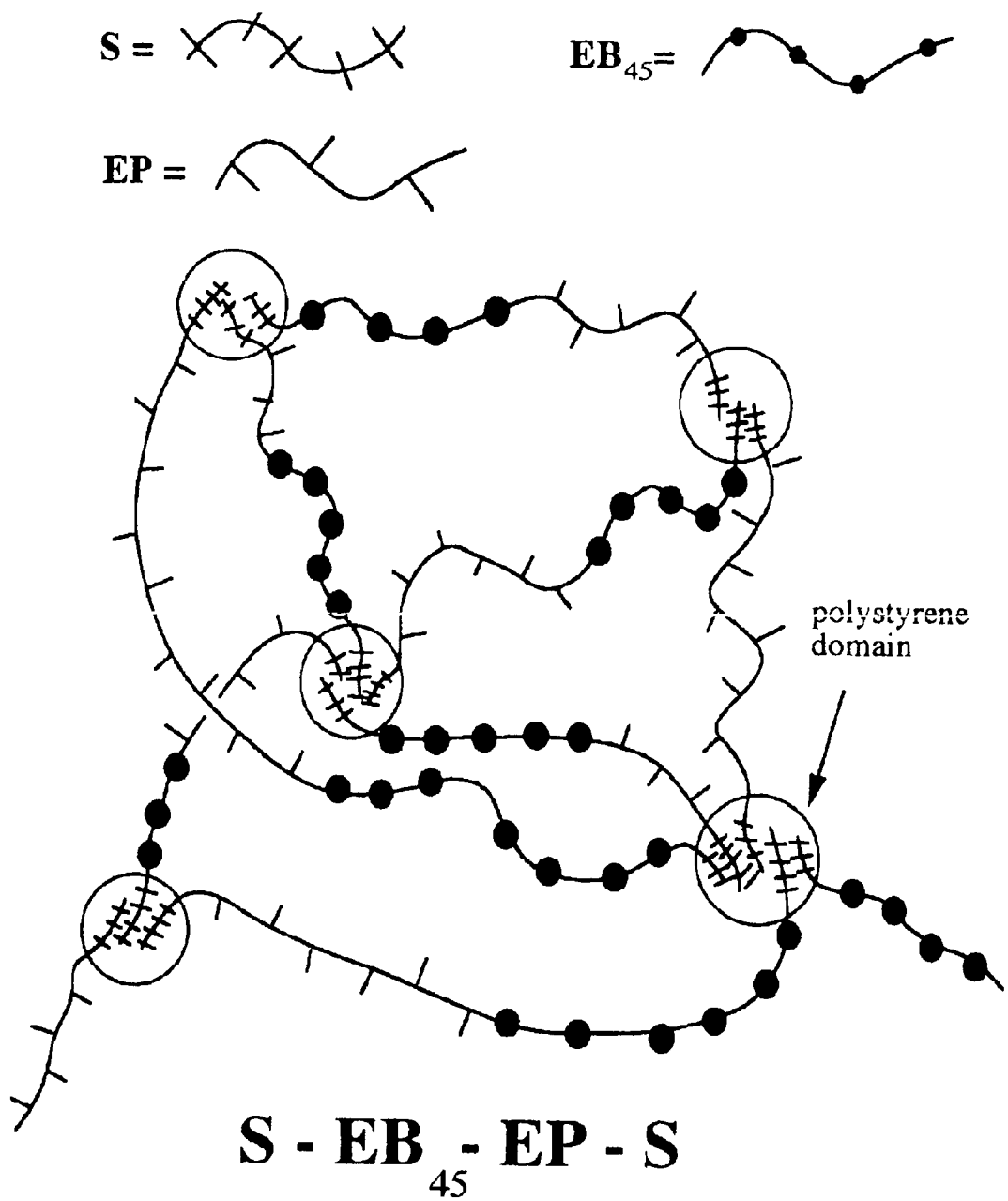
FIG. 6. Representation of S-$EB_{45}$-EP-S polystyrene domain/amorphous structure.
Figure 7:
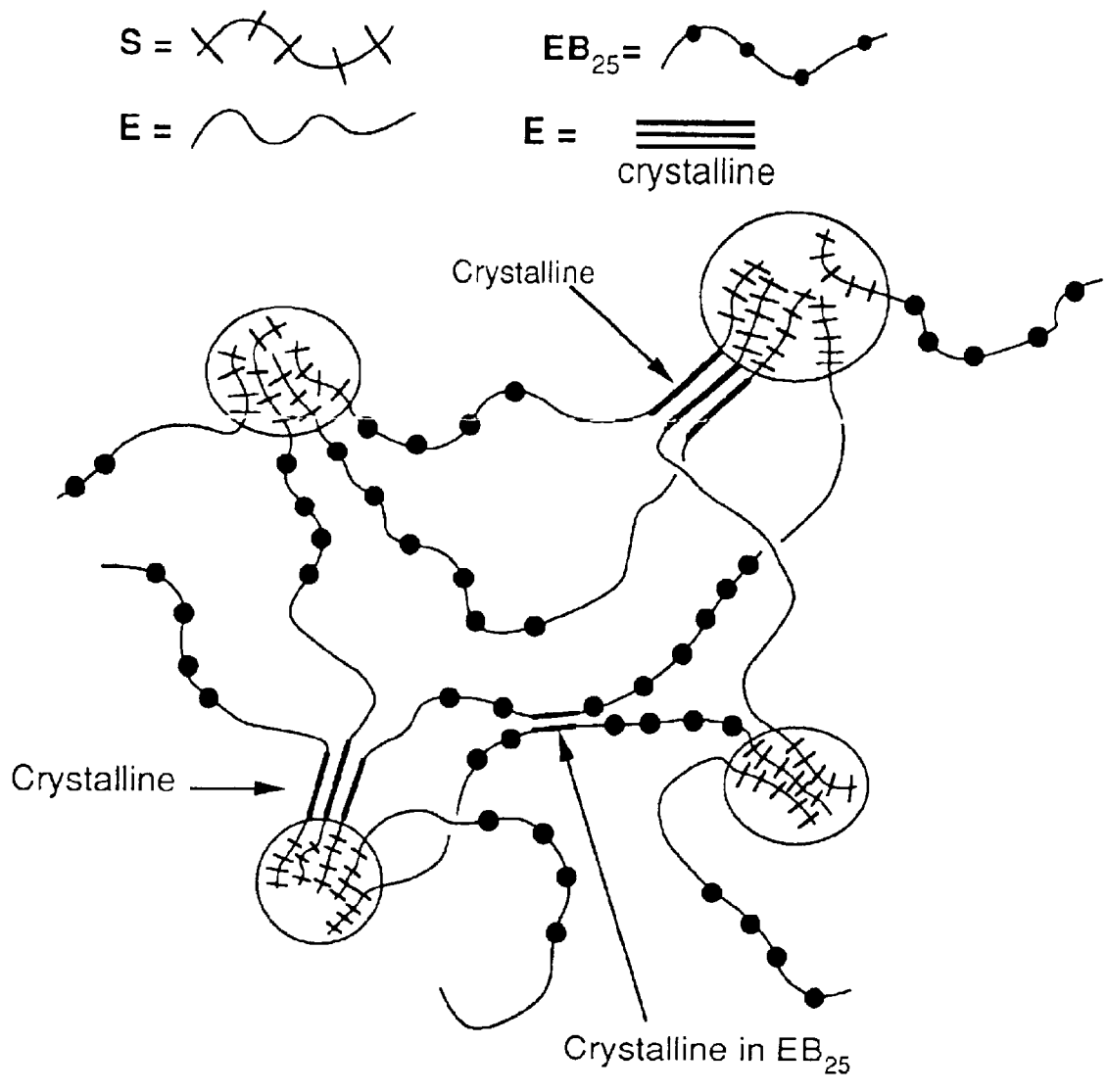
FIG. 7. Representation of S-E-$EB_{25}$-S crystalline/polystyrene domain/amorphous structure.
Figure 8:
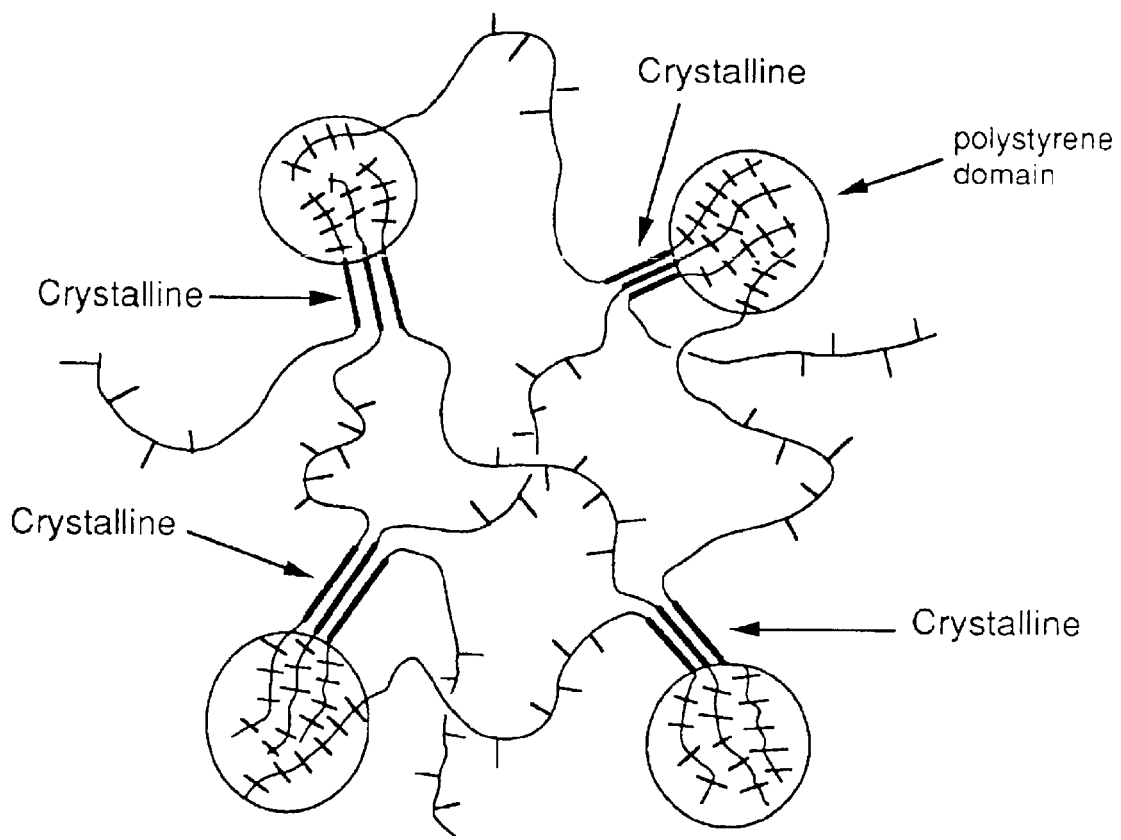
FIG. 8. Representation of S-E-EP-E-S crystalline/polystyrene domain/amorphous structure.
Figure 9:
FIG. 9. Representation of S-EP-E-EP-S crystalline/polystyrene domain/amorphous structure.
Figure 9:
Figure 9:
Figure 9:
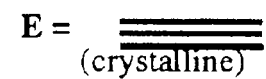
Figure 9:
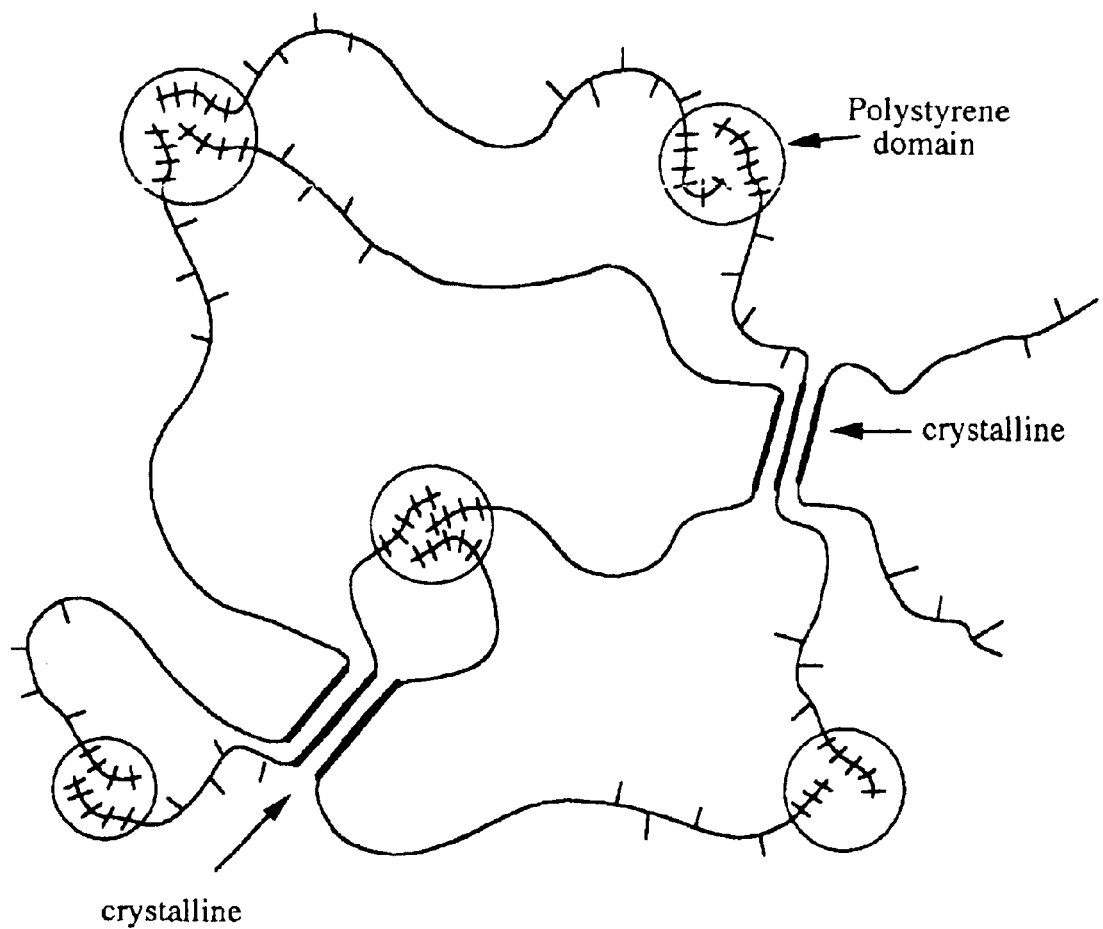
Figure 10:
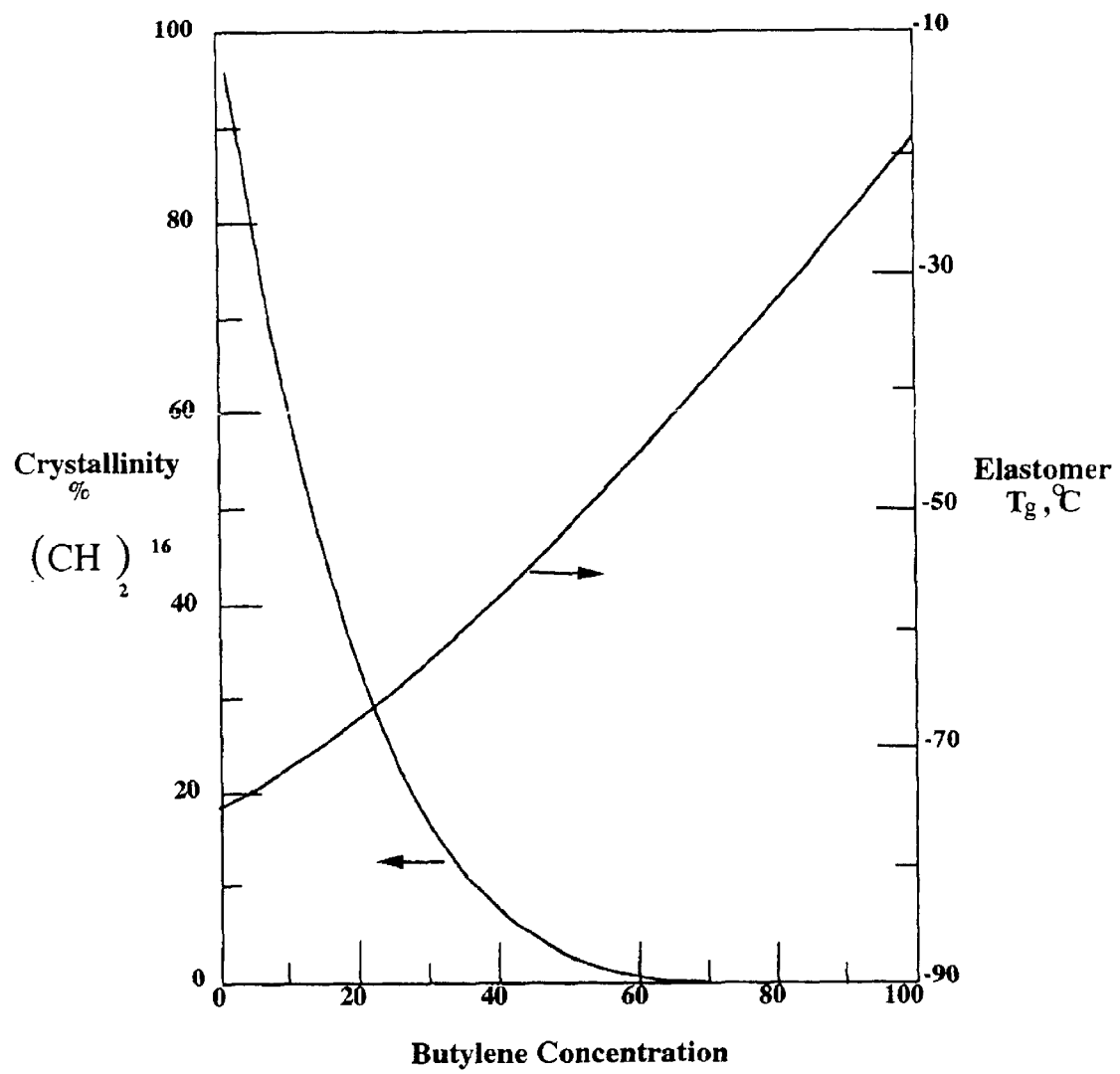
FIG. 10. Effect of butylene concentration of the percent (%) crystallinity of $(CH_2)^{16}$ units in the elastomer (midblock) phase. Reference W. P. Gergen paper at Rubber Division ACS 1985 and Legge, Norman R., paper at ACS 1987.

Chen (19) classifies 3 distinct categories of E (approximately 20–50 wt % styrene), M (approximately 50–70 wt % styrene), & S (greater than approximately 70 wt % styrene) substantially random or more appropriately pseudo-random ethylene-styrene copolymers or random copolymers of ethylene and ethylene-styrene dyads. The designated Ethylene-styrene copolymers are: E copolymers (ES16, ES24, ES27, ES28, ES28, ES30, and ES44 with styrene wt % of 15.7, 23.7, 27.3, 28.1, 39.6 & 43.9 respectively), M copolymers (ES53, ES58, ES62, ES63, and ES69 with styrene wt % of 52.5, 58.1, 62.7, 62.8, and 69.2 respectively and crystallinity, % DSC, based on copolymer of 37.5, 26.6, 17.4,22.9, 19.6 and 5.0 respectively), S copolymers (ES72, ES73, and ES74 with styrene wt % of 72.7, 72.8, and 74.3 respectively). The maximum comonomer content for crystallization of about 20% is similar in other ethylene copolymers, such as in ethylene-hexene and ethylene-vinyl acetate copolymers. If the comonomer can enter the crystal lattice, such as in ethylene-propylene, compositions in excess of 20 mol % comonomer can exhibit crystallinity. The molecular weight distribution of these copolymers is narrow, and the comonomer distribution is homogeneous. These copolymers exhibit high crystalline, lamellar morphologies to fringed micellar morphologies of low crystallinity. Crystallinity is determined by DSC measurements using a Rheometric DSC. Specimens weighing between 5 and 10 mg are heated from –80 to 180° C. at a rate of 10° C./min (first heating), held at 190° C. for 3 min, cooled to –80° C. at 10° C./min, held at –80° C. for 3 min, and reheated from –80° C. to 180° C. at 10° C./min (second heating). The crystallinity (wt %) is calculated from the second heating using a heat of fusion of 290 J/g for the polyethylene crystal. Contributing effects of the crystallinity include decrease volume fraction of the amorphous phase, restricted mobility of the amorphous chain segments by the crystalline domains, and higher styrene content of the amorphous phase due to segregation of styrene into the amorphous phase. Table I of this paper shows values of Total Styrene (wt %), aPS (wt %), Styrene (wt %), Styrene (mol %), $10^{-3}$ Mw, Mw/Mn, and total (wt %) for Ethylene-styrene copolymers ES16–ES74 while FIGS. 1–12 of this paper shows: (1) melting thermograms of ESI 1st and 2nd heating for ES16, ES27, ES44, ES53, ES63, & ES74; (2) crystallinity from DSC as a function of conmonomer content; (3) Logarithmic plot of the DSC beat of melting vs. Mole % ethylene for ESIs; (4) measured density as a function of styrene content for semicrystalline and amorphous ESIs; (5) % crystallinity from density vs % crystallinity from DSC melting enthalpy; (6) Dynamic mechanical relaxation behavior; (7) Glass transition temperature as a function of wt % ethylene-styrene dyads for semicrystalline and amorphous ESIs; (8) Arrhenius plots of the loss tangent peak temperature for representative semicrystalline and amorphous ESIs; (9) Draw ratio vs engineering strain; (10) Engineering stress-strain curves at 3 strain rates for ES27, ES63 and ES74; (11) Engineering stress-strain curves of ESIs; (12) Classification scheme of ESIs based on composition.

(20) U.S. Pat. No. 5,872,201 describes interpolymers: terpolymers of ethylene/styrene/propylene, ethylene/styrene/4-methyl-1-pentene, ethylene/styrene/hexend-1, ethylene/styrene octene-1, and ethylene/styrene/norbornene with number average molecular weight (Mn) of from 1,000 to 500,000.

(21–24) U.S. Pat. Nos. 5,460,818; 5,244,996; EP 415815A; JP07,278,230 describes substantially random, more appropriately presudo-random copolymers (interpolymers), methods of making and their uses.

(25) Alizadeh, et al., find the styrene interpolymers impedes the crystallization of shorter ethylene crystallizable sequences and that two distinct morphological features (lamellae and fringe micellar or clain clusters) are observed in ethylene/styrene (3.4 mol %) as lamella crystals organized in stacks coexisting with interlamellar bridge-like structures.

(26) Guest, et al., describes ethylene-styrene copolymers having less than about 45 wt % copolymer styrene being semicrystalline, as evidenced by a melting endotherm in DSC testing (Dupont DSC-901,10° C./min) data from the second heating curve. Crystallization decreases with increasing styrene content. Based on steric hindrance, styrene unit is excluded from the crystalline region of the copolymers. Transition from semi-crystalline to amorphous solid-state occurs at about 45 to 50 wt % styrene. At low styrene contents (<40%), the copolymers exhibit a relatively well-defined melting process. FIGS. 1–5 of this paper shows (a) DSC data in the T range associated with the melting transition for a range of ESI differing primarily in copolymer styrene content, (b) variation in percent crystallinity (DSC) for ESI as a function of copolymer S content, (c) elastic modulus versus T for selected ESI differing in S content, (d) loss modulus versus T for selected ESI differing in S content, (e) Tensile stress/strain behavior of ESI differing in S content, respectively. The above patents and publications are specifically incorporated herein by reference.

The gels of the invention comprises high levels of one or more compatible plasticizers and one or more high viscosity linear multiblock copolymers and star-shaped (or radial) multiblock copolymers having the general configurations $A^n$-Z-$A^n$ and $(A^n\text{-}Z)_n$ wherein each $A^n$ is a selected glassy polymer end block of a monoalkenyl arene compounds, more specifically, a monovinyl aromatic compounds such as polystyrene (where superscript n=1), monovinylnaphthalene as well as the alkylated derivatives thereof such as poly(alpha-methylstyrene) (n=2), poly(o-methylstyrene) (n=3), poly(m-methylstyrene) (n=4), poly(p-methylstyrene) (n=5) poly(tertiary-butylstyrene) (n=6), and the like, and midblocks (Z) comprising two or more polymer chains of poly(ethylene), poly(butylene) or poly(propylene) in combination with one or more polymer chains of poly(ethylene-butylene) or poly(ethylene-propylene). These are denoted by (E), (B), (P), (EB), and (EP) respectively.

In one embodiment of the invention, to obtain elastic crystal gels, it is necessary that the selective synthesis of butadiene produce sufficient amounts of 1,4 poly(butadiene) that on hydrogenation can exhibit "crystallinity" in the midblocks. In order for the block copolymers forming the crystal gels of the invention to exhibit crystallinity, the crystalline midblock segments must contain long runs of —$CH_2$— groups. There should be approximately at least 16 units of —($CH_2$)— in sequence for crystallinity. Only the (—$CH_2$—)$^4$ units can crystallize, and then only if there are at least 4 units of (—$CH_2$—)$^4$ in sequence; alternatively, the polyethylene units are denoted by [—($CH_2$—$CH_2$—$CH_2$—$CH_2$)—]$^4$, [(—$CH_2$—)$^4$ ]$^4$ or (—$CH_2$—)$^{16.}$ The amount of (—$CH_2$—)$^{16}$ units forming the (E) midblocks of the block copolymers comprising the crystal gels of the invention can be at least about 20% which amount is capable of exhibiting a melting endotherm in differential scanning calorimeter (DSC) curves.

In a further embodiment of the invention, ethylene-styrene copolymers produced by metallocene catalysts, using single site, constrained geometry addition polymerization catalysts resulting in substantially random poly(ethylene-styrene) copolymers such as commercially available Dow Interpolymers™, Dow S, M and E Series (ES16, ES24, ES27, ES28, ES28, ES30, ES44, ES53, ES58, ES62, ES63, ES69, ES72, ES73, ES74 and the like) can be used in combination with major or minor amounts of block copolymers of SEEPS, SEBS, and SEPS in forming gels of the invention.

A still further embodiment of the invention is a composite comprising a gel $G_n$ with a selected material $M_n$, characterized by a gel gram Bloom rigidity of about 20 to about 1,800 gram bloom, said composite made from (i) 100 parts by weight of one or more block copolymer; (ii) from about 300 to about 1,600 parts by weight of one or more selected plasticizing oils with a selected amount of at least one said plasticizing oil(s) having a viscosity of about 4 cSt at 40° C. and greater, with or without one or more of (iii) an additive; wherein said (i), (ii), and (iii) are combined t form said gelatinous elastomeric composition; wherein said block copolymer comprises A-B-A blocks, said A being selected from monoalkenularene polymers including polystyrene; said B being a hydrogenated polymer comprising a plurality of covalently linked conjugated diene monomers including a hydrogenated polymer of isoprene/butadiene; where said (i) block copolymer is poly(styrene-ethylene-ethylene-propylene-styrene); (1) said composite having layers of $G_nM_n$, $G_nM_nM_n$, or $M_nM_nG_nM_nM_n$, $M_nG_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, or permutation of one or more of said $G_n$ with $M_n$; wherein said additive is: (2) an additive selected from the group consisting of aggregation of gas bubbles formed by inert gases, and blowing agents including water, (3) an additive selected from the group consisting of internatal and external tack modifiers including, antiblocking agents, non-adhering, non-sticking modifiers including tetrakis[methylene 3,-(3'5'-di-tertbutyl-4"-hydroxyphenyl) propionatel methane, octadecyl 3-(3",5"-di-tert-butyl-4"-hydroxyphenyl) propionate, distearyl- pentaerythritol-diproprionate, thiodiethylene bis-(3,4-ter-butyl-4-hydroxy) hydrocinnamate, (1,3,5-trimethyl-2,4,6-tris[3,5-di-tert-butyl-4-hydroxybenzyl]benzene), 4,4"-methylenebis(2,6-di-tert-butylphenol), additives of stearic acid, oleic acid, stearamide, behenamide, oleamide, erucamide, N,N"-ethylenebisstearamide, N,N"-ethylenebisoleamide, sterryl drucamide, erucyl erucamide, oleyl palmitamide, stearyl stearamide, erucyl stearamide, waxes, mica, talc, zinc sterate, amorphous silica, silica, silicon dioxide, aluminum sterate, fine metallic powder, metal flakes, and silicone fluids, (4) an additive selected from the group consisting of polyisobutylene including polybutene, hydrocarbon resins including polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon, polyalphamethylstyrene/vinyl toluene copolymer, polystyrene, and elastomeric diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene), (5) an additive selected from the group consisting of flame retardants, (6) an additive selected from the group consisting of hydrocarbon resins, polyisobutylene including polybutene, additional block copolymers of poly(styrene-isoprene-styrene), poly(styrene-butadiene-styrene), poly(styrene-butadiene)$_n$, poly(styrene-isoprene)$_n$, poly(styrene-ethylene-propylene)$_n$, poly(ethylene-styrene), poly(styrene-ethylene-butylene)$_n$, particulate fillers, microspheres, butadiene rubber, poly(ethylene/propylene), and poly(ethylene/butylene), (7) an additive selected from the group consisting of poly(styrene-butadiene-styrene), polystyrene, polybutylene, poly(ethylene-porpylene), poly(ethylene-butylene), polypropylene, polyethylene, diblock copolymers of poly(styrene-butadiene)$_n$, poly(styrene-isoprene)$_n$, poly(styrene-ethylene-propylene), poly(styrene-ethylene-butylene), poly(styrene-ethylene-propylene)$_n$, poly(styrene-ethylene-butylene)$_n$, stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes, and silicone fluids, and (8) an additive selected from the group consisting of hydrocarbon resins of polystyrene, polymerized mixed olefins, polyterpene, glycerol ester of rosin, pentaerythritol ester of rosin, saturated alicyclic hydeocarbon, coumarone indene, hydrocarbon, mixed olefin, alkylated aromatic hydrocarbon, particulate fillers, and microspheres; said gel having a hydrophobic or hydrophilic surface depending on additives selected.

Advantageously, the elastomer midblock segment may have a crystallinity of at least about 20% of $(-CH_2-)^{16}$ units of the total mole % forming the midblocks of the block copolymer, more advantageously at least about 25%, still more advantageously at least about 30%, especially advantageously at least about 40% and especially more advantageously at least about 50% and higher. Broadly, the crystallinity of the midblocks can range from at least about 20% to about 60%, less broadly from at least about 18% to about 65%, and still less broadly from at least 22% to about 70%.

The melting endotherm in DSC curves of the crystalline block copolymers comprising at least 20% crystallinity are much higher than conventional amorphous block copolymers. The poly(ethylene) crystalline segments or midblocks of copolymers forming the crystal gels of the invention are characterized by sufficient crystallinity as to exhibit a melting endotherm of at least about 25° C., more advantageously of about 40° C. or higher as determined by DSC curve. The maximum in the endotherm curves of the crystalline block copolymers occurs at about 40° C., but can range from greater than about 25° C. to about 60° C. and higher. The crystalline block copolymers forming the crystal gels of the invention can exhibit melting endotherms (as shown by DSC) of about 25° C. to about 75° C. and higher. More specific melting endotherm values of the crystalline midblock block copolymers include: about 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C., 100° C., 110° C., 120° C., and higher, whereas, the melting endotherm (DSC) for conventional amorphous midblock segment block copolymers are about 10° C. and lower.

The melting endotherm is seen on heating and a sharp crystallization exotherm is seen on cooling. Such midblock crystallization endothermic and exothermic characteristics are missing from DSC curves of amorphous gels. The crystallization exotherm and fusion endotherm of the crystalline block copolymer gels of the invention are determined by ASTM D 3417 method.

Generally, the method of obtaining long runs of crystalline $-(CH_2)-$ is by sequential block copolymer synthesis followed by hydrogenation. The attainment of crystal gels of the instant invention is solely due to the selective polymerization of the butadiene monomer (forming the midblocks) resulting in one or more predetermined amount of 1,4 poly(butadiene) blocks followed by sequential polymerization of additional midblocks and hydrogenation to produce one or more crystalline midblocks of the final block copolymers.

The crystalline block copolymers are made by sequential block copolymer synthesis, the percentage of crystallinity or $(-CH_2-)^{16}$ units can be at least about $(0.67)^4$ or about 20% and actual crystallinity of about 12%. For example, a selectively synthesized S-EBn-S copolymer having a ratio of 33:67 of 1,2 and 1,4 poly(butadiene) on hydrogenation will result in a midblock with a crystallinity of $(0.67)^4$ or 20%. For sake of simplicity, when n is a subscript of -EB-, n denotes the percentage of $(-CH_2-)^4$ units, eg, n=33 or 20% crystallinity which is the percentage of $(0.67)^4$ or "$(-CH_2-)^{16}$" units. Thus, when n=28 or 72% of $(-CH_2-)^4$ units, the % crystallinity is $(0.72)^4$ or 26.87% crystallinity attributed to $(-CH_2-)^{16}$ units, denoted by -EB$_{28}$-. As a matter of convention, and for purposes of this specification involving hydrogenated polybutadiene: the notation -E- denotes at least about 85% of (—$CH_2$—)$^4$ units. The notation -B- denotes at least about 70% of [—$CH_2$—$CH(C_2H_5)$—] units. The notation -EB- denotes between about 15 and 70% [—$CH_2$—$CH(C_2H_5)$—] units. The notation -EBn- denotes n % [—$CH_2$—$CH(C_2H_5)$—] units. For hydrogenated polyisoprene: The notation -EP- denotes about at least 90% [—$CH_2$—$CH(CH_3)$—$CH_2$—$CH_2$—] units.

Generally, one or more (E) midblocks can be incorporated at various positions along the midblocks of the block copolymers. The lower flexibility of block copolymer crystal gels due to (E) midblocks can be balanced by the addition of sequentially (W) midblocks. For example, the sequentially synthesized block copolymer S-E-EB-S can maintain a high degree of flexibility due to the presence of amorphous -EB- block The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock. The sequential block copolymer S-E-B-S can maintain a high degree of flexibility due to the presence of the -B- midblock. For S-E-S, where the midblock is substantially crystalline and flexibility low, physical blending with amorphous block copolymers such as S-EB-S, S-B-S, S-EP-S, S-EB-EP-S, (S-EP)$_n$ and the like can produce more softer, less rigid, and more flexible crystal gel.

Because of the (E) midblocks, the crystal gels of the invention exhibit different physical characteristics and improvements over substantially amorphous gels including damage tolerance, improved crack propagation resistance, improved tear resistance producing knotty tears as opposed to smooth tears, crystalline melting point of at least 28° C., improved resistance to fatigue, higher hysteresis, etc. Moreover, the crystal gels when stretched exhibit additional yielding as shown by necking caused by stress induced crystallinity. Additionally, the crystallization rates of the crystalline midblocks can be controlled and slowed depending on thermal history producing time delay recovery upon deformation.

Regarding resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of amorphous and crystal gels to deformation cycles to failure (appearance of cracks, crazes, rips or tears in the gels).

Tensile strength can be determined by extending a selected gel sample to break as measured at 180° U bend around a 5.0 mm mandrel attached to a spring scale. Likewise, tear strength of a notched sample can be determined by propagating a tear as measured at 180° U bend around a 5.0 mm diameter mandrel attached to a spring scale.

Various block copolymers can be obtained which are amorphous, highly rubbery, and exhibiting minimum dynamic hysteresis:

Block Copolymer S-EB-S

The monomer butadiene can be polymerized in a ether/hydrocarbon solvent to give a 50/50 ratio of 1,2 poly(butadiene)/1,4 poly(butadiene) and on hydrogenation no long runs of —$CH_2$— groups and negligible crystallinity, ie, about $(0.5)^4$ or 0.06 or 6% and actual crystallinity of about 3%. Due to the constraints of Tg and minimum hysteresis, conventional S-EB-S have ethylene-butylene ratios of about 60:40 with a crystallinity of about $(0.6)^4$ or 0.129 or 12% and actual crystallinity of about 7.7%.

Block Copolymer S-EP-S

The monomer isoprene when polymerized will produce 95% 1,4 poly(isoprene)/5% 3,4 poly(isoprene) and upon hydrogenation will form amorphous, rubbery poly(ethylene-propylene) midblock and no long runs of —$CH_2$— and no crystallinity.

Mixed Block Copolymer S-EB/EP-S

The polymerization of a 50/50 mixture of isoprene/butadiene monomers in suitable ether/hydrocarbon solvents to give equal amounts of 1,2 and 1,4 poly(butadiene) on hydrogenation will produce a maximum crystallinity of $(0.25)^4$ or 0.4%. The actual crystallinity would be approximately about 0.2%, which is negligible and results in a good rubbery midblock.

The polymerization of a 80/20 mixture of isoprene/butadiene monomers in suitable ether/hydrocarbon solvents to give equal amounts of 1,2 and 1,4 poly(butadiene) will upon hydrogenation produce a low crystallinity of $(0.10)^4$ or 0.01%. The actual crystallinity would be approximately about 0.006%, which is negligible and results in a good rubbery midblock.

The polymerization of a 20/80 mixture of isoprene/butadiene monomers in suitable ether/hydrocarbon solvents to give equal amounts of 1,2 and 1,4 poly(butadiene) will upon hydrogenation produce a low crystallinity of $(0.4)^4$ or 2.56%. The actual crystallinity would be approximately about 1.53%, which is negligible and results in a good rubbery midblock.

The polymerization of a 20/80 mixture of isoprene/butadiene monomers in suitable ether/hydrocarbon solvents to give a 40:60 ratio of 1,2 and 1,4 poly(butadiene) will upon hydrogenation produce a low crystallinity of $(0.48)4$ or 5.3%. The actual crystallinity would be approximately about 3.2%, which is negligible and results in a good rubbery midblock.

For purpose of convince and simplicity, the hydrogenated polybutadiene are denoted as follows: -E- denotes at least 85% R-1 units, -B- denotes at least 70% R-2 units, -EB- denotes between 15 and 70% R-2 units, -EBn- denotes n % R-2 units, and -EP- denotes 90% R-3 units.

Table I below gives the % of units on hydrogenation of polybutadiene/polyisoprene copolymer midblocks

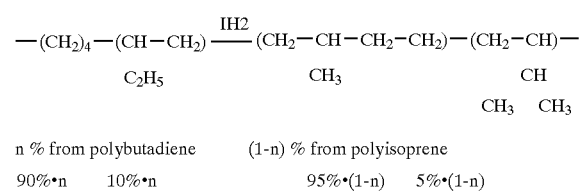

where n is the mole % polybutadiene in the polybutadiene-polyisoprene starting polymer

| n = | R-1 | R-2 | R-3 | R-4 |
|---|---|---|---|---|
| 0% | 0% | 0% | 95% | 5% |
| 20% | 18% | 2% | 76% | 4% |
| 40% | 36% | 4% | 57% | 3% |
| 60% | 54% | 6% | 38% | 2% |
| 80% | 72% | 8% | 19% | 1% |
| 100% | 90% | 10% | 0% | 0% | where

R-1 denotes $(-CH_2-)^4$,

R-2 denotes $-(CH-CH_2)-$, $C_2H_5$

R-3 denotes $-(CH_2-CH-CH_2-CH_2)-$, and $CH_3$

R-4 denotes

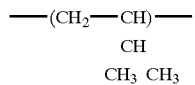

Therefore, the percentage that can crystallize is $[(-CH_2-)^4]^4$ since this is the chance of getting four $(-CH_2-)^4$ units in sequence. The percentage that will crystallize is about 60% of this.

| n = | $(-CH_2-)^4$ | $[(-CH_2-)^4]^4$ | $0.6X[(-CH_2-)^4]_n$ |
|---|---|---|---|
| 0% | 0% | 0% | 0% |
| 20% | 18% | 0.1% | 0.06% |
| 40% | 36% | 1.7% | 1.0% |
| 60% | 54% | 8.5% | 5.1% |
| 80% | 72% | 26.9% | 16.1% |
| 100% | 90% | 65.6% | 39.4% |

This applies to polymerization in a hydrocarbon solvent. In an ether (eg, diethylether), the percentage $(-CH_2-)^4$ units will be reduced so that crystallinity will be negligible.

| n = | $(-CH_2-)^4$ | $[(-CH_2-)^4]^4$ | $0.6X[(-CH_2-)^4]^n$ |
|---|---|---|---|
| 0% | 0% | 0% | 0% |
| 20% | 5% | 0.0006% | 0.0004% |
| 40% | 10% | 0.01% | 0.006% |
| 60% | 15% | 0.05% | 0.03% |
| 80% | 20% | 0.16% | 0.10% |
| 100% | 25% | 0.39% | 0.23% |

These values are all negligible. There will be no detectable crystallinity in any of these polymer midblocks. In a mixed ether/hydrocarbon solvent, values will be intermediate, depending on the ratio of ether to hydrocarbon.

The midblock components (Z) can comprise various combinations of midblocks between the selected end blocks (A); these include: -E-EB-, -E-EP-, -B-EP-, -B-EB-, -E-EP-E-, -E-EB-E, -B-EP-E-, -B-EB-E-, -B-EP-B-, -B-EB-B-, -E-E-EP-, -E-E-EB-, -B-E-EP-, -B-E-EB-, -B-B-EP-, -B-B-EB-, -E-B-EB-, -E-B-EP-, -EB-EP-, -EB-EB-, -EP-EP-, -E-EB-EB-, -E-EP-EP-, -E-EB-EP-, -E-EP-EB-, -B-EB-EB-, -B-EP-EP-, -B-EB-EP-, -B-EP-EB-, -E-EP-E-EP-, -E-EB-E-EB-, -E-EP-E-EB-, -B-EP-B-EP-, -B-EB-B-EB-, -B-EB-B-EP-, -B-EB-E-EB-, -B-EP-E-EP-, -E-EB-B-EP-, -E-EP-B-EB-, -P-EB-, -P-EP-, -P-EP-P-, -P-EB-P-, -B-EP-P-, -B-EB-P-, -P-E-EP-, -P-E-EB-, -B-P-EP-, -B-P-EB-, -P-B-EB-, -P-B-EP-, -P-EB-EB-, -P-EP-EP-, -P-EB-EP-, -P-EP-EB-, -P-EP-P-EP-, -P-EB-P-EB-, -P-EP-P-EB-, -B-EB-P-EB-, -B-EP-P-EP-, -P-EB-B-EP-, -P-EP-B-EB-, -E-EP-P-, -E-EB-P-, -E-P-EP-, -E-P-EB-, -E-EP-P-EP-, -E-EB-P-EB-, -E-EP-P-EB-, -E-EP-SE-E-E-, -B-EP-B-EP-B-, -P-EP-P-EP-P-, -E-EB-E-EB-E-, -P-EP-P-EP-P-, and the like.

The (Z) midblock of two or more polymer chains can be obtained by hydrogenation methods, for example: 1,4-polybutadiene ($B_{1,4}$) can be converted by hydrogenation to poly(ethylene), 1,4-polybutadiene ($B_{1,4}$) and 1,2-polybutadiene ($B_{1,2}$) can be converted by hydrogenation to poly(ethylene-butylene), 1,4-poly-isoprene ($I_{1,4}$) can be converted by hydrogenation to poly(ethylene-propylene), 1,2-polybutadiene ($B_{1,2}$) can be converted by hydrogenation to atactic poly(1-butene)(polybutylene), 1,4-polybutadiene ($B_{1,4}$) and polyisoprene (I) 1,4-poly-butadiene ($B_{1,4}$) can be converted by hydrogenation to poly(ethylene-ethylene-co-propylene-ethylene), 2-methyl-1,3-polybutadiene and 1,3-polybutadiene (I, $B_{1,3}$) can be converted by hydrogenation to poly(ethylene-ethylene-co-propylene), and the like. Polypropylene can be modified by tailblocking a poly(ethylene-propylene) copolymer segment on the propylene block to form poly(propylene-ethylene-co-propylene); likewise, poly(ethylene-propylene)$_n$ (EP), poly(propylene-ethylene-co-propylene-propylene) (P-EP-P), poly(propylene-ethylene-propylene) (P-E-P), poly(ethylene-ethylene-co-propylene) (E-EP) can be formed. It is noted herein that B (bold) denotes polybutadiene and B (plain) denotes polybutylene.

Further, the multiblock copolymers ($A^n$-Z-$A^n$) can be obtained by various synthesis methods including hydrogenation of selected block copolymers When the subscript n of A is=1, (polystyrene) (S), for example, suitable block copolymers can be converted to the useful multiblock copolymers forming the gels. These include: conversions of S-I-$B_{1,3}$-S to (S-E-EP-S), S-$B_{1,4}$-I-$B_{1,4}$-S to (S-E-EP-E-S), S-$B_{1,2}$-I-S to (S-B-EP-S), S-$B_{1,3}$-$B_{1,2}$-$B_{1,4}$-S to (S-E-EB-S), S-$B_{1,4}$-$B_{1,2}$I-S tom (S-EB-EP-S), S-I-$B_{1,3}$-$B_{1,2}$-$B_{1,4}$-S to (S-E-EP-EB-S), etc. As denoted herein abbreviations are interchangeably used, for example, (S-E-EP-S) denotes poly(styrene-ethylene-ethylene-co-propylene-styrene). Other linear multiblock copolymers (denoted in abbreviations) can be formed, including: (S-B-EB-S), (S-E-EB-E-S), (S-B-EP-E-S), (S-B-EB-E-S), (S-B-EP-B-S), (S-B-EB-B-S), (S-E-E-EP-S), (S-E-E-EB-S), (S-B-E-EP-S), (S-B-E-EB-S), (S-B-B-EP-S), (S-B-B-EB-S), (S-E-B-EB-S), (S-E-B-EP-S), (S-EB-EB-S), (S-EP-EP-S), (S-E-EB-EB-S), (S-E-EP-EP-S), (S-E-EB-EP-S), (S-B-EB-EB-S), (S-B-EP-EP-S), (S-B-EB-EP-S), (S-B-EP-EB-S), (S-E-EP-E-EP-S), (S-E-EB-E-EB-S), (S-E-EP-E-EB-S), (S-B-EP-B-EP-S), (S-B-EB-B-EB-S), (S-B-EB-B-EP-S), (S-B-EB-E-EB-S), (S-B-EP-E-EP-S), (S-E-EB-B-EP-S), (S-E-EP-B-EB-S), (S-P-EB-S), (S-P-EP-S), (S-P-EP-P-S), (S-P-EB-P-S), (S-B-EP-P-S), (S-B-EB-P-S), (S-P-E-EP-S), (S-P-E-EB-S), (S-B-P-EP-S), (S-B-P-EB-S), (S-P-B-EB-S), (S-P-B-EP-S), (S-P-EB-EB-S), (S-P-EP-EP-S), (S-P-EB-EP-S), (S-P-EP-EB-S), (S-P-EP-P-EP-S), (S-P-EB-P-EB-S), (S-P-EP-P-EB-S), (S-B-EB-P-EB-S), (S-B-EP-P-EP-S), (S-P-EB-B-EP-S), (S-P-EP-B-EB-S), (S-E-EP-P-S), (S-E-EB-P-S), (S-E-P-EP-S), (S-EP-EB-S), (S-E-EP-P-EP-S), (S-E-EB-P-EB-S), (S-E-EP-P-EB-S), (S-E-EP-E-EP-ES), (S-B-B-EP-B-S), (S-P-EP-P-EP-P-S), (S-E-EB-E-EB-E-S), (S-P-EP-P-EP-P-S), and the like.

The multiblock star-shaped (or radial) copolymers ($A^n$-Z)$_n$ can be obtained by various synthesis methods including hydrogenation of selected block copolymers. When the subscript n of A is=1, (polystyrene) (S), for example, suitable block copolymers can be converted to the useful multiblock copolymers forming the gels. These include: conversions of $(S-I-B_{1,3})_n$ to poly(styrene-ethylene-ethylene-co-propylene)$_n$ denoted by the abbreviation $(S-E-EP)_n$, $(S-B_{1,4}-I-B_{1,4})_n$ to $(S-E-EP-E)_n$, $S-B_{1,2}-I)_n$ to $(S-B-EP)_n$, $(S-B_{1,3}-B_{1,2}-B_{1,4})_n$ to $(S-E-EB)_n$, $(S-B_{1,4}-B_{1,2}-I)_n$ to $(S-EB-EP)_n$, $(S-I-B_{1,3}-B_{1,2}-B_{1,4})_n$ to $(S-E-EP-EB)_n$, etc. Other multiblock copolymers can be formed, including: $(S-B-EB)_n$, $(S-E-EB-E)_n$, $(S-B-EP-E)_n$, $(S-B-EB-E)_n$, $(S-B-EP-B)_n$, $(S-B-EB-B)_n$, $(S-E-E-EP)_n$, $(S-E-EB)_n$, $(S-B-E-EP)_n$, $(S-B-E-EB)_n$, $(S-B-B-EP)_n$, $(S-B-B-EB)_n$, $(S-E-B-EB)_n$, $(S-E-B-EP)_n$, $(S-EB-EB)_n$, $(S-EP-EP)_n$, $(S-E-EB-EB)_n$, $(S-E-EP-EP)_n$, $(S-E-EB-EP)_n$, $(S-B-EB-EB)_n$, $(S-B-EP-EP)_n$, $(S-B-EB-EP)_n$, $(S-B-EP-EB)_n$, $(S-E-EP-E-EP)_n$, $(S-E-EB-E-EB)_n$, $(S-E-EP-E-EB)_n$, $(S-B-EP-B-EP)_n$, $(S-B-EB-B-EB)_n$, $(S-B-EB-B-EP)_n$, $(S-B-EB-E-EB)_n$, $(S-B-EP-E-EP)_n$, $(S-E-EB-B-EP)_n$, $(S-E-EP-B-EB)_n$, $(S-P-EB)_n$, $(S-P-EP)_n$, $(S-P-EP-P)_n$, $(S-P-EB-P)_n$, $(S-B-EP-P)_n$, $(S-B-EB-P)_n$, $(S-P-E-EP)_n$, $(S-P-E-EB)_n$, $(S-B-P-EP)_n$, $(S-B-P-EB)_n$, $(S-P-B-EB)_n$, $(S-P-B-EP)_n$, $(S-P-EB-EB)_n$, $(S-P-EP-EP)_n$, $(S-P-EB-EP)_n$, $(S-P-EP-EB)_n$, $(S-P-EP-P-EP)_n$, $(S-P-EB-P-EB)_n$, $(S-P-EP-P-EB)_n$, $(S-B-EB-P-EB)_n$, $(S-B-EP-P-EP)_n$, $(S-P-EB-B-EP)_n$, $(S-P-EP-B-EB)_n$, $(S-E-EP-P)_n$, $(S-E-EB-P)_n$, $(S-E-P-EP)_n$, $(S-E-P-EB)_n$, $(S-E-EP-EP)_n$, $(S-E-EB-P-EB)_n$, $(S-E-EP-P-EB)_n$, $(S-E-EP-E-EP)_n$, $(S-B-EP-B-EP-B)_n$, $(S-P-EP-P-EP-P)_n$, $(S-E-EB-E-EB-E)_n$, $(S-P-EP-P-EP-P)_n$, and the like.

The Z and A portions of the linear and star-shaped multiblock copolymers are incompatible and form a two or more-phase system consisting of sub-micron glassy domains (A) interconnected by flexible Z chains. These domains serve to crosslink and reinforce the structure. This physical elastomeric network structure is reversible, and heating the polymer above the softening point of the glassy domains temporarily disrupt the structure, which can be restored by lowering the temperature.

Theory notwithstanding, the multiblock copolymer gel properties can be attributed to the additional blocks affecting the separate polymer phases, the additional blocks affecting the heterophase structure, the additional blocks affecting the interfacial regions between phases of the multiblock polymers or the additional blocks forming a separate phase or inducing the formation of additional separate phases. Due to the additional number of midblocks of the copolymers (I), the differences in solubility parameters between (A) and (Z) becomes greater than the solubility parameters differences between (A) and (D) of triblock copolymers, where D denotes the lone midblock polymer chain. Moreover, the presence of additional midblocks of ethylene, propylene, butylene, ethylene-propylene, or ethylene-butylene can contribute to stress-induced crystallization. This may explain why as the viscosity of the multiblock copolymers is increased to a higher level, the appearance of the gels change from crystal clear to more translucent white.

The gels of the present invention resist tearing under tensile loads or dynamic deformation in that when cut or notched, the "crack" made on the gel deep surface does not readily propagate further under dynamic deformation or tensile loads. Unlike triblock copolymer gels, such as (SEBS) and (SEPS) gels which possess high tensile strength and will catastrophically snap apart into two reflective clean smooth surfaces when cut or notched under tensile or dynamic loads. Furthermore, when elongated, the instant gels can exhibit two or more draw plateaus and can possess high tensile strength and rapid return from high extension without noticeable set or deformation. As observed, the gels can be stretched by a first tensile load with uniform deformation to a measured length, upon the application of higher tensile loads, the gel can be further extended without breaking. Upon release, the gel returns immediate to its original shape and any necking quickly disappears. Again, theory notwithstanding, the additional drawing plateaus of the gel can be attributed to yielding of crystallite formations ethylene or propylene components in the gel or yield of induced interfacial regions of concentrated ethylene or propylene between the domains which during extension absorbs the elastic energy. Likewise, the resistance to tear propagation of the instant gels when notched under tensile load can be attributed to yielding of the gel midblock components, yielding of additional phases, or yielding of interfacial regions before rupture or deformation of the (A) domains can take place.

Additionally, shearing, heating or cooling form the molten state can alter the gels' state. The instant gels can be made to exhibit long elastomeric recovery times. Such gels can be used effectively in suppressing low frequency vibrations and for absorbing energy. The unusual properties of the gels can be attributed to altering different phase or interfacial arrangements of the domains of the multiblock copolymers.

It should be noted that when the A to Z ratios falls substantially below about 30:70, various properties such as elongation, tensile strength, tear resistance and the like can decrease while retaining other desired properties, such as gel rigidity, flexibility, elastic memory.

In general, for these block copolymers, the various measured viscosities of 5, 10, 15, and 20, weight percent solution values in toluene at 30° C. can be extrapolated to a selected concentration. For example, a solution viscosity of a 5 weight percent copolymer solution in toluene can be determined by extrapolation of 10, 15, and 20 weight percent measurements to 5 weight percent concentration.

The Brookfield Viscosities can be measured at various neat polymer concentrations, for example, the selected high viscosity linear multiblock copolymers in (I) can have a typical Brookfield Viscosity value of a 20 weight percent solids solution in toluene at 25° C. of about 1,800 cps and higher, and advantageously about 2,000 cps and higher. Typically, the Brookfield Viscosity values can range from at least about 1,800 to about 16,000 cps and higher. More typically, the Brookfield Viscosity values can range from at least about IWD cps to about 40,000 cps and higher. Still more typically, the Brookfield Viscosity values can range from at least about 1,000 cps to about 80,000 cps and higher. Due to structural variations between the multiblock and star-shaped copolymers, the high viscosity star-shaped or radial copolymers, typically, may exhibit a lower Brookfield Viscosity value than its counterpart linear multiblock copolymers. However, when the multi block copolymers are considered as star-shaped or branched, than at equal branch lengths, the solution viscosities of the multiblock copolymers and branched copolymers are about the same or equivalent.

In all cases, the molecular chain lengths (molecular weights) of the multiblock and star-shaped (or radial) copolymers (I) must be sufficient to meet the high solution Brookfield Viscosities requirements described herein that is necessary for making the soft, strong and extreme tear resistant gels.

The copolymers (I) selected have Brookfield Viscosity values ranging from about 1,800 cps to about 80,000 cps and higher when measured at 20 weight percent solution in toluene at 25° C., about 4,000 cps to about 40,000 cps and higher when measured at 25 weight percent solids solution in toluene. Typical examples of Brookfield Viscosity values for star-shaped copolymers at 25 weight percent solids solution in toluene at 25° C. can range from about 3,500 cps to about 30,000 cps and higher; more typically, about 9,000 cps and higher. Other advantageous multiblock and multiblock star-shaped copolymers can exhibit viscosities (as measured with a Brookfield model RVT viscometer at 25° C.) at 10 weight percent solution in toluene of about 400 cps and higher and at 15 weight percent solution in toluene of about 5,600 cps and higher. Other advantageous multiblock and star-shaped copolymers can exhibit about 8,000 to about 20,000 cps at 20 weight percent solids solution in toluene at 25° C. Examples of most advantageous high viscosity linear multiblock copolymers can have Brookfield viscosities at 5 weight percent solution in toluene at 30° C. of from about 40 to about 50, 60, 70, 80, 90, 100 . . . 120, 150, 200 cps and higher, while viscosities of star-shaped multiblock copolymers are 150 cps and higher.

Examples of high viscosity multiblock copolymers (I) having two or more midblocks are hydrogenated styrene isoprene/butadiene block copolymers, more specifically, hydrogenated styrene block polymer with 2-methyl-1,3-butadiene and 1,3-butadiene: Kuraray's 4055 (S-E-EP-S) multiblock copolymer and 4077 (hydrogenated styrene isoprene/butadiene block copolymers) and the like, more specifically, hydrogenated styrene block polymer with 2-methyl-1,3-butadiene and 1,3-butadiene) which exhibit viscosities at 5 weight percent solution in toluene at 30° C. of about 90 cps to about 120 cps and about 200 to about 380 cps respectively. At 10 weight percent SEEPS 4055 is about 5,900 cps and higher. Other linear and star multiblock copolymers (I) such as (S-E-EP-S), (S-E-EP-E-S), (S-B-EP-S), (S-E-EB-S), (S-EB-EP-S), (S-E-EP-EB-S), (S-B-EB-S), (S-E-EB-E-S), (S-B-EP-E-S), (S-B-EB-E-S), (S-B-EP-B-S), (S-B-EB-B-S), (S-E-E-EP-S), (S-E-E-EB-S), (S-B-E-EP-S), (S-B-E-EB-S), (S-B-B-EP-S), (S-B-B-EB-S), (S-E-B-EB-S), (S-E-B-EP-S), (S-EB-EB-S), (S-EP-EP-S), (S-E-EB-EB-S), (S-E-EP-EP-S), (S-E-EB-EP-S), (S-B-EB-EB-S), (S-B-EP-EP-S), (S-B-EP-EB-S), (S-B-EB-EP-S), (S-B-EP-EB-S), (S-E-EP-E-EP-S), (S-E-EB-E-EB-S), (S-E-EP-E-EB-S), (S-B-EP-B-EP-S), (S-B-EB-B-EB-S), (S-B-EB-B-EP-S), (S-B-EP-E-EP-S), (S-E-EB-B-EP-S), (S-E-EP-B-EB-S), (S-P-EB-S), (S-P-EP-S), (S-P-EP-P-S), (S-P-EB-P-S), (S-B-EP-P-S), (S-P-E-EP-S), (S-P-E-EB-S), (S-P-EB-E-S), (S-B-P-EP-S), (S-B-P-EB-S), (S-P-E-EP-S), (S-P-E-EB-S), (S-B-P-EP-S), (S-B-P-EB-S), (S-P-B-EP-S), (S-P-B-EB-S), (S-P-EB-B-EP-S), (S-P-EP-B-EB-S), (S-P-EP-P-EP-S), (S-P-EB-P-EB-S), (S-P-EP-P-EB-S), (S-B-EB-P-EB-S), (S-B-EP-P-EP)$_n$, (S-P-EB-B-EP)$_n$, (S-P-EP-B-EB)$_n$, (S-E-EP-P)$_n$, (S-E-EB-P)$_n$, (S-E-P-EP)$_n$, (S-E-P-EB)$_n$, (S-E-EP-P-EP)$_n$, (S-E-EB-P-EB)$_n$, (S-E,EP-P-EB)$_n$, (S-E-EP-E-EP-E)$_n$, (S-B-EP-B-EP-B)$_n$, (S-P-EP-P-EP-P)$_n$, (S-E-EB-E-EB-E)$_n$, and (S-P-EP-P-EP-P)$_n$ can also exhibit viscosities at 5 weight percent solution in toluene at 30° C. of from less than about 100 to about 200, 300, 400, 500, 600, 700, 800, 900, 1,000, 1,200, 1,300, 1,600, 1,800, 2,000 cps and higher.

The copolymer (I) forming the gels can have a broad range of A end block to Z center block ratio of about 20.80 or less to about 40:60 or higher. The A:Z weight ratios can range from lower than about 20:80 to above about 40:60 and higher. More specifically, the values can be 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and etc. Other ratio values of less than 19:81 or higher than 51:49 are also possible. Broadly, the styrene block to elastomeric block ratio A:Z of the high viscosity multiblock and star copolymers (I) is about 20:80 to about 40.60 or higher, less broadly about 31:69 to about 40:60, preferably about 32:68 to about 38:62, more preferably about 32:68 to about 36:64, particularly more preferably about 32:68 to about 34:66, especially more preferably about 33.67 to about 36:64, and most preferably about 30.70.

The multiblock copolymers (I) such as Kuraray's (S-E-EP-S) 4055 and 4077 while exhibiting a high viscosity also have a lower (30:70) S:E-EP ratio which makes it of advantage in processing the high molecular weight, high viscosity multiblock copolymers into a gel at suitable temperatures.

The gels can optionally comprise selected major or minor amounts of one or more polymers or copolymers (II) provided the amounts and combinations are selected without substantially decreasing the desired properties. The polymers and copolymers can be linear, star-shaped, branched, or multiarm; these including: (SBS) styrene-butadiene-styrene block copolymers, (SIS) styrene-isoprene-styrene block copolymers, (low styrene content SEBS) styrene- ethylene-butylene-styrene block copolymers, (SEP) styrene-ethylene-propylene block copolymers, (SEPS) styrene-ethylene-propylene-styrene block copolymers, (SB)$_n$ styrene-butadiene and (SEB)$_n$, (SEBS)$_n$, (SEP)$_n$, (SI)$_n$ styrene-isoprene multi-arm, branched or star-shaped copolymers, polyethyleneoxide (EO), poly(dimethylphenylene oxide) and the like. Still, other (II) polymers include homopolymers which can be utilized in minor amounts; these include: polystyrene, polybutylene, polyethylene, polypropylene and the like. The conventional term "major" means about 51 weight percent and higher and the term "minor" means 49 weight percent and lower.

Example of (II) polymers, copolymers, and blends include: (a) Kraton G 1651, G 1654X; (b) Kraton G 4600; (c) Kraton G 4609, other suitable high viscosity polymer and oil s include: (d) Tuftec H 1051; (e) Tuftec H 1041; (f) Tuftec H 1052; (g) Kuraray SEEPS 4033 (hydrogenated styrene isoprene/butadiene block copolymers, more specifically, hydrogenated styrene block polymer with 2-methyl-1,3-butadiene and 1,3-butadiene); (h) Kuraray SEBS 8006; (i) Kuraray SEPS 2005; (j) Kuraray SEPS 2006, and (k) blends (polyblends) of (a)-(h) with other polymers and copolymers include: (1) SEBS-SBS; (2) SEBS-SIS; (3) SEBS-(SEP); (4) SEBS-(SEB)$_n$; (5) SEBS-(SEB)$_n$; (6) SEBS-(SEP)$_n$; (7) SEBS-(SI)$_n$; (8) SEBS-(SI) multiarm; (9) SEBS-(SEB)$_n$; (10) (SEB)$_n$ star-shaped copolymer, (11) s made from blends of (a)-(k) with other homopolymers include: (12) SEBS/ polystyrene; (13) SEBS/polybutylene; (14) SEBS/ polyethylene; (14) SEBS/polypropylene; (16) SEP/SEBS, (17) SEP/SEPS, (18) SEP/SEPS/SEB, (19), SEPS/SEBS/ SEP, (20), SEB/SEBS (21), EB-EP/SEBS (22), SEBS/EB (23), SEBS/EP (24), (25) $(SEB)_n$ s, (26) $(SEP)_n$, (27) Kuraray 2007 (SEPS), (28) Kuraray 2002, (SEPS) and the like.

Representative examples of commercially available elastomers that can be combined include multiblock and star-shaped copolymers (I and II) described above including: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, 7340, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940, FG1901X and FG1921X. Kuraray's SEPS, SEP/SEPS or SEP/SEB/SEPS Nos. SEP 1001, SEP 1050, 2027, 2003, SEPS 2006, SEPS 2023, SEPS 2043, SEPS 2063, SEPS 2050, SEPS 2103, SEPS 2104, SEPS 2105, SEEPS 4045 (hydrogenated styrene isoprene/butadiene block copolymers, more specifically, hydrogenated styrene block polymer with 2-methyl-1,3-butadiene and 1,3-butadiene), SEBS 8004, SEBS 8007, H-VS-3 (S-V-EP-S) and the like. Typical representative Dow Ethylene-styrene copolymers include ES16, ES24, ES27, ES28, ES28, ES30, ES44 with styrene wt % of 15.7, 23.7, 27.3, 28.1, 39.6 & 43.9 respectively, M copolymers (ES53, ES58, ES62, ES63, and ES69 with styrene wt % of 52.5, 58.1, 62.7, 62.8, and 69.2 respectively and crystallinity, %, DSC, based on copolymer of 37.5, 26.6, 17.4, 22.9, 19.6 and 5.0 respectively), S copolymers (ES72, ES73, and ES74 with styrene wt % of 72.7, 72.8, and 74.3 respectively). Other grade copolymers include ES60 (melt index 0.1, 0.5, 3, 10), ES20 (M=0.1. 0.5, 3, 11). The Brookfield Viscosity of a 5 weight percent solids solution in toluene at 30° C. of 2006 is about 27. Typical Brookfield Viscosities of a 10 weight percent solids solution in toluene at 30° C. of Kuraray SEP 1001, SEP 1050, SEPS 2007, SEPS 2063, SEPS 2043, SEEPS 4033, SEPS 2005, SEPS 2006, are about 70,70,17,29,32,50,1200, and 1220 respectively. Typical Brookfield Viscosity of a 25 weight percent solids solution in toluene at 25° C. of Kraton D1101, D1116, D1184, D1300X, G1701X, G1702X are about 4000, 9000, 20000, 6000, 50000 and 50000 cps respectively. Typical Brookfield Viscosity of a 10 weight percent solids solution in toluene at 25° C. of G1654X is about 370 cps. The Brookfield Viscosities of a 20 and 30 weight percent solids solution in toluene at 30° C. of H-VS-3 are about 133 cps and 350 cps respectively.

Suitable triblock copolymers (II) and their typical viscosities are further described: styrene-ethylene-butylene-styrene block copolymers (SEBS) available from Shell Chemical Company and Pecten Chemical Company (divisions of Shell Oil Company) under trade designations Kraton G 1651, Kraton G 1654X, Kraton G 4600, Kraton G 4609 and the like. Shell Technical Bulletin SC:1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68–79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity SEBS triblock copolymers includes Kuraray's SEBS 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 5 weight percent solution in toluene at 30° C. of about 28 cps, at 10 weight percent of about 1200 cps, and at 20 weight percent 76,000 cps. Other grades of SEBS, SEPS, $(SEB)_n$, $(SEP)_n$ polymers can also be utilized in the present invention provided such polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's SEBS polymer 8006 the S:EB weight ratio is about 35:65. In the case of Kuraray's 2005 (SEPS), and 2006 (SEPS), the S:EP weight ratios are 20:80 and 35:65 respectively. Much like S:EB ratios of SEBS and $(SEB)_n$, the SEP ratios of very high viscosity SEPS triblock copolymers are about the same and can typically vary as broadly.

The triblock copolymers (II) such as Kraton G 1654X having ratios of 31:69 or higher can be used and do exhibit about the same physical properties in many respects to Kraton G 1651 while Kraton G 1654X with ratios below 31:69 may also be use, but they are less advantageous due to their decrease in the desirable properties of the final gel.

Plasticizers particularly advantageous for use in practicing the present invention are will known in the art, they include rubber processing oils such as parffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

Examples of representative commercially available plasticizing oils include Amoco® polybutenes, hydrogenated polybutenes, polybutenes with epoxide functionality at one end of the polybutene polymer, liquid poly(ethylene/ butylene), liquid hetero-telechelic polymers of poly (ethylene/butylene/styrene) with epoxidized polyisoprene and poly(ethylene/butylene) with epoxidized polyisoprene: Example of such polybutenes include: L14 (320 Mn), L-50 (420 Mn), L-100(460 Mn), H-15 (560 Mn), H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. Viscosity), Actipol E6 (365 Mn), E16 (973 Mn), E23 (1433 Mn), Kraton L-1203, EKP-206, EKP-207, HPVM-2203 and the like. Example of various commercially oils include: ARCO Prime (55, 70, 90, 200, 350, 400 and the like), Duroprime and Tufflo oils (6006, 6016, 6016M, 6026, 6036, 6056, 6206, etc), other white mineral oils include: Bayol, Bernol, American, Blandol, Drakeol, Ervol, Gloria, Kaydol, Utetek, Lyondell (Duroprime 55, 70, 90, 200, 350, 400, etc), Marcol, Parol, Peneteck, Primol, Protol, Sontex, and the like.

As described at page 23 of copending applications U.S. Ser. No. 09/285,809 and incorporated by reference above, minor amounts of one or more compatible plasticizers can be utilized in forming the invention gels. In providing non-tack gels, major amount of plasticizers used can be low viscosity platicizers having viscosities advantageously of not greater than typically about 30 cSt @ 40° C., for example 30, 29, 28, 27, 26, 25, 24, 23, 22, 21, 20, 19, 18, 17, 16, 15, 14, 13, 12, 11, 10, 9, 8, 7, 6, 5, 4, and the like. Such typical low viscosity plasticizers are commercially available as, for example, Witco, Rudol, Ervol, Benol, Blandol, Carnation, Klearol, Semtol100, Semtol 85, Semtol 70, Semtol 40; Lyondell Duroprime 55, 70, 90, Duroprime DS L & M, Duropac 70, 90, Crystex 22, Crystex AF L & M, Rufflo 6006, 6016 and the like.

Generally, various low to high viscosity commercially available plasticizing oils with average molecular weights ranging from less than about 200 to greater than about 700 may also be used (e.g. H-300 (1290 Mn)). It is well know that minor and sufficient amounts of Vitamin E is added to the described commercially available oils during bulk processing which is useful as a oil stabilizer, antioxidant, and preservative.

Of all the factors, the amount and varying viscosities of plasticizing oils can be controlled and adjusted advantageously to obtain various inherent properties, including substantially higher tear and tensile strength gels, and the like. The improvements in tensile strength of the gels are accompanied by responding increase in gel rigidity as the amount of plasticizing oils can be lowered until the rigidity of the gels becomes much higher than that of the rigidity of the gums (for example) which surround the teeth. Although higher tensile strengths can be obtained as the amount of plasticizing oils in the gel approaches zero, the tensile strength of the floss, however, must be maintained at an acceptable gel rigidity (at sufficient high plasticizing oil levels) in order to be as soft as the gums required for flossing. For example, the rigidities of a gel containing 100, 200, or 300 parts by weight of oil is much higher than a gel containing 300, 400, 500, 600, 800, or 900 parts of oil. Selected amounts of one or more low viscosity plasticizers can be use to advantage in forming the gels of the invention having little or no tack.

These gels can exhibit a larger unit lateral contraction at the same elongation per unit of length as their counterpart parent gels from which the new gels are derived or formed. This property would allow a same unit volume of gel when elongated as its parent to easily wedge between the teeth when flossing. It would seem that a gel having the 1.0 cm$^3$ volume made from a ratio of 100 parts by weight of copolymer and 400 pats plasticizer would have a unique macro volume configurations that is at equilibrium with the plasticizer which is much like a 3-D fingerprint which is uniquely different from any other gel of a different copolymer to plasticizer ratio. Reducing the plasticizer content of a ratio 100:400 gel to a 100:300 ratio of copolymer to plasticizer will decrease the amount of plasticizer, but the original macro volume configurations will remain the same.

Speculative theories not withstanding, configurations may take the form of (1) swiss cheese, (2) sponge, (3) the insides of a loaf of bread, (4) structures liken to ocean brain corals, (5) large structures and small structures forming the 3-D gel volume landscape, (6) the outer heated surface which cools faster than the inner volumes of the gel during its cooling histories may have a patterned crust (rich in A microphases) like that of a loaf of bread and the inner volume may have much like 1–5, and (7) the many different possible structures are unlimited and volume landscapes may be interconnected at the macro-level by threads or microstrands of Z microphases.

The amount of plasticizer extracted can advantageously range from less than about 10% by weight to about 90% and higher of the total weight of the plasticizer. More advantageously, the extracted amounts of plasticizer can range from less than about 20% by weight to about No by weight of the total plasticizer, and still more advantageously, from about 25% to about 75%. Plasticizing oils contained in the gels can be extracted by any conventional methods, such as solvent extraction, physical extraction, pressure, pressure-heat, heat-solvent, pressure-solvent-heat, vacuum extraction, vacuum-heat extraction, vacuum-pressure extraction, vacuum-heat-pressure extraction, vacuum-solvent extraction, vacuum-heat-solvent-pressure extraction, etc. The solvents selected, should be solvents which do not substantially disrupt the A and Z phases of the (I) copolymers forming the gels . Any solvent which will extract plasticizer from the gel and do not disrupt the A and Z phases can be utilized. Suitable solvents include alcohols, primary, secondary and tertiary alcohols, glycols, etc., examples include methanol, ethanol, tetradecanol, etc. Likewise, the pressures and heat applied to remove the desired amounts of oils should not be sufficient to disrupt the A and Z domains of the (1) copolymers. To form a lower rigidity gel, the simplest method is to subject the gel to heat in a partial vacuum or under higher vacuum for a selected period of time, depending on the amount of plasticizer to be extracted.

The gels can be made non-adhearing, non-sticking, (non-tacky) by using major or minor amounts of one or more low viscosity plasticizers, by incorporating an advantage amount of stearic acid (octadecanoic acid), metal stearates (e.g., calcium stearate, magnesium stearate, zinc stearate, etc.), polyethylene glycol distearate, polypropylene glycol ester or fatty acid, and polytetramethylene oxide glycol distearate, waxes, stearic acid and waxes, metal stearate and waxes, metal stearate and stearic acid. The use of stearic acid alone do not reduce tack. The amount of stearic acid is also important. As an example, ratio of 200 grams stearic acid to 2,000 gram of SEBS (a ratio of 0.1) will result in spotted tack reduction on the surface of the gel. A ratio of 250 to 2,000 will result in spotted crystallized regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grams of SEBS. The same excellent results is achieved when SEBS is adjusted to 3,000 grams, 4,000 grams, etc. The same result is achieved with (I) copolymers as well as in combination with polymers (1I) such as SEPS, $(SEB)_n$, $(SEP)_n$ polymers.

As described at pages 23–27 of copending applications U.S. application Ser. No. 09/285,809 and pages 20–23 of U.S. application Ser. No. 09/274,498 incorporated by reference above, polyphenolics with one or more sterically hindered phenolic hydroxy groups when incorporated into the invention gels will result in the appearance of large crystals in the interior as well as on the surface of the gels. The crystals have no effect on the high COF of the resulting gels. When selected amounts of internal nucleating agents are incorporated in the invention gels in combination with selected amounts or one or more of a low coefficient of friction (COF) agents, the large crystals no longer forms within the gels; and the surface of the gels exhibit lower and lower COF with time. Bringing the gels in contact with selected external nucleating agents decreases the time or totally eliminates the time needed for the gel's outer surface to exhibit a low COF.

The gels and soft elastomers incorporating low COF agents and internal and/or external nucleating agents exhibit a much lower coefficient of friction when measured in contact with a reference surface than gels and soft elastomers made without such components.

School book physics teaches COF can be determined experimentally, for two given surfaces that are dry and not lubricated, the ratio of the tangential force needed to overcome the friction to the normal force which holds the two surfaces in contact (e.g., the weight of a block of gel or elastomer material on a surface) is a constant, independent of the area or of the velocity with which the surfaces (surface of a side of the block in contact with another surface) move over wide limits. This ratio is $\mu$, the coefficient of friction. The coefficient of sliding friction for a block of material being $$\mu = (f/F_n)$$

where f is the force of friction, and $F_n$ the normal force. For the case of the block on the horizontal table. If m is the mass of the block, then mg is the normal force and the above equation can be written as $$\mu = f/mg.$$

In the case the block of a block rests on a board, originally horizontal, and that the board then is tilted until a limiting angle ø is reached, beyond which the block will begin to slide down the board. At this angle the component of the weight of the object along the board is just equal in amount to that necessary to overcome the force of friction. The force down the plane is mg sin ø, while the normal force is mg cos ø. Therefore we have $$\mu = (mg \sin ø)/(mg \cos ø) \text{ or } \mu = \tan ø.$$

The limiting value of ø for which $\mu = \tan ø$ is true is call the angle of repose. Measurement of the tangent of this angle will give the coefficient of friction of the contacting surfaces of the block and the board that slide one upon the other. As an example of low COF agents advantageously useful in sofr thermoplastiv elastomers and gels, excellent results is achieved with 50 g rams of a polyphenolic with sterically hindered phenolic hydroxyl groups (Irganox 1010), about 100 of one or more nucleating agents (such as very fine particle size sodium benzoate, dibenzylidene sorbitol, its alkylated derivatives, talc, zinc sterate, amorphous silica, aluminum sterate, etc.) and 5,000 grams of S-EB-S and 25,000 gram of oil. The same excellent result is achieved when S-EB-S is adjusted to 3,000 grams, 4,000 grams, etc. The same result is achieved with copolymers as well as in combination with other polymers. Moreover, when about 50 grams of tetrakis[methylene 3,-(3'5'-di-tertbutyl-4"-hydroxyphenyl) propionatel methane is use (per about 22.68 kilograms of 50 lbs of gel) as a low COF agent, tack is completely removed from the surface of the gel after two to three weeks of blooming.

When this is repeated with an external nucleating agent, such as with various fine particles for coating the outside surface of the elastomer or gel which fin particles can also be useful for removing tack, such as with talc, calcium stearate, zinc sterate, amorphous silica, aluminum sterate, fine flour, corn starch, fine soil, fine sand, fine metallic powder, vacuum dust, fine wood dusts and the like, lower COF of the gel surface by internal nucleating agents can be achieved within a few days to less than several hours. After coating the gel for the desired period of time, the fine polar and water soluble particles can be washed off with water and soap, while non-polar and non-water soluble fine powders including talc can be removed by wearing it off or by lifting it off with the use of adhesive tapes if so desired.

What is the surface properties of low CFO agents at the air/plasticizer-copolymer interface? Theory notwithstanding, the resulting gel surface will comprise of very fine molecular segments or even very fine crystal grains of low COF agents confined at the air/plasticizer and polymer interface. Depending on concentration, the non-polar segments of the low COF agents will have a tendency of being adsorpted by the predominate plasticizer and copolymer midblock phase at the gel surface. The slightly polar or more polar segments of the low COF agents are adsorbed to a lesser extent by the plasticizer-copolymer surface. This is supported by observing the water wetting characteristics at the gel surface with and with out low COF agents at the air gel surface interface. A drop of water will bead up and not readily wet the gel surface free of any low COF agents (hydrophobic). The presence of even slightly polar low COF agents exposed on the surface of the gel will make a drop of water flatten out and not bead up when place on the gel surface (hydrophilic).

Commercial high melting point, low oil solubility, and polar low COF agents such as polyphenolics which are advantageously useful in the present invention include: Ethanox 330 (Ethyl), Irganox 1010 (Ciba-Geigy), Santechheim A/O 15-1 (Santech), Ultra 210 (GE), Hostanox 03 (Hoechst Celanese), Irganox 3114 (Ciba-Geigy), Mixxim AO-3 (Fairmont), and the like. Other high melting point, low oil solubility, polar low COF agents contemplated are common amino acids: Such As Alamine, Arginine, Asparagine, Aspartic Acid, Cysteine, Glutamine, Glutamic Acid, Glycine, Histidine, Isoleucine, Leucine, Lysine, Methionine, Phenylalanine, Pfoline, Serine, Threonine, Tryptophan, Tyrosine and Valine. The melting points of these amino acids range from about 178° C. to about 344° C. The amino acids having greater advantage serving as low COF agents are Asparagine, Aspartic acid. Glutamine, Glutamic acid, Tryptophan, and Tyrosine.

Copolymer for forming the low COF compositions include block copolymers, random copolymers, metallocene catalyzed ethylene-styrene copolymers, Low COF gels made from thermoplastic elastomer copolymers and block copolymers having one or mor substantially crystalline polyethylene segments or midblocks. The low COF gels advantageously exhibit high, higher, and higher, and ever higher tear resistance than realized before as well as improved high tensile strength. The low COF gels also exhibit improved damage tolerance, crack propagation resistance and especially improved resistance to high stress rupture which combination of properties makes the gels advantageously and surprisingly suitable for any desired use including toys, inflatable air cushions in automobiles, and the like.

The invention gels are advantageously useful for making low COF gel sompositions. Moreover, various polymer gels made from linear triblock copolymers, multi-arm block copolymers, branched block copolymers, radial block copolymers, multiblock copolymers, random/non-random copolymers, thermosplastic crystalline polyurethane copolymers with hydrocarbon midblocks or mixtures of two or more of such copolymers can also be made with low COF.

The invention gels can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties. Additives useful in the gel of the present invention include: tetrakis[methylene 3,-(3'5'-di-tertbutyl-4"-hydroxyphenyl)propionate]methane, octadecyl 3-(3",5"-di-tert-butyl-4-hydroxyphenyl)propionate, distearyl-pentaerythritol-diproprionate, thiodiethylene bis-(3,5-ter-butyl-4-hydroxy)hydrocinnamate, (1,3,5-trimethyl-2,4,6-tris[3,5-di-tert-butyl-4hydroxybenzyl]benzene), 4,4"-methylenebis(2,6di-tert-butylphenol), stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g. polyethylene, polypropylene, microcrystalline, carnauba, paraffin, montan, candelilla beeswax, ozokerite, ceresine, and the like). The gel can also contain metallic pigments (aluminum and brass flakes), $TiO_2$, mica, fluorescent dyes and pigments, phosphorescent pigments, aluminatrihydrate, antimony oxide, iron oxides ($Fe_2O_3$, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass, microspheres, barium ferrite, wollastonite and the like. The report of the committee on Magnetic Materials, Publication NMAB-426, National Academy Press (1985) is incorporated herein by reference.

The gels can also be made into composites. The gels can be casted unto various substrates, such as open cell materials, metals, ceramics, glasses, and plastics, elastomers, fluropolymers, expanded fluropolymers, Teflon (TFE, PTFE, PEA, FEP, etc), expanded Teflon, spongy expanded nylon, etc.; the molten gel composition is deformed as it is being cooled. Useful open-cell plastics include: polyamides, polyimides, polyesters, polyisocyanurates, polyisocyanates, polyurethanes, poly (vinyl alcohol), etc. Open-celled Plastic (sponges) suitable for use with the compositions are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The gels denoted as "G" can be physically interlocked with a selected material denoted as "M" to form composites as denoted for simplicity by their combinations $G_nG_n$, $G_nM_n$, $G_nM_nG_n$, $M_nG_nM_n$, $M_nG_nG_n$, $G_nG_nM_n$, $M_nM_nG_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nG_nM_n$, $G_nM_nG_nM_nM_n$, $M_nG_nM_n$ $G_nM_nG_n$, $G_nG_nM_nM_nG_n$, $G_nG_nM_nG_nM_nG_n$, and the like or any of their permutations of one or more $G_n$ with $M_n$ and the like, wherein when n is a subscript of M, n is the same or different selected from the group consisting of foam, plastic, fabric, metal, concrete, wood, glass, ceramics, synthetic resin, synthetic fibers or refractory materials and the like: wherein when n is a subscript of G, n denotes the same or a different gel rigidity of from about 2 gram to about 1,800 gram Bloom). The gels of the composites are formed from copolymers (I), polymers (II), and plasticizers (III) described above This physical elastomeric network structure is reversible, and heating the polymer above the softening point of the glassy domains temporarily disrupt the structure, which can be restored by lowering the temperature. During mixing and heating in the presence of compatible plasticizers, the glassy domains (A) unlock due to both heating and solvation and the molecules are free to move when shear is applied. The disruption and ordering of the glassy domains can be viewed as a unlocking and locking of the elastomeric network structure. At equilibrium, the domain structure or morphology as a function of the (A) and (Z) phases (mesophases) can take the form of spheres, cylinders, lamellae, or bicontinous structures. The scale of separation of the phases are typically of the order of hundreds of angstroms, depending upon molecular weights (i.e. Radii of gyration) of the minority-component segments. The sub-micron glassy domains which provides the physical interlocking are too small to see with the human eye, too small to see using the highest power optical microscope and only adequately enough to see using the electron microscope. At such small domain scales, when the gel is in the molten state while heated and brought into contact to be formed with any substrate and allowed to cool, the glassy domains of the gel become interlocked with the surface of the substrate. At sufficiently high enough temperatures, with or without the aid of other glassy resins (such as polystyrene homopolymers and the like), the glassy domains of the copolymers forming the gels fusses and interlocks with even a visibly smooth substrate surface such as glass. The disruption of the sub-micron domains due to heating above the softening point forces the glassy domains to open up, unlocking the network structure and flow. Upon cooling below the softening point, the glassy polymers reforms together into sub-micron domains, locking into a network structure once again, resisting flow. It is this unlocking and locking of the network structure on the sub-micron scale with the surfaces of various materials which allows the gel to form interlocking composites with other materials.

A useful analogy is to consider the melting and freezing of a water saturated substrate, for example, foam, cloth, fabric, paper, fibers, plastic, concrete, and the like. When the water is frozen, the ice is to a great extent interlocked with the substrate and upon heating the water is able to flow. Furthermore, the interlocking of the ice with the various substrates on close examination involves interconnecting ice in, around, and about the substrates thereby interlocking the ice with the substrates. A further analogy, but still useful is a plant or weed well established in soil, the fine roots of the plant spreads out and interconnects and forms a physical interlocking of the soil with the plant roots which in many instances is not possible to pull out the plant or weed from the ground without removing the surrounding soil also.

Likewise, because the glassy domains are typically about 200 Angstroms in diameter, the physical interlocking involve domains small enough to fit into and lock with the smallest surface irregularities, as well as, flow into and flow through the smallest size openings of a porous substrate. Once the gel comes into contacts with the surface irregularities or penetrates the substrate and solidifies, it becomes difficult or impossible to separate it from the substrate because of the physical interlocking. When pulling the gel off a substrate, most often the physically interlocked gel remains on the substrate. Even a surface which may appear perfectly smooth to the eye, it is often not the case. Examination by microscopy, especially electron microscopy, will show serious irregularities. Such irregularities can be the source of physical interlocking with the gel.

Such interlocking with many different materials produce gel composites having many uses. The high tear resistant soft crystal gels are advantageously suitable for a safer impact deployable air bag cushions, other uses include: toys; games; novelty, or souvenir items; elastomeric lenses, light conducing articles, optical fiber connectors; athletic and sports equipment and articles; medical equipment and articles including derma use and for the examination of or use in normal or natural body orifices, health care articles; artist materials and models, special effects; articles designed for individual personal care, including occupational therapy, psychiatric, orthopedic, podiatric, prosthetic, orthodontic and dental care; apparel or other items for wear by and on individuals including insulating gels of the cold weather wear such as boots, face mask, gloves, full body wear, and the like have as an essential, direct contact with the skin of the body capable of substantially preventing, controlling or selectively facilitating the production of moisture from selected parts of the skin of the body such as the forehead, neck, foot, underarm, etc; cushions, bedding, pillows, paddings and bandages for comfort or to prevent personal injury to persons or animals; housewares and luggage; articles useful in telecommunication, utility, industrial and food processing, and the like as further described herein.

The selected amount of crystallinity in the midblock should be sufficient to achieve improvements in one or more physical properties including improved damage tolerance, improved crack propagation resistance, improved tear resistance, improved resistance to fatigue of the bulk gel and resistance to catastrophic fatigue failure of crystal gel composites, such as between the surfaces of the crystal gel and substrate or at the interfaces of the interlocking material (s) and crystal gel, which improvements are not found in amorphous gels at corresponding gel rigidities.

As an example, when fabric interlocked or saturated with amorphous S-EB-S gels (gel composites) are used as gel liners for lower limb or above the knee prosthesis to reduce pain over pressure areas and give relief to the amputee, the commonly used amorphous gels forming the liners can tear or rip apart during marathon racewalk after 50–70 miles. In extended use, the amorphous gels can rip on the bottom of the liner in normal racewalk training of 40–60 miles over a six weeks period. In such demanding applications, the crystal gels are especially advantageous and is found to have greater tear resistance and resistance to fatigue resulting from a large number of deformation cycles than amorphous gels. The crystal gels are also useful for forming various orthotics and prosthetic articles such as for lower extremity prosthesis of the L5664 (lower extremity socket insert, above knee), L5665 (socket insert, multi-durometer, below knee), L5666 (below knee, cuff suspension interface), L5667 (below knee, above knee, socket insert, suction suspension with locking mechanism) type devices as described by the American Orthotic & Prosthetic Association (AOPA) codes. The crystal gels are useful for making AOPA code devices for upper extremity prosthetics. The devices can be cast molded or injection molded in combination with or without fiber or fabric backing or fiber or fabric reinforcement. When such liners are made without fabric backing, various gels can be used to form gel-gel and gel-gel-gel composites and the like with varying gel rigidities for the different gel layer(s).

Health care devices such as face masks for treatment of sleep disorder require non-tacky invention gels. The invention gel can be used by forming a gel overlap portion on the face cup at its edge conforming to the face and serve to provide comfort and maintain partial air or oxygen pressure when worn on the face during sleep. Although tacky gels can be made from the the invention gels, tacky gels because of its tactile feel are undesirable for such applications as face masks and other prolong skin contact uses.

The invention gels can be formed into gel strands, gel bands, gel tapes, gel sheets, and other articles of manufacture in combination with or without other substrates or materials such as natural or synthetic fibers, multifibers, fabrics, films and the like. Moreover, because of their improved tear resistance and resistance to fatigue, the crystal gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the crystal gels are more tear resistant, they are especially useful for making condoms, toy balloons, and surgical and examination gloves. As toy balloons, the crystal gels are safer because it will not rupture or explode when punctured as would latex balloons which often times cause injures or death to children by choking from pieces of latex rubber. The crystal gels are advantageously useful for making gloves, thin gloves for surgery and examination and thicker gloves for vibration damping which prevents damage to blood capillaries in the fingers and hand caused by handling strong shock and vibrating equipment. Various other gel articles can be made from the advantageously tear resistant gels and gel composites of the inventions include gel suction sockets, suspension belts, The crystal gels are also useful for forming orthotics and prosthetic articles such as for lower extremity prosthesis described below.

Advantageously, the invention gels are non-tacky requires no additive. Its non-tackiness are an inherent property of the glassy A components, and selected (one or more) low viscosity plasticizers forming the invention gels.

The glassy A component type homopolymers can be advantageously added to provide non-tackiness which are selected from one or more homopolymers of: polystyrene, poly(alpha-methylstyrene), poly(o-methylstyrene), poly(m-methylstyrene), poly(p-methylstyrene), and poly (dimethylphenylene oxide). The average molecular weight of the glassy homopolymers advantageously can range from about 2,500 to about 90,000, typical about 3,000; 4,000; 5,000; 6,000; 7,000; 8,000; 9,000; 10,000; 11,000; 12,000, 13,000; 14,000; 15,000; 16,000; 17,000; 18,000; 19,000; 20,000; 30,000; 40,000; 50,000; 60,000; 70,000; 80,000; 90,000 and the like. Example of various molecular weights of commercially available polystyrene: Aldrich Nos.: 32,771-9 (2,500 $M_w$), 32,772-7 (4,000 Mw), 37,951-4 (13,000 Mw), 32-774-3 (20,000 Mw), 32,775-1 (35,000 Mw), 33,034 5 (50,000 Mw), 32,777-8 (90,000 Mw); poly(alpha-methylstyrene) #41,794-7 (1,300 Mw), 19,184-1 (4,000 Mw); poly(4methylstyrene) #18,227-3 (72,000 Mw), Endex 155, 160, Kristalex 120, 140 from Hercules Chemical, GE: Blendex HPP820, HPP822, HPP823, and the like. Various glassy phase associating resins having softening points above about 120° C. can also serve to increase the glassy phase of the Crystal gels of the invention and met the non-tackiness criteria, these include: Hydrogenated aromatic resins (Regalrez 1126, 1128, 1139, 3102, 5095, and 6108), hydrogenated mixed aromatic resins (Regalite R125), and other aromatic resin (Picco 5130, 5140, 9140, Cumar LX509, Cumar 130, Lx-1035) and the like.

On the other hand, the molten gelatinous elastomer composition will adhere sufficiently to certain plastics (e.g. acrylic, ethylene copolymers, nylon, polybutylene, polycarbonate, polystyrene, polyester, polyethylene, polypropylene, styrene copolymers, and the like) provided the temperature of the molten gelatinous elastomer composition is sufficient high to fuse or nearly fuse with the plastic. In order to obtain sufficient adhesion to glass, ceramics, or certain metals, sufficient temperature is also required (e.g. above 250° F.). Commercial resins which can aid in adhesion to materials (plastics, glass, and metals) may be added in minor amounts to the gelatinous elastomer composition, these resins include: Super Sta-tac, Nevtac, Piccotac, Escorez, Wingtack, Hercotac, Betaprene, Zonarez, Nirez, Piccolyte, Sylvatac, Foral, Pentalyn, Arkon P, Regalrez, Cumar LX, Picco 6000, Nevchem, Piccotex, Kristalex, Piccolastic, LX-1035, and the like.

The commercial resins which can aid in adhesion to materials (plastics, glass, and metals) may be added in minor amounts to the gelatinous elastomer composition, these resins include: polymerized mixed olefins (Super Sta-tac, Betaprene Nevtac, Escorez, Hercotac, Wingtack, Piccotac), polyterpene (Zonarez, Nirez, Piccolyte, Sylvatac), glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035), and the like. More earlier, I had also disclosed the use of liquid tackifiers in high viscosity SEBS gets.

The incorporation of such adhesion resins is to provide strong and dimensional stable adherent crystal gels, gel composites, and gel articles. Typically such adherent crystal gels can be characterized as adhesive gels, soft adhesives or adhesive sealants. Strong and tear resistant adherent crystal gels may be formed with various combinations of substrates or adhere (attach, cling, fasten, hold, stick) to substrates to form adherent crystal gel/substrate articles and composites.

Furthermore, the $M_n$ materials in contact with the gel of the invention may be made from flexible materials, such as fibers and fabrics of cotton, flax, and sill Other flexible materials include: elastomers, fiber-reinforced composites, mohair, and wool. Useful synthetic fibers include: acetate, acrylic, aremid, glass, modacrylic polyethylene, nylon, olefin, polyester, rayon, spandex, carbon, sufar, polybenzimidazole, and combinations of the above. Useful open-cell plastics include: polyamides, polyimides, polyesters, polyisocyanurates, polyisocyanates, polyurethanes, poly(vinyl alcohol), etc. Open-celled Plastic (foams) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference. These include: open and non-opened cell silicone, polyurethane, polyethylene, neoprene, polyvinyl chloride, polyimide, metal, ceramic, polyether, polyester, polystyrene, polypropylene. Example of such foams are: Thanol®, Arcol®, Ugipol®, Arcel®, Arpak®, Arpro®, Arsan®, Dylite®, Dytherm®, Styrofoam®, Trymer®, Dow Ethafoam®, Ensolite®, Scotfoam®, Pyrell®, Volana®, Trocellen®, Minicel®, and the like.

Sandwiches of gel-material (i.e. gel-material-gel or material-gel-material, etc.) are useful as dental floss, shock absorbers, acoustical isolators, vibration dampers, vibration isolators, and wrappers. For example the vibration isolators can be use under research microscopes, office equipment, tables, and the like to remove background vibrations. The tear resistance nature of the instant gels are superior in performance to triblock copolymer gels which are much less resistance to crack propagation caused by long term continue dynamic loadings.

Adhesion to substrates is most desirable when it is necessary to apply the adherent crystal gels to substrates in the absence of heat or on to a low temperature melting point substrate for later peel off after use, such as for sound damping of a adherent crystal gel composite applied to a first surface and later removed for use on a the same or second surface. The low melting substrate materials which can not be exposed to the high heat of the molten adherent crystal gels, such as low melting metals, low melting plastics (polyethylene, PVC, PVE, PVA, and the like) can only be formed by applying the adherent crystal gels to the temperature sensitive substrates. Other low melting plastics include: polyolefins such as polyethylene, polyethylene copolymers, ethylene alpha-olefin resin, ultra low density ethylene-octene-1 copolymers, copolymers of ethylene and hexene, polypropylene, and etc. Other cold applied adherent crystal gels to teflon type polymers: TFE, PTFE, PEA, FEP, etc., polysiloxane as substrates are achieved using the adherent crystal gels of the invention.

Likewise, adherent crystal gel substrate composites can be both formed by casting hot onto a substrate and then after cooling adhering the opposite side of the adherent crystal gel to a substrate having a low melting point. The adherent crystal gel is most essential when it is not possible to introduce heat in an heat sensitive or explosive environment or in outer space. The use of solid or liquid resins promotes adherent crystal gel adhesion to various substrates both while the adherent crystal gel is applied hot or at room temperature or below or even under water. The adherent crystal gels can be applied without heating to paper, foam, plastic, fabric, metal, concrete, wood, wire screen, refractory material, glass, synthetic resin, synthetic fibers, and the like.

The adhesion properties of the gels are determined by measuring comparable rolling ball tack distance "D" in cm using a standard diameter "d" in mm stainless steel ball rolling off an inclined of height "H" in cm and determining the average force required to perform 180° C. peel of a heat formed $G_1M_1$ one inch width sample applied at room temperature to a substrate $M_2$ to form the composite $M_1G_1M_2$ The peel at a selected standard rate cross-head separation speed of 25 cm/minute at room temperature is initiated at the $G_1M_2$ interface of the $M_1G_1M_2$ composite, where the substrate $M_2$ can be any of the substrates mentioned and $M_1$ preferably a flexible fabric.

Advantageously, glassy phase associating homopolymers such as polystyrene and aromatic resins having low molecular weights of from about 2,500 to about 90,000 can be blended with the triblock copolymers of the invention in large amounts with or without the addition of plasticizer to provide a copolymer-resin alloy of high impact strengths. More advantageously, when blended with multiblock copolymers and substantially random copolymers the impact, strengths can be even higher. The impact strength of blends of from about 150 to about 1,500 parts by weight glass phase associating polymer and resins to 100 parts by weight of one or more multiblock copolymers can provide impact strength approaching those of soft metals. At the higher loadings, the impact strength approaches that of polycarbonates of about 12 ft-lb/in notch and higher.

The improvements of the crystal gels of the invention is exceptional, the crystal gels are crystal to the touch and can be quantified using a simple test by taking a freshly cut Crystal gel probe of a selected gel rigidity made from the crystal gels of the invention. The crystal gel probe is a substantially uniform cylindrical shape of length "L" of at least about 3.0 cm formed components (1)–(3) of the crystal gels of the invention in a 16×150 mm test tube. The crystal gel probe so formed has a 16 mm diameter hemispherical tip which (not unlike the shape of a human finger tip) is brought into perpendicular contact about substantially the center of the top cover of a new, un-touched polystyrene reference surface (for example the top cover surface of a sterile polystyrene petri dish) having a diameter of 100 mm and a weight of 7.6 gram resting on its thin circular edge (which minimizes the vacuum or partial pressure effects of one flat surface in contact with another flat surface) on the flat surface of a scale which scale is tared to zero. The probe's hemi-spherical tip is place in contact with the center of the top of the petri dish cover surface and allowed to remain in contact by the weight of the gel probe while held in the upright position and then lifted up. Observation is made regarding the probe's tackiness with respect to the clean reference polystyrene surface. For purpose of the foregoing reference tack test, tackiness level 0 means the polystyrene dish cover is not lifted from the scale by the probe and the scale shows substantially an equal positive weight and negative weight swings before settling again back to zero with the swing indicated in (negative) grams being less than 1.0 gram. A tackiness level of one 1, means a negative swing of greater than 1.0 gram but less than 2.0 gram, tackiness level 2, means a negative swing of greater than 2 gram but less than 3 gram, tackiness level 3, means a negative swing of greater than 3 gram but less than 4 gram, before settling back to the zero tared position or reading. Likewise, when the negative weight swing of the scale is greater than the weight of the dish (i.e., for the example referred above, greater than 7.6 gram), then the scale should correctly read −7.6 gram which indicates the dish has completely been lifted off the surface of the scale. Such an event would demonstrate the tackiness of a gel probe having sufficient tack on the probe surface. The crystal gels of the invention fails to lift off the polystyrene reference from the surface of the scale when subject to the foregoing reference tack test. Advantageously, the crystal gels of the invention can register a tackiness level of less than 5, more advantageously, less than 3, still more advantageously, less than 2, and still more advantageously less than 1. The non-tackiness of the crystal gels of the invention can advantageously range from less than 6 to less than 0.5 grams, typical tack levels are less than 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5, 2.8, 3.0, 3.5, 4.0, 4.5, 5.0 grams and the like. Whereas probes of gels made from amorphous gels such as SEPS, SEBS, S-EP-EB-S, and the like with copolymer styrene to rubber ratio of less than 37:63 and plasticizer of higher than 30 cSt 40° C. are found to lift the polystyrene reference from the surface of the scale. For purposes of indicating tack, the method above can provide gel tack level readings of 1, 2, 3, 4, 5, 6, and 7 grams. More accurate and sensitive readings can be made using electronic scales of tack levels of less than 1 gram. By this simple method tack levels (of a gel probe on a polystyrene reference surface) can be measure in terms of gram weight displacement of a scale initially tared to zero. For purpose of the present invention the method of using a polystyrene reference surface having a weight of 7.6 grams in contact and being lifted by the tackiness of a cylindrical gel probe having a 16 mm diameter hemi-spherical tip is used to determine the tackiness of the crystal gels of the invention. The level of tack being measured in gram Tack at 23° C.

The gels are prepared by blending together the components including the various additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of multiblock copolymers (I) and polymer (II) used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The gels of the invention can also contain gases as an additive, i.e. the gel can be foamed. Foam is herein defined as tightly or loosely packing aggregation of gas bubbles, separated from each other by thin or thick layers of gel. Many types of foamed gels (from ultra high density to ultra low density) can be produced as desired by (i) adding gas to the molten gel during processing, and (ii) producing gas in the molten gel during processing. Gas can be added by whipping a gas into the molten gel before it cools or introduce a gas into the molten gel and then expand or reduce the size of the gas bubbles by reducing the pressure to reduce the bubbles size or applying high pressure to expand the bubbles size. In this regard, inert gases such as Carbon dioxide, Nitrogen, Helium, Neon, Argon, Krypton, Xenon and Radon are suitable. Air can also be used. Gas can be produced in the molten gel by adding one or more of a "blowing agent" to the. Useful blowing agents include dinitroso compounds, such as dinitroso pentamethylene-tetramine, azodicarbonamide, 4,4'oxybis (benzenesulfonyl) hydrazine, 5-phenyltetrazole, p-toluenesulfonyl semicarbazide, sulfonyl hydrazide, such as benzene sulfonylhydrazide. Water can be used as a "blowing agent" to [1] produce varying density of foam gels; water used to advantage can be in the form of mist, droplets, steam, and hot or cold water. The density of the foam gels can vary from less than 1.00 kilograms per cubic meter to near the solid gel density. Although the materials forming soft solid gels may be more shear resistant, the same materials when made into a foam become much less shear resistant.

The gel articles can be formed by blending, injection molding, extruding, spinning, casting and other conventional methods. For example, Shapes having various cross-section can be extruded using a HP-2000 Mixing extruder from Dek-tron Scientific Instruments of Plainfield, N.J. 07060, USA.

The high glassy component copolymers suitable for use in forming the crystal gels of the invention include high styrene component BASF's Styroflex series copolymers including BX 6105 with a statistical SB sequence for the low elastomeric segments (styrene to butadiene ratio of 1:1) and an overall styrene content of almost 70%, high styrene content Shell Kraton G, Kraton D-1122X (SB)n, D-4122 SBS, D-4240 (SB)n, D-4230 (SB)n, DX-1150 SBS, D-4140 SBS, D-1115 SBS, D-4222 SBS, Kraton D-1401P, SEBS, Dexco's Vector 6241-D, 4411-D, Fina's Finaclear high styrene content SBS series copolymers, Phillips Petroleum's XK40 K-Resin styrene/butadiene copolymers, Kuraray's S2104 SEPS. The copolymers include amorphous polymers with high styrene content: SBS, SIS, SEPS, SEB/EPS, and the like. The (i–viii) copolymers with glassy to elastomeric ratios can range from 37:63, 37.6:62.4, 38:62, 39:61, 40:60, 41:59, 42:58, 43:57, 44:65, 45:55, 46:54, 47:53, 48:52, 49:51, 50:50, 51:49 52:48, 53:47, 54:46, 55:45, 56:44, 57:43, 58:42, 59:41, 60:40, 6:39, 62:38, 63:37, 64:36, 65:35, 66:34, 67:33, 68:32, 69:31, 70:30, 7:29, 72:28, 73:27, 74:26, 75:25, 76:24, 77:23, 78:22, 79:21, to 80:20 and higher. High styrene content Dow ES30, and ES44 with styrene wt % of 15.7, 23.7, 273, 28.1, 39.6 & 43.9 respectively, M copolymers (ES53, ES58, ES62, ES63, and ES69 with styrene wt % of 52.5, 58.1, 62.7, 62.8, and 69.2 respectively and crystallinity, %, DSC, based on copolymer of 37.5, 26.6, 17.4, 22.9, 19.6 and 5.0 respectively, S copolymers ES72, ES73, and ES74 with styrene wt % of 72.7, 72.8, and 74.3 respectively may also be used. These hard to process polymers can be added (from 0.01 to 30% weigh basis of polymers) by dry blending in combination with 200–400 parts oil and multiblock copolymers such as SEEPS 4055, 4033, 4077, 4045 and the like and extruded at about between 75° C.–135° C. to form a preblend and then formulated with additional oil or/or oil and polymers to produce the final crystal gels of the invention.

Suitable polyolefins include polyethylene and polyethylene copolymers such as Dow Chemical Company's Dowlex 3010, 2021D, 2038, 2042A, 2049, 2049A, 2071,2077, 2244A, 2267A; Dow Affinity ethylene alpha-olefin resin PL-1840, SE-1400, SM-1300; more suitably: Dow Elite 5100, 5110, 5200, 5400, Primacor 141-XT, 1430, 1420, 1320, 3330, 3150, 2912, 3340, 3460; Dow Attane (ultra low density ethylene-octene-1 copolymers) 4803, 44801, 4602, Eastman Mxsten CV copolymers of ethylene and hexene (0.905–0.910 g/cm3).

The gels can also be formed directly into articles or remelted in any suitable hot melt applicator and extruded into shaped articles and films or spun into threads, strips, bands, yarns, or other shapes using a tubing header, multi-strand header, wire coating header, and the like. With respect to various shapes and yarn, its size are conventionally measured in denier (grams/9000 meter), tex (grams/1000 meter), and gage (1/2.54 cm). Gage, tex, denier can be converted as follows: tex=denier/9=specific gravity (2135/gage), for rectangular cross section, tex=specific gravity·(5806×103)(th)(w)/9, where th is the thickness and w the width of the strip, both in centimeters. General descriptions of (1) block copolymers, (2) elastomeric fibers and conventional (3) gels are found in volume 2, starting at pp. 324–415, volume 6, pp 733–755, and volume 7, pp. 515 of *ENCYCLOPEDIA OF POLYMER SCIENCE AND ENGINEERING,* 1987 which volumes are incorporated herein by reference.

The instant gels is excellent for cast molding and the molded products have various excellent characteristics which cannot be anticipated form the properties of the raw components. Other conventional methods of forming the composition can be utilized.

In general, the basis of this invention resides in the fact that one or more of a high viscosity linear multiblock and star-shaped multiblock copolymers (I) or a mixture of two or more of such copolymers having (A) end block to elastomeric block ratio preferably within the contemplated range of styrene to rubber ratios of from about 20:80 to about 40:60 and higher, more preferably from between about 31:69 to about 40:60 and higher when blended in the melt with an appropriate amount of plasticizing oil makes possible the attainment of gels having a desirable combination of physical and mechanical properties, notably high elongation at break of at least 1,600%, ultimate tensile strength of about $8\times10^5$ dyne/cm$^2$ and higher, low elongation set at break of substantially not greater than about 2%, tear resistance of $5\times10^5$ dyne/cm$^2$ and higher, substantially about 100% snap back when extended to 1,200% elongation, and a gel rigidity of substantially from about 2 gram to about 1,800 gram Bloom and higher.

More specifically, the gels of the present invention exhibit one or more of the following properties. These are: (1) tensile strength of about $8\times10^5$ dyne/cm$^2$ to about $10^7$ dyne/cm$^2$ and greater; (2) elongation of less than about 1,600% to about 3,000% and higher, (3) elasticity modulus of about $10^4$ dyne/cm$^2$ to about $10^6$ dyne/cm$^2$ and greater; (4) shear modulus of about $10^4$ dyne/cm$^2$ to about $10^6$ dyne/cm$^2$ and greater as measured with a 1, 2, and 3 kilogram load at 23° C.; (5) gel rigidity of about less than about 2 gram Bloom to about 1,800 gram Bloom and higher as measured by the gram weight required to depress a gel a distance of 4 mm with a piston having a cross-sectional area of 1 square cm at 23° C.; (6) tear propagation resistance of at least about $5\times10^5$ dyne/cm$^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The gel articles molded from the instant compositions have various additional important advantages in that they do not crack, creep, tear, crack, or rupture in flexural, tension, compression, or other deforming conditions of normal use; but rather the molded articles made from the instant composition possess the intrinsic properties of elastic memory enabling the articles to recover and retain its original molded shape after many extreme deformation cycles. In applications where extreme tear resistance, low rigidity, high elongation, good compression set and excellent tensile strength are important, the instant gels would be advantageous.

The gels of the present invention are useful in low frequency vibration applications, such as viscoelastic layers in constrained-layer damping of mechanical structures and goods, as viscoelastic layers used in laminates for isolation of acoustical and mechanical noise, as ant-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components. The compositions are also useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses include various shaped articles as toys, optical uses (e.g. cladding for cushioning optical fibers from bending stresses) and various optical devices, as lint removers, dental floss, as tips for swabs, as fishing bait, as a high vacuum seal (against atmosphere pressure) which contains a useful amount of a mineral oil-based magnetic fluid particles, etc. Moreover, the casted, extruded, or spun threads, strips, yarns, tapes can be weaved into cloths, fine or coarse fabrics.

The instant compositions can be formed in any shape; the original shape can be deformed into another shape (to contact a regular or irregular surface) by pressure and upon removal of the applied pressure, the composition in the deformed shape will recover back to its original shape.

As an example of the versatility of use of the instant gels, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming the composition into a selected shape matching the contours of the specific body part or body region. The composition can be formed into any desired shaped, size and thickness suitable as a cushion; the shaped composition can be additionally surrounded with film, fabric, foam, or any other desired material or combinations thereof. Moreover, the composition can be casted onto such materials, provided such materials substantially maintain their integrity (shape, appearance, texture, etc.) during the casting process. The same applies for brace cushions for the hand, wrist, finger, forearm, knee, leg, etc.

Other uses include self closing or self tightening enclosures for splicing electrical and telephone cables and wires. For example, the gels can be preformed into a small diameter tubing within an outer elastic tubing, both the internal gel tubing and external elastic tubing can be axially expanded and fixed in place by a removable continuous spiral retainer. Upon insertion of a spliced pair or bundle of cables or wires, the spiral retainer can be removed, as the retainer is removed, the gel and elastic tubing impinges onto the inserted cables or wires splices, thereby sealing the electrical splices against weather, water, dirt, corrosives and shielding the splice from external abuse. The enclosure is completed without the use of heat or flame as is conventionally performed. In the case of multiblock copolymer (I) 'treated" gels exhibiting delay recovery or long relaxation times and having extreme tear resistance, a tape of such a gel can be used to wrap the area of a spliced pair or bundle of cable or wire by extending the gel tape and wrapping it around the splice. The delayed recovery of the gel is important in that when the splice is fully wrapped and the gel tape end is let go, it will not quickly unravel itself. This allows time to fix in place an outer elastic shelve around the gel tape wrapped area. Thus, the gel tape will eventually fully recover around the spliced area gradually developing a strong radial recovery force about the spliced area so as to prevent the entry of water, dirt, and other contaminations. Triblock copolymer gels do not have adequate tear strength and have too rapid a recovery to allow time for placement of an outer elastic shelve.

As the treated gels and gels formed from multiblock copolymers (I) having more and more midblock polymer chains can be expected to exhibit greater delay recovery form extension or longer relaxation times with increasing number of midblocks and increasing midblock lengths, such gels having more than three midblocks forming the copolymers (I) can exhibit extreme tear resistance and excellent tensile strength while at the same time exhibit almost liquid like properties. For example, a fun toy can be made from (S-E-EB-ES), (S-B-EB-EB-S), (S-E-EP-E-EP-S), (S-P-EB-P-EB-S), (S-E-EB-E-EB-E-S), (S-E-EP-E-EP-E-EP-E-S), (S-E-EP-EP)$_n$, (S-B-EP-E-EP)$_n$, (S-E-EP-FEP-E)$_n$, (S-E-EB-E-EB-E-EB-E-EB-S)$_n$ copolymer gels which are molded into cube shapes when placed on the surface of a incline will collect it self together and flow down the incline as a moving body much like a volume of water moving on a high surface tension surface. This is due to the greater distance between the end block (A) domains. Such liquid like performing gels can be very strong and exhibit extreme tear resistance as exhibited by gels made from (S-E-EP-S) multiblock copolymer gels with shorter (A) distance between domains. Such liquid like gels when shaped into a cube will be deformed by the force of gravity on Earth, but will retain its memory and regain to its molded cube shape when released in outer space or reform into a cube if let loose in a container of liquid of equal density. As a comparison, such a toy formed in the shape of a large cube from a high viscosity triblock copolymer with a plasticizer content of 1:1,600 parts will be flattened by the force of gravity and run down an incline, but is very fragile and will start to tear if attempt is made to pick it up by hand. This is an excellent comparison of the difference of tear resistance difference between triblock copolymer gels and multiblock copolymer gels. A useful application is to use such an elastic liquid gel volume to fill a container or to encapsulate an electrical or electronic component in a container filling every available space, when needed, the shapeless gel volume can be removed by pouring it out of the container whole.

The most surprising, unexpected, versatile use of the composition is dental flossing. The dental floss can be almost any shape so long as it is suitable for dental flossing. A thick shaped piece of the composition can be stretched into a thin shape and used for flossing. A thinner shaped piece would require less stretching, etc. For purposes of dental flossing, while flossing between two closely adjacent teeth, especially between two adjacent teeth with substantial contact points and more especially between two adjacent teeth with substantial amalgam alloy metal contact points showing no gap between the teeth, it is critical that the gel resist tearing, shearing, and crazing while being stretched to a high degree in such situations. For example, dental gel floss can take the form of a disk where the segments of the circumference of the disk is stretched for flossing between the teeth. Other shaped articles suitable for flossing include threads, strips, yarns, tapes, etc., mentioned above.

In order for gels to be useful as a dental floss, it must overcome the difficult barriers of high shearing and high tearing under extreme elongation and tension loads. The difficulties that the gels must overcome during flossing can be viewed as follows: during the action of flossing, the gel is stretched from no less than about 200% to about 1,100% or higher, the gel floss is deformed as it is pulled down with tearing action between the contacting surfaces of the teeth, then, the wedge of gel floss is sheared between the inner contacting surfaces of the teeth, and finally, the elongated wedged of gel floss is pulled upwards and out between the surfaces of the teeth. The forces encountered in the act of flossing are: tension, shearing, tearing under extreme tension.

This invention advances the flossing art by providing strong, soft, and extreme tear resistant gels made from multiblock copolymers which gels are substantially as soft as the gums surrounding the teeth.

Gel floss formed from the gels has many advantages over conventional dental floss such as regular and extra fine waxed and unwaxed nylon floss, spongy nylon fiber floss, and waxed and unwaxed expanded and unexpended teflon floss. Such conventional floss are not recommended for use by children, since a slip or sudden snap in forcing the floss between the teeth may cause injury to the gums which often times results in bleeding. For sensitive gums and inflamed gums which has become red and puffy, it is difficult to floss at, near, and below the gumline. The soft gel floss with softness substantially matching the softness of the gums are of great advantage for use by children and for flossing teeth surrounded by sensitive and tender gums.

The shear resistant characteristics of the gels can be indirectly determined by subjecting the gel to the shear forces of a pair of twisting strings and the resulting inward pulling forces of the twisting strings can be directly read off of a spring scale. As a pair of strings are gradually twisted, typical values will range from less than one pound to fifty pounds and greater. As the string is being twisted (simulating increased shearing forces), the measured pulling forces can range from a low value of 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 . . . to values of 40, 50, 60, 70, 80 pounds and greater.

Gel material of low strength can not resist the tremendous shearing action of the twisting strings. The twisting action of the strings can exhibit a first order twist, a second order twist, or higher order twists. A first order twist refers to one or more twists of a pair of strings (i.e. a pair of strings when twisted together forms a small tight binding helix). A second order twist refers to one or more large binding helixes build up by a pair of strings that have been twisted beyond the maximum-number of twist which normally produce small tight binding helixes of the first order kind. Similarly, a third order twist refers to a much larger tightly binding helix build up by the maximum number of second order twists produced by the pair of twisting strings. The third order twist may be manifested by the appearance of a branch of two or more twist of the first order twisting strings.

The order of twisting will increase (from a one, two, three, and higher order twist) until the rubber band breaks. Likewise, a looped string with one end attached to a spring scale and the other end attached to a fixed anchor can be twisted into a first, second, third, and higher ordered twist state. This method can be utilized to directly measure the force generated for each ordered twist states. The static force generated by twisting a string on a spring scale is a way of determining the shear force generated in the shearing action of forcing the gel floss between two closely contacting teeth when flossing.

In considering dental flossing criteria, one or more of the following conditions can be regarded as critical factors for dental flossing gels.

Shear Resistant Criteria

For the gels to be considered useful for flossing, the gels, critically, can withstand a twisting string shearing force of at least about 5 Kg, more advantageously at least about 8 Kg, and still more advantageously at least about 10 Kg of inward pulling force of a pair of twisting strings measured directly on a spring scale.

Flossing Cycle Criteria

For the gels to be considered useful for flossing, the gels, critically, can advantageously be able to perform at least 4 flossing cycles, more advantageously 8 cycles, and still more advantageously of about 20 cycles without breaking apart when a 3.0 mm diameter gel strand is tested on a set of simulated upper front teeth fully contacting under a uniform spring load of (0.9027 Kg) two pounds. The simulated upper front teeth comprises two small stainless steel rollers (⅜" dia.) facing lengthwise parallel and forced together so as to form a contact length of ½ inches under a spring load of two pounds as measured by a Entran® model ELO-200-4 load cell adjusted by a straight micrometer at room temperature.

Gel Strength Criteria

For the gels to be considered useful for flossing, the gels, critically, can advantageously exhibit a tensile strength of at least 5 $Kg/cm^2$ (when extended to break as measured at 180° U bend around a 5.0 mm mandrel attached to a spring scale) and more advantageously at least 8 $Kg/cm^2$, and still more advantageously of about 10 $Kg/cm^2$ and higher. The high and gels useful as dental floss can exhibit tensile strengths at break of at least 20 $Kg/cm^2$, more advantageously of at least 40 $Kg/cm^2$, and exceptionally more advantageously at least 60 $Kg/cm^2$. Typically, the tensile strengths range from about 20 $Kg/cm^2$ to about 110 Kg/cm2 and higher, more typically from about 30 $Kg/cm^2$ to 80 $Kg/cm^2$ and higher, especially more typically from about 40 $Kg/cm^2$ to about 90 $Kg/cm^2$ and higher, and exceptionally typically from about 50 $Kg/cm^2$ to about 100 $Kg/cm^2$ and higher.

Propagating Tear Criteria

As a minimum, for the Gets to be considered useful for flossing, the gels, critically, can advantageously exhibit a propagating tear force (when propagating a tear as measured at 180° U bend around a 5.0 mm diameter mandrel attached to a spring scale) of at least about 1 Kg/cm, more advantageously at least 2 Kg/cm, and still more advantageously of about 3 Kg/cm and higher. The gels useful as dental floss can exhibit tear strengths of at least 4 Kg/cm and higher, more advantageously of at least 6 Kg/cm and higher, exceptionally more advantageously of at least 8 Kg/cm and higher. Typically, the tear propagation strength can range from about 5 Kg/cm to about 20 Kg/cm and higher, more typically from about less than 5 Kg/cm to about 25 Kg/cm and higher, especially more typically form about less than 6 Kg/cm to about 30 Kg/cm and higher, and exceptionally more typically from about less than 8 Kg/cm to about 35 Kg/cm and higher.

For the Gels to be considered useful for flossing, the gels, critically, can advantageously exhibit a propagating tension tear force (when a cylindrical sample is notched and a tear is initiated at the notched area and propagated past its maximum cylindrical diameter by length-wise stretching of the cylindrical sample) of at least about 1 Kg/cm, more advantageously at least 2 Kg/cm, and still more advantageously of about 4 Kg/cm and higher. The extreme tear resistant gels typically will exhibit even higher tension tear values.

Rigidity Criteria

The rigidities of the extreme tear resistant useful for flossing can advantageously range from about 350 gram to about 1,800 gram Bloom, more advantageously from about 400 gram to about 1,500 gram Bloom, especially more advantageously from about 450 gram to about 1,200 gram Bloom, still more advantageously from about 450 gram to about 1,000 gram Bloom, and less advantageously at values of greater than 1,800 gram Bloom.

In general, as a minimum, the flossing gels can exhibit several critical properties, including advantageously the ability to:

(1) withstand a shearing force of at least about 5 Kg under the string twisting test described above, (2) perform at least 4 flossing cycles without breaking apart when tested on a set of simulated upper front teeth fully contacting under a uniform spring load of two pound, (3) exhibit a tensile strength of at least 5 $Kg/cm^2$ and higher, (4) exhibit a propagating tear force at 180° U bend tear test of at least about 1 Kg/cm, and (5) exhibit a propagating tension tear force (on a notched cylindrical sample) of at least about 1 Kg/cm.

For use as a dental floss, the gel is made (by extruding, spinning, casting, etc) as a continuous gel strand, the gel strand can be in the shape of a fiber of a selected diameter (from less than about 0.15 to about 5.0 mm and greater) as a continuous tape having a selected width and thickness (less than 0.10 mm thin to about 5.0 mm and thicker) or in any desired shape suitable for flossing. The fiber, tape or a selected shape is then cut to a desired length, rolled up and placed into a dispenser suitable for containing and dispensing a measured use amount of gel floss. The continuous fiber and tape can be partly cut or notched for measured single or multiple use. When the floss is pulled from the dispenser to a point showing the notched or cut mark on the length of gel floss, the lid is pushed down on the gel floss nipping it and allowing the floss to be further pulled and separated at the notched or cut point. Additionally, a suitable floss dispenser containing a measured length of gel floss can be fitted with a cutting edge attached to its lid or on its body and the uncut and un-notched gel floss can be dispensed from the dispensing container and cut at the desired measured use length by pressing close the dispenser cutting edge down on the floss so as to nip and cut the gel or by simply closing the dispenser lid or running the gel along the cutting edge on the dispenser body separating a useful length of gel floss.

In practice, typically during flossing, a gel strand will under go various deformations, some of these deformations can be measured, including original shape, extended shape under tension, nipping force, and nipped deformation under a measured force and width. Typically, any shaped gel strand can be used for flossing, a square cross-section, a circular cross-section, a rectangular cross-section, round, oval, etc. For example, a 235 mm diameter strand when extended under a force of 2.5 kg can be nipped down to 0.14 mm thickness (along a 3 mm uniform width of its cross-section) by a force of 0.9072 Kg (2.0 pound force), a reduction of 16.78:1; a 1.89 mm diameter strand when extended under a force of 2.5 kg can be nipped down to 0.14 mm thickness by a force of 0.9072 Kg (2.0 pound force), a reduction of 135:1; a 2.75 mm diameter strand when extended under a force of 2.5 kg can be nipped down to 0.19 mm thickness by a force of 0.9072 Kg (2.0 pound force), a reduction of 14.4:1; and a 2.63 mm diameter strand when extended under a force of 25 kg can be nipped down to 0.19 mm thickness by a force of 0.9072 Kg (2.0 pound force), a reduction of 13.8:1. the cross-section of the gel floss can be reduced to any degree by stretching and nipping (from less than about 1% to about 1,600% and higher). Advantageously, a gel having the required strength, tear resistance, gel rigidity, and other characteristics described can be formed into a floss of any selected cross-section and thickness provided the floss is capable of being stretched when flossing under tension without breaking. Typically the stretching or pulling force is from about less than 0.1 Kg to about 3 Kg and higher. The cross-section of the strand of gel floss can be capable of being nipped by a 0.9027 Kg (2 pounds) force applied across a width of 3 mm from its original cross-sectional dimensions to a nipped thickness of about 3.0 mm to about 0.02 mm and lower, more advantageously from about 2.5 mm to about 0.04 mm and lower, still more advantageously from about 2.0 mm to about 0.08 mm and lower; especially advantageously from about 15 mm to about 0.15 mm and lower; especially more advantageously from about 1.2 mm to about 0.20 mm and lower; especially still more advantageously from about 1.0 mm to about 0.25 mm and lower.

The gels made from higher viscosity copolymers (I) are resistant to breaking when sheared than triblock copolymer gels. This can be demonstrated by forming a very soft gel, for example 100 parts copolymer to 800 parts plasticizing oil. The soft gel is cut into a strip of 25 cm×25 cm cross-section, the gel strip is gripped lengthwise tightly in the left hand about its cross-section and an exposed part of the gel strip being gripped lengthwise around its cross-section tightly by the right hand as close to the left hand as possible without stretching. With the two hands gripping the gel strip's cross-section, the hands are moved in opposite directions to shear apart the gel strip at its cross-section. The shearing action by the gripping hands is done at the fastest speed possible as can be performed by human hands. The shearing action is performed at a fraction of a second, possible at about 0.5 seconds. Using this demonstration, the copolymer (I) gels will not easily break completely apart as would gels formed from triblock copolymers. In some cases, it will take two, three, or more attempts to shear a high viscosity copolymer (I) gel strip this way. Whereas, a lower viscosity triblock copolymer gel strip can be sheared apart on the first try. For gels made from copolymers with viscosities of 5 wt % solution in Toluene, their shear resistance will decrease with decreasing viscosity. For example, the shear strengths as tested by hand shearing described above of gels made from copolymers having viscosities of 150, 120, 110, 105, 95, 90, 89, 85, 70, 60, 58, 48, 42, 40, 35, 28, 27, 25, 21 cps, and the like can be expected to decrease with decreasing viscosity.

The tensile strengths of multiblock copolymer gels made from higher viscosity copolymers (1) can be slightly lower than or equal to the tensile strengths of gels made from lower solution viscosity triblock copolymers (II).

Strands of gels comprising higher viscosity multiblock copolymers will perform better than gel strands made from gels of lower viscosity triblock copolymers when used in flossing amalgam molars and more than three times better when used in flossing front teeth.

Gels, in general, will exhibit higher tensile and greater tear resistance than their parent gels containing higher concentrations of plasticizer.

As compared to spongy nylon, regular waxed nylon, and extra fine unwaxed nylon when flossing amalgam molars, the performance of multiblock copolymer gels are on the average substantially better.

While advantageous components and formulation ranges based on the desired properties of the multiblock copolymer gels have been disclosed herein. Persons of skill in the art can extend these ranges using appropriate material according to the principles discussed herein. All such variations and deviations which rely on the teachings through which the present invention has advanced the art are considered to be within the spirit and scope of the present invention.

The invention is further illustrated by means of the following illustrative embodiments, which are given for purpose of illustration only and are not meant to limit the invention to the particular components and amounts disclosed.

Comparisons of oil extended multiblock copolymers have been described in Shell Chemical Company Technical Bulletin SC:1102-89 (April 1989) "KRATON®THERMOPLASTIC RUBBERS IN OIL GELS" which is incorporated herein by reference.

EXAMPLE I

Gels of 100 parts of Kraton G1651, Kuraray Septon 2006 (SEPS), Kuraray Septon 8006 (SEBS), a high viscosity $(SEB)_n$, and a high viscosity $(SEP)_n$ triblock copolymers and 1,600, 1,200, 1,000, 800, 600, 500, 450, and 300 parts by weight of Duroprime 200 white oil are melt blended and samples extruded (from a 7.15 mm diameter orifice) into selected lengths of varying diameters for use as dental floss, the bulk gel rigidities is found to be within the range of 2 to 1,800 gram Bloom, the tensile strength is found to decrease with increase orientation, and the optimum tensile strength found for gel samples with the least amount of stress or orientation imparted during cool from the molten state to room temperature.

EXAMPLE II

Example I is repeated using Kuraray (S-E-EP-S) 4055 and 4077 multiblock copolymers, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I. The tensile strength is found to decrease with increase orientation, and the optimum tensile strength found for gel samples with the least amount of stress or orientation imparted during cool from the molten state to room temperature.

EXAMPLE III

Example I is repeated using (S-E-EP-S), (S-E-EP-E-S), (S-B-EP-S), (S-E-EB-S), (S-EB-EP-S), (S-E-EP-EB-S), (S-B-EB-S), (S-E-EB-ES), (S-B-EP-E-S), (S-B-EB-E-S), (S-B-EP-B-S), (S-B-EB-B-S), (S-E-E-EP-S) (S-E-E-EB-S), (S-B-E-EP-S), (S-B-E-EB-S), (S-B-B-EP-S), (S-B-B-EB-S), (S-E-B-EB-S), (S-E-B-EP-S), (S-EB-EB-S), (S-EP-EP-S), (S-E-EB-EB-S), (S-E-EP-EP-S), (S-E-EB-EP-S), (S-B-EB-EB-S), (S-B-EP-EP-S), (S-B-EB-EP-S), (S-B-EP-EB-S), (S-E-EP-E-EP-S), (S-E-EB-E-EB-S), (S-E-EP-E-EB-S), (S-B-EP-B-EP-S), (S-B-EB-B-EB-S), (S-B-EB-B-EP-S), (S-B-EB-E-EB-S), (S-B-EP-E-EP-S), (S-(EB-B-EP-S), (S-E-EP-B-EB-S), (S-P-EB-S), (S-P-EP-S), (S-P-EP-P-S), (S-P-EB-P-S), (S-B-EP-P-S), (S-B-EB-P-S), (S-P-E-EP-S), (S-P-E-EB-S), (S-B-P-EP-S), (S-B-P-EB-S), (S-B-P-EP-S), (S-P-EB-EB-S), (S-P-EP-EP-S), (S-P-EB-EP-S), (S-P-EP-EB-S), (S-P-EP-P-EP-S), (S-P-EB-P-EB-S), (S-P-EP-P-EB-S), (S-B-EB-P-EB-S), (S-B-EP-P-EP-S), (S-P-EB-B-EP-S), (S-P-EP-B-EB-S), (S-E-EP-P-S), (S-E-EB-P-S), (S-EP-EP-S), (S-E-P-EB-S), (S-E-EP-P-EP-S), (S-E-EB-P-EB-S), (S-E-EP-P-EB-S), (S-E-EP-E-EP-S), (S-B-EP-B-EP-B-S), (S-P-EP-P-EP-P-S), (S-E-EB-E-EB-E-S), (S-P-EP-P-EP-P-S), (S-E-EP), (S-E-EP-E)$_n$, (S-B-EP)$_n$, (S-E-EB-S)$_n$, (S-EB-EP-)$_n$, (S-E-EP-EB)$_n$, (S-B-EB)$_n$, (S-E-EB-E)$_n$, (S-B-EP-E)$_n$, (S-B-EB-E)$_n$, (S-B-EP-B)$_n$, (S-B-EB-B)$_n$, (S-E-E-EP)$_n$, (S-E-E-EB)$_n$, (S-B-E-EP)$_n$, (S-B-E-EB)$_n$, (S-B-B-EP)$_n$, (S-B-B-EB)$_n$, (S-E-B-EB)$_n$, (S-E-B-EP)$_n$, (S-EB-EB)$_n$, (S-EP-EP)$_n$, (S-E-EB-EB)$_n$, (S-E-EP-EP)$_n$, (S-E-EB-EP)$_n$, (S-B-EB-EB)$_n$, (S-B-EP-EP)$_n$, (S-B-EB-EP)$_n$, (S-B-EP-EB)$_n$, (S-E-EP-E-EP)$_n$, (S-E-EB-E-EB)$_n$, (S-E-EP-E-EB)$_n$, (S-B-EP-B-EP)$_n$, (S-B-EB-B-EB)$_n$, (S-B-EB-B-EP)$_n$, (S-B-EB-E-EB)$_n$, (S-B-EP-E-EP)$_n$, (S-E-EB-B-EP)$_n$(S-E-EP-B-EB)$_n$, (S-P-EB)$_n$, (S-P-EP)$_n$, (S-P-EP-P)$_n$, (S-P-EB-P)$_n$, (S-B-EP-P)$_n$, (S-B-EB-P)$_n$, (S-P-E-EP)$_n$, (S-P-E-EB)$_n$, (S-B-P-EP)$_n$, (S-B-P-EB)$_n$, (S-P-B-EB)$_n$, (S-P-B-EP)$_n$, (S-P-EB-EB)$_n$, (S-P-EP-EP)$_n$, (S-P-EB-EP)$_n$, (S-P-EP-EB)$_n$, (S-P-EP-P-EP)$_n$, (S-P-EB-P-EB)$_n$, (S-P-EP-P-EB)$_n$, (S-B-EB-P-EB)$_n$, (S-B-EP-P-EP)$_n$, (S-P-EB-B-EP)$_n$, (S-P-EP-B-EB)$_n$, (S-E,EP-P)$_n$, (S-E-EB-P)$_n$, (S-E-P-EP)$_n$, (S-E-P-EB)$_n$, (S-E-EP-P-EP)$_n$, (S-E-EB-P-EB)$_n$, (S-E-EP-P-EB)$_n$, (S-E-EP-E-EP)$_n$, (S-B-EP-B)$_n$, (S-P-EP-P-EP-P)$_n$, (S-E-EB-E-EB-E)$_n$, and (S-P-EP-P-EP-P)$_n$, multiblock copolymers, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I. The tensile strength is found to decrease with increase orientation, and the optimum tensile strength found for gel samples with the least amount of stress or orientation imparted during cool from the molten state to room temperature. cl EXAMPLE IV Example II is repeated using plasticizers L-14, L-50, L-100, H-15, H-25, H-35, H-50, H-100, H-300, L-14E, H-300E, Actipol E6, E16, E23, Kraton L-1203, EKP-206, EKP-207, HPVM-2203, Amoco C-60, Piccolyte S10, Duroprime (55, 70, 90, 200, 350, 400), Tufflo (6006, 6016, 6016M, 6026, 6036, 6056, 6206,) Bayol, Bernol, American, Blandol, Drakeol, Ervol, Gloria, and Kaydol, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I.

EXAMPLE V

Example III is repeated using plasticizers L-14, L-50, L-100, H-15, H-25, H-35, H-50, H-100, H-300, L-14E, H-300E, Actipol E6, E16, E23, Kraton L-1203, EKP-206, EKP-207, HPVM-2203, Amoco C-60, Piccolyte S10, Duroprime (55, 70, 90, 200, 350, 400), Tufflo (6006, 6016, 6016M, 6026, 6036, 6056, 6206,) Bayol, Bernol, American, Blandol, Drakeol, Ervol, Gloria, and Kaydol, the bulk gel rigidities are found to be within the range of 2 gram to 1,800 gram Bloom and the tear resistance of the multiblock copolymers at corresponding rigidities are found to be substantially higher than the tear resistance of the triblock copolymer gels of EXAMPLE I.

EXAMPLE VI

A gel composition of 100 parts of Kuraray's S-E-EP-S 4055 copolymer and 400 parts by weight of Duroprime 200 white oil was made following Example I and extruded and drawn (from a 7.15 mm diameter orifice) into a strand of uniform diameter onto a take-up roll of continuous lengths. The strand diameter was varied by increasing and decreasing the speed of the take-up roll. The continuous strand of varying diameter gel strand was cut to suitable lengths for use and testing as dental floss. Additional gel was also casted in varying thickness and tested. The results of samples tested are shown in Table 3, #4–7; Table 4, #12–15 and 20, Table 5 #22, 23, 27–29; Table 6 #36–32; Table 7, #40–43, #76 and 77. Sample Nos. 76 and 77 were tested together. Sample 77 exhibited higher tensile strength after 27.75% of plasticizing oil was extracted (with 2.89 parts by weight of oil remaining), its rigidity remained substantially unchanged.

EXAMPLE VII

A gel composition of 100 parts of Kraton G1651 and 400 parts by weight of Duroprime 200 white oil was made following Example I and extruded and drawn (from a 7.15 mm diameter orifice) into a strand of uniform diameter onto a take-up roll of continuous lengths The strand diameter was varied by increasing and decreasing the speed of the take-up roll. The continuous strand of varying diameter gel strand was cut to suitable lengths for use and testing as dental floss. Additional gel was also casted in varying thickness and tested. The results of samples tested are shown in Table 3B, #8–11; Table 4, #16–19 and 21; Table 5, #2426; Table 6, #33–35; and Table 7, #3639.

EXAMPLE VIII

Example II was repeated melt blending under inert gas 100 parts by weight of Kuraray (S-E-EP-S) 4077 multiblock copolymer and 400 parts by weight of Duroprime 70 white oil. A first part of the molten gel was allowed to cool to room temperature, the remainder gel was heated under inert gas for an additional three hours at 300–325° F. and a second part of the gel was extruded (from a 7.15 mm diameter orifice) into cold running water, and the third and final remaining gel was allowed to cool to room temperature. The bulk gel rigidities of the first, second and third parts were found to be within the range of 2 to 1,800 gram Bloom. The second and third final parts of the gel appeared to be altered and different from the first gel part. The first part exhibited rapid return when extended, but the second and third final parts exhibited delay elastomeric recovery when released after extension and deformation. All of the samples exhibited 100% recovery after repeated extensions and deformations.

TABLE 3A

Flossing Cycles to Break

| Sample No. | Floss Type | cross-section size (mm$^2$) | $^2$Floss amalgam molars to break | $^3$Floss fronts to break |
|---|---|---|---|---|
| 1 | $^4$Unwaxed spongy nylon | 0.30 | 18 | 200+ |
| 2 | $^5$Regular waxed nylon | 0.11 | 11 | 200+ |
| 3 | $^6$Extra fine unwaxed nylon | 0.06 | 6 | 200+ |

TABLE 3B

Flossing Cycles to Break

| Sample No. | Floss Type | $^1$Relaxed/extended dia. (mm) | $^2$Floss amalgam molars to break | $^3$Floss fronts to break |
|---|---|---|---|---|
| 4 | $^7$Gel | 2.42/0.16 | 37 | 76 |
| 5 | $^7$Gel | 2.63/0.17 | 29 | 83 |
| 6 | $^7$Gel | 2.75/0.17 | 36 | 183 |
| 7 | $^7$Gel | 2.83/0.20 | 20 | 74 |
| 8 | $^8$Gel | 3.22/0.22 | 8 | 30 |
| 9 | $^8$Gel | 2.48/0.31 | 4 | 20 |
| 10 | $^8$Gel | 3.16/0.33 | 6 | 44 |
| 11 | $^8$Gel | 2.86/0.24 | 5 | 29 |

$^1$floss dimension relaxed state and when extended during flossing cycles. $^2$Test conditions: number of flossing cycles (before breaking) between amalgam alloy metal (fully contacting) lower, left first and second human back molars. $^3$Test conditions: number of flossing cycles (before breaking) between upper human front teeth. $^4$Oral-B Ultra Floss™, interlocking network of spongy nylon floss. $^5$Johnson & Johnson regular waxed nylon floss. $^6$Johnson & Johnson extra fine unwaxed nylon floss. $^7$Gel made from 100 parts by weight of S-E-EP-S 4055 multiblock copolymer having a Brookfield viscosity of 90 as measured for a 5wt % solution in toluene at 30° C. and 400 parts by weight of Duroprime 200 plasticizing oil. $^8$Gel made from 100 parts by weight of SEBS Kraton G1651 copolymer having a Brookfield viscosity of 40 as measured for a 5wt % solution in toluene at 30° C. $^{2,3}$Any selected test methods may be utilized in testing the floss performance of the gels. For example, a set of simulated upper front teeth fully contacting under a uniform spring load of two pounds may be used in place of human teeth. Such simulated testing conditions may be more severe than conditions 2 and less severe than conditions 3 above.

TABLE 4

Tensile Strength of Gel Strands

| Sample No. | Number of Strands | Radius (mm) | Area (cm$^2$) | Failure (Kg) | Tensile (Kg/cm$^2$) |
|---|---|---|---|---|---|
| 12 | 3 | 1.325 | 0.165 | 9.00 | 54.54 |
| 13 | 4 | 1.250 | 0.196 | 9.50 | 48.39 |
| 14 | 4 | 1.421 | 0.253 | 9.50 | 37.44 |
| 15 | 5 | 1.359 | 0.290 | 12.5 | 43.08 |
| 16 | 2 | 2.14 | 0.287 | 14.0 | 48.78 |
| 17 | 2 | 1.55 | 0.151 | 11.5 | 75.95 |
| 18 | 2 | 1.17 | 0.086 | 8.50 | 98.84 |
| 19 | 2 | 1.322 | 0.109 | 9.0 | 81.96 |
| 20 | 6 | 1.375 | 0.356 | 14 | 39.32 |
| 21 | 2 | 1.445 | 0.131 | 10 | 76.33 |
| 76 | 1 | 1.22 | 0.0467 | 2.00 | 42.82 |
| 77† | 1 | 1.38 | 0.0598 | 4.00 | 66.88 |

†Plasticizing oil extracted

TABLE 5

Tensile Strength of Bulk Gels Samples

| Sample No. | Cross-section (cm$^2$) | Failure (Kg) | Tensile (Kg/cm2) |
|---|---|---|---|
| 22 | 1.96 | 24.0 | 12.24 |
| 23 | 1.56 | 25.0 | 16.02 |
| 24 | 0.58 | 15.0 | 25.83 |
| 25 | 0.602 | 16.0 | 26.54 |
| 26 | 1.163 | 24.0 | 20.64 |
| 27 | 0.913 | 21.0 | 23.00 |
| 28 | 0.595 | 18.5 | 36.56 |
| 29 | 0.702 | 19.0 | 27.06 |

TABLE 6

180° U Bend Tear Propagation of Bulk Gels Samples

| Sample No. | Tear width (cm) | Failure (Kg) | Tear Force (Kg/cm) |
|---|---|---|---|
| 30 | 1.31 | 2.75 | 2.09 |
| 31 | 1.28 | 3.0 | 2.30 |
| 32 | 1.14 | 2.75 | 2.56 |
| 33 | 1.53 | 2.75 | 1.79 |
| 34 | 1.27 | 2.25 | 1.76 |
| 35 | 1.26 | 2.25 | 1.77 |

TABLE 7

Notched Gel Strand Tension Tear Propgation

| Sample No. | Strand Dia. (mm) | Failure (Kg) | Tear Force (Kg/cm) |
|---|---|---|---|
| 36 | 2.86 | 0.75 | 2.62 |
| 37 | 2.49 | 0.75 | 3.01 |
| 38 | 3.09 | 0.60 | 1.94 |
| 39 | 2.62 | 0.70 | 2.67 |
| 40 | 2.54 | 0.60 | 2.36 |
| 41 | 1.94 | 1.10 | 5.67 |
| 42 | 1.58 | 0.75 | 4.74 |
| 43 | 2.34 | 1.2 | 5.12 |

The tensile strengths of gels made from higher viscosity copolymers are lower than the tensile strengths of gels made from lower solution viscosity copolymers. This was later found to be due to orientation effects and not considered significant.

The tear resistance of gels made from higher viscosity copolymers are higher than the tear resistance of gels made from lower solution viscosity copolymers.

Gel strands made from higher viscosity copolymers perform better than gel strands made of lower viscosity copolymers when used in flossing amalgam molars and more than three times better when used in flossing front teeth.

As compared to spongy nylon, regular waxed nylon, and extra fine unwaxed nylon when flossing amalgam molars, the performance of gels are on the average substantially better.

Examples below illustrate other modes of practice contemplated.

EXAMPLE IX

At least 120 pcs of the gel strands of EXAMPLE II containing 600 parts oil is individually weighted and placed in a heated vacuum oven, a partial vacuum is applied and the temperature is regulated between about 80° F. to about 150° F. to extract plasticizer from the gel strands. At various oven and vacuum times, three gel strands are removed from the vacuum oven, allowed to cool to room temperature, weighted to determine the amount of weight loss and tested for tensile and tear strength As the amount of oil contained in the original gel is reduced from 600 parts by weight to less than 200 parts by weight, the "reduced plasticizer volume" gels are weighted and tested. The tear and tensile strengths of the reduced plasticizer volume gels are found to be improved over the properties of the original 600 parts by weight referenced gel strands.

The gels are especially advantageously useful when subjected to conditions of stretching, shearing, and tearing during flossing. The gels useful for flossing are characterized by low rigidities and high solution viscosity of the gels made from multiblock copolymers having two or more midblock polymer chains.

Tables 8–11 are illustrative in meeting one or more of the criteria detailed above.

8. Illustrative Modes of Practice Contemplated for multiblock copolymer Gels

| 100 Parts by wt | 5 Wt % Copolymer Viscosity (cps) | Styrene % | Parts by Wt of Oil | Number of floss cycles to break | Sample No. |
|---|---|---|---|---|---|
| S-E-EP-S | 90 | 30 | 300 | 30+ | 44 |
| S-E-EP-E-S | 60 | 30 | 300 | 30+ | 45 |
| (S-E-EP)n | 240 | 35 | 300 | 30+ | 46 |
| (S-E-EP-E)n | 240 | 35 | 300 | 30+ | 47 |
| S-B-EP-S | 90 | 30 | 300 | 30+ | 48 |
| S-E-EB-S | 90 | 35 | 300 | 30+ | 49 |
| S-EB-EP-S | 90 | 30 | 300 | 30+ | 50 |
| S-E-EP-EP-S | 90 | 30 | 300 | 30+ | 51 |

TABLE 9

Illustrative Modes of Practice Contemplated for multiblock copolymer Gels

| 100 Parts by wt | 5 Wt % Copolymer Viscosity (cps) | Styrene % | Parts by Wt of Oil | Number of Floss cycles to Break | Sample No. |
|---|---|---|---|---|---|
| S-E-EP-EB-S | 120 | 33 | 250 | 30+ | 52 |
| S-E-EP-EP-S | 120 | 33 | 250 | 30+ | 53 |
| (S-B-EP)n | 380 | 35 | 250 | 30+ | 54 |
| (S-E-EB)n | 380 | 35 | 250 | 30+ | 55 |
| S-E-EP-E-EP-S | 120 | 30 | 250 | 30+ | 56 |
| S-E-EP-P-S | 120 | 35 | 250 | 30+ | 57 |
| S-E-B-EP-S | 120 | 30 | 250 | 30+ | 58 |
| S-E-EP-EP-E-S | 120 | 30 | 250 | 30+ | 59 |

TABLE 10

Illustrative Modes of Practice Contemplated for multiblock copolymer (0.5–2.0 cm diameters) Gel Strands

| 100 Parts by wt | 5 Wt % Copolymer Viscosity (cps) | Styrene % | Parts by Wt of Oil | # of Floss cycles to Break | Sample No. |
|---|---|---|---|---|---|
| S-E-EP-S | 40 | 30 | 350 | 30+ | 60 |
| S-E-EP-S | 60 | 30 | 350 | 30+ | 61 |
| (S-E-EP-EB)n | 340 | 30 | 350 | 30+ | 62 |
| (S-E-EP-EP-E)n | 340 | 30 | 350 | 30+ | 63 |
| S-E-EP-E-EP-E-S | 90 | 30 | 350 | 30+ | 64 |
| S-EB-EP-EP-S | 90 | 35 | 350 | 30+ | 65 |
| S-B-EB-B-S | 90 | 30 | 350 | 30+ | 66 |
| S-E-EP-EP-E-S | 90 | 30 | 350 | 30+ | 67 |

TABLE 11

Illustrative Modes of Practice Contemplated for multiblock copolymer (0.5–2.0 cm diameters) Gel Strands

| 100 Parts by wt | 5 Wt % Copolymer Viscosity (cps) | Styrene % | Parts by Wt of Oil | # of Floss cycles to Break | Sample No. |
|---|---|---|---|---|---|
| S-E-EB-S | 120 | 30 | 250 | 40+ | 68 |
| S-E-EP-S | 120 | 30 | 250 | 40+ | 69 |
| (S-E-EB)n | 280 | 35 | 250 | 40+ | 70 |
| (S-E-EP)n | 280 | 35 | 250 | 40+ | 71 |
| S-E-EP-E-S | 120 | 30 | 250 | 40+ | 72 |
| S-EP-E-EP-S | 120 | 30 | 250 | 40+ | 73 |
| S-EB-E-EB-S | 120 | 30 | 250 | 40+ | 74 |
| S-EB-EB-S | 120 | 30 | 250 | 40+ | 75 |

EXAMPLE X

Gels of 100 parts of Kraton G1651, Kraton RP-6917 (amorphous S-EB-S), Septon 8006 (amorphous S-EB-S), Kraton RP-6919, Septon S2006 (amorphous S-EP-S) and a high viscosity radial amorphous midblock segment (SEB)n triblock copolymers and 1,600, 1,200, 1,000, 800, 600, 500, 450, 300, 250 parts by weight of Duroprime 200 white oil (plasticizer having Vis. cSt @ 40° C. of 39.0) are melt blended, test, and tack probe samples molded, the bulk gel rigidities are found to be within the range of 2 to 1,800 gram Bloom and the tensile strength, notched tear strength, and resistance to fatigue are found to decrease with increase amounts of plasticizers, while tackiness of the gels is found to be greater than 7.6 gram Tack

EXAMPLE XI

Gels of 100 parts of Septon crystalline (SEEPS) copolymers 4033, 4055, and 4077 and 1,600, 1,200, 1,000, 800, 600, 500, 450, 300, 250 parts by weight of Duroprime 200 white oil (plasticizer having Vis. cSt @ 40° C. of 39.0) are melt blended, test and tack probe samples molded, the bulk gel rigidities are found to be within the range of 2 to 1,800 gram Bloom and the gel tackiness are found to increase with increase amounts of plasticizers and the tack greater than 7.6 gram Tack.

EXAMPLE XII

Gels of 100 parts of Septon crystalline (SEEPS) copolymers 4033, 4055, and 4077 in combination with sufficient amounts of a Dow S series poly(ethylene/styrene) random copolymer (250,000 Mw) having a high styrene content sufficient to form gel blends with total styrene content of 37 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XII

Gels of 100 parts of Septon 4045 (crystalline S-E/EP-S having a styrene content of 37.6) and 1,600, 1,200, 1,000, 800, 600, 500, 450, 300, 250 parts by weight of Duroprime Klearol white oil (plasticizer having Vis. CSt @ 40° C. of 7–10) are melt blended, test and probe samples molded, the bulk gel rigidities are found to be within the range of 2 to 2,000 gram Bloom and the tackiness is found to be less than about 1 gram Tack.

EXAMPLE XIV

Gels of 100 parts of Septon crystalline (SEEPS) copolymers 4033, 4055, and 4077 in combination with sufficient amounts of Septon 2104 (Amorphous SEPS having a high styrene content of 65) and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and tack is found to decrease with decreasing plasticizer content and in all instances substantially lower than the gels of Example X and XI.

EXAMPLE XV

Gels of 100 parts of Septon crystalline (SEEPS) copolymers 4033, 4055, and 4077 in combination.with sufficient amounts of a Dow M series poly(ethylene/styrene) random copolymer (350,000 Mw) having a high styrene content sufficient to form gel blends with total styrene content of 37 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XVI

Gels of 100 parts of Septon crystalline (SEEPS) copolymers 4033, 4055, and 4077 in combination with sufficient amounts of a Dow E series poly(ethylene'styrene) random copolymer (240,000 Mw) having a high styrene content sufficient to form gel blends with total styrene content of 37 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XVII

Gels of 100 parts of Septon crystalline (SEEPS) copolymers 4033, 4055, and 4077 in combination with polystyrene homopolymers (having Mw of 3,000; 4,000; 5,000; 6,000; 7,000; 8,000; 9,000; 10,000; 11,000; 12,000, 13,000; 14,000; 15,000; 16,000; 17,000; 18,000, 19,000; 20,000; 30,000; 40,000; 50,000; 60,000; 70,000; 80,000; 90,000) in sufficient amounts to form gel blends with total styrene content of 37, 45, 48, 50, and 55 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 2,000 gram Bloom and tack is found to decrease with decreasing plasticizer content and in all instances substantially lower than die gels of Example I and II.

EXAMPLE XVIII

Gels of 100 parts of Septon crystalline (SEEPS) copolymers 4033, 4055, and 4077 in combination with sufficient amounts of a Dow M series poly(ethylene/styrene) random copolymer (350,000 Mw) having a high styrene content sufficient to form gel blends with total styrene contents of 40, 45, 48, 50, and 55 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XIX

Gels of 100 parts of Septon crystalline (SEEPS) copolymers 4033, 4055, and 4077 in combination with sufficient amounts of a Dow S series poly(ethylene/styrene) random copolymers (with Mw of 140,000; 250,000 and 340,000) having a high styrene content sufficient to form gel blends with total styrene content of 40, 45, 48, 50, and 55 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XX

Gels of 100 parts of Septon crystalline (SEEPS) copolymers 4033, 4055, and 4077 in combination with sufficient amounts of a Dow E series poly(ethylene/styrene) random copolymers (with Mw of 250,000; 340,000 and 400,000) having a high styrene content sufficient to form gel blends with total styrene content of 40, 45, 48, 50, and 55 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XXI

Gels of 100 parts of Septon crystalline (SEEPS) copolymers 4033, 4055, and 4077 in combination with sufficient amounts of a Dow M series poly(ethylene/styrene) random copolymer (with Mw of 250,000; 340,000 and 400,000) having a high styrene content sufficient to form gel blends with total styrene content of 40, 45, 48, 50, and 55 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XXII

Gels of 100 parts of Septon crystalline (SEEPS) copolymers 4033, 4045, 4055, and 4077 in combination with sufficient amounts of a Dow E series crystalline poly (ethylene/styrene) random copolymer (with Mw of 250,000; 340,000 and 400,000) having a high styrene content sufficient to form gel blends with total styrene content of 37, 40, 45, 48, 50, 55, and 60 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XXIII

Gels of 100 parts of Septon crystalline (SEEPS) copolymers 4033, 4055, and 4077 in combination with polystyrene (of 2,500 Mw, 4,000 Mw, 13,000 Mw, 20,000 Mw, 35,000 Mw, 50,000 Mw, and 90,000 Mw; poly(alphamethylstyrene) (of 1,300 Mw, 4,000 Mw; poly(4-methylstyrene)(of 72,000 Mw), Endex 155, 160, Kristalex 120, and 140 ) in sufficient amounts to form gel blends with total styrene content of 37, 45, 48, 50, and 55 by weight of copolymers and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 2,000 gram Bloom and tack is found to decrease with decreasing plasticizer content and in all instances substantially lower than the gels of Example I and II.

EXAMPLE XXIV

Examples XIV is repeated and gels of 100 parts of (S-EB$_{45}$-EP-S), (S-E-EB$_{25}$-S), (S-EP-E-EP-S), (S-E-EB-S), (S-E-EP-S), (S-E-EP-E-S), (S-E-EP-EB-S), (S-E-EP-E-EP-S), (S-E-EP-E-EB-S), (S-E-EP-E-EP-E-S), (S-E-EP-E-EB-S), (S-E-EP-E-EP-EB-S), and (S-E-EP-E-EP-E-S) block copolymers are each melt blended, tests and probe samples molded, the bulk gel rigidities are found to be within the range of 2 to 1,800 gram Bloom and tack is found to decrease with decreasing plasticizer content and in all instances substantially lower than the gels of Example I and II.

EXAMPLE XXV

Example XIV is repeated and minor amounts of 2, 5, 10 and 15 parts of the following polymers are formulated with each of the triblock copolymers: styrene-butadiene-styrene block copolymers, styrene-isoprene-styrene block copolymers, low viscosity styrene-ethylene-butylene-styrene block copolymers, styrene-ethylene-propylene block copolymers, styrene-ethylene-propylene-styrene block copolymers, styrene-butadiene, styrene-isoprene, polyethyleneoxide, poly(dimethylphenylene oxide), polystyrene, polybutylene, polyethylene, polypropylene, high ethylene content EPDM, amorphous copolymers based on 2,2-bistrifluoromethyl-4,5-difuoro-1,3-dioxole/ tetrafluoroethylene. The bulk gel rigidities of each of the formulations are found to be within the range of 2 gram to 2,000 gram Bloom and tack is found to decrease with decreasing plasticizer content and in all instances substantially lower than the gels of Example I and II.

EXAMPLE XXVI

Molten gels of Examples III–XVI are formed into composites with paper, foam, plastic, elastomers, fabric, metal, concrete, wood, glass, ceramics, synthetic resin, synthetic fibers, and refractory materials and the resistance to fatigue of the composite-crystal gels at corresponding rigidities are found to be greater than that of the composite-amorphous gels of Example X.

EXAMPLE XXVII

Three cm thick sheets of each of the crystal gels of Example XIV and the amorphous gels of Example I are tested by repeatedly displacing the sheets to a depth of 1 cm using a 10 cm diameter smooth (water soaked) wood plunger for 1,000, 5,000, 10,000, 25,000, 50,000, and 100,000 cycles. The sheets of crystal gels are found capable of exhibiting greater fatigue resistance than the sheets of amorphous gels at corresponding rigidities.

EXAMPLE XXVIII

Gels of 100 parts of Septon crystalline (SEEPS) copolymers 4033, 4055, and 4077 in combination with sufficient amounts of a Dow poly(ethylene/styrene) random copolymers ES16 having 37.5% crystallinity and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXIX

Gels of 100 parts of Septon crystalline (SEEPS) copolymers 4033, 4055, and 4077 in combination with sufficient amounts of a Dow poly(ethylene/styrene) random copolymer, ES24 having 26.6% crystallinity and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXX

Gels of 100 parts of Septon crystalline (SEEPS) copolymers 4033, 4055, and 4077 in combination with sufficient amounts of a Dow poly(ethylene/styrene) random copolymers ES27 having 17.4% crystallinity and 800, 600, 500, 450, 300, 250 parts by weight of Duroprime 55, 70, Klearol, Carnation, Blandol, Benol, Semtol 85, 70, and 40 (plasticizers having Vis CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXXI

Gels of 100 parts of Septon crystalline (SEEPS) copolymers 4033, 4055, and 4077 in combination with sufficient amounts of a Dow poly(ethylene/styrene) random copolymers ES28 having 22.9% crystallinity and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXII

Gels of 100 parts of Septon crystalline (SEEPS) copolymers 4033, 4055, and 4077 in combination with sufficient amounts of a Dow poly(ethylene'styrene) random copolymers ES30 having 9.6% crystallinity and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXXIII

Gels of 100 parts of Septon crystalline (SEEPS) copolymers 4033, 4055, and 4077 in combination with sufficient amounts of a Dow poly(ethylene/styrene) random copolymers ES44 having 5.0% crystallinity and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXXIV

Gels of 10 parts of Septon crystalline (SEEPS) copolymers 4033, 4055, and 4077 in combination with sufficient amounts of a Dow poly(ethylene'styrene) random copolymers ES72 and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXXV

Gels of 100 parts of Septon crystalline (SEEPS) copolymers 4033, 4055, and 4077 in combination with sufficient amounts of a Dow poly(ethylene/styrene) random copolymers ES73 and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the

EXAMPLE XXXVI

Gels of 100 parts of Septon crystalline (SEEPS) copolymers 4033, 4055, and 4077 in combination with sufficient amounts of a Dow poly(ethylene/styrene) random copolymers ES74 and 800, 600, 500, 450, 300, 250 parts by weight of Duroprime 55, 70, Klearol, Carnation, Blandol, Benol, Semtol 85, 70, and 40 (plasticizers having Vis. CSt i) 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXXVII

Gels of 100 puts of Septon crystalline (SEEPS) copolymers 4033, 4055, and 4077 in combination with sufficient amounts of a Dow poly(ethylene/styrene) random copolymers ES69 and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXXVIII

Gels of 100 parts of Septon crystalline (SEEPS) copolymers 4033, 4055, and 4077 in combination with sufficient amounts of a Dow poly(ethylene/styrene) random copolymers ES62 and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XXXIX

Gels of 100 parts of Septon (SEPS) copolymers Kraton GRP6918 in combination with each of a Dow poly(ethylene/styrene) random copolymers ES16, ES24, ES27, ES28, ES30, and ES44 and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XL

Gels of 100 pats of Septon (SEBS) copolymers S8006 and Kraton G1651, G1654 in combination with sufficient amounts of a Dow poly(ethylene/styrene) random copolymers ES16, ES24, ES27, ES28, ES30, and ES44 and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XLI

Gels of 100 parts of Septon (SEEPS) copolymers 4033, 4045, 4055, 4077 in combination each with 25 parts by weight of Super Sta-tac, Betaprene Nevtac, Escorez, Hercotac, Wingtack, Piccotac, polyterpene, Zonarez, Nirez, Piccolyte, Sylvatac, glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene vinyl toluene copolymer (Piccotex), polystyrene (Kristalex, Piccolastic), special resin (LX-1035) and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

EXAMPLE XLII

Gels of 200 parts of Septon (SEEPS) copolymers 4033, 4045, 4055, 4077 in combination each with 25 parts by weight of Super Sta-tac, Betaprene Nevtac, Escorez, Hercotac, Wingtack, Piccotac, polyterpene, Zonarez, Nirez, Piccolyte, Sylvatac, glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035) and 800, 600, 500, 450, 300, 250 parts by weight of Duroprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example X.

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

What is claimed is:

1. A composite comprising: a gel denoted by G, being in adherent contact, adhesive contact, clinging contact, fastening contact, sticking contact, or physical contact with a selected material M forming the combination $G_nM_n$, $G_nM_nG_n$, $M_nG_nM_n$, $M_nG_nG_nM_n$, $G_nM_nM_nG_n$, $G_nM_nG_nM_nG_n$, $M_nM_nM_nG_n$, $M_nM_nM_nG_nM_nM_nM_n$ or a permutation of one or more of said $G_n$ with $M_n$; wherein when n is a subscript of M, n is the same or different selected from the group consisting of paper, foam, plastic, fabric, metal, metal foil, metalic flakes, concrete, wood, glass, glass fibers, ceramics, synthetic resin, synthetic fibers or refractory materials; and wherein when n is a subscript of G, n denotes the same or a different gel rigidity; said gel comprising: (i) 100 parts by weight of one or more block copolymers selected from poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-propylene-ethylene-styrene), poly(styrene-ethylene-ethylene-butylene)$_n$, poly(styrene-ethylene-ethylene-propylene)$_n$, poly(styrene-ethylene-ethylene-butylene$_{25}$)$_n$, poly(styrene-ethylene-propylene-ethylene)$_n$, or mixtures thereof, wherein subscript n is two or more; (ii) about 300 to about 1,600 parts by weight of one or more plasticizing oils with a selected amount of at least one said plasticizing oil(s) having a viscosity of about 4 cSt at 40° C. and greater; said gel characterized by a gel gram Bloom of about 2 gram to about 1,800 gram Bloom; and in combination with or without (iii) a selected amount of one or more polymers or copolymers comprising poly(styrene-butadiene-styrene), poly(styrene-butadiene)$_n$, poly(styrene-isoprene)$_n$, poly(ethylene-styrene), poly(styrene-ethylene-propylene), poly(styrene-ethylene-butylene), poly(styrene-ethylene-propylene)$_n$, poly(styrene-ethylene-butylene )$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; said gel having greater tear resistance than gels having corresponding rigidity made from a poly(styrene-ethylene-butylene-styrene) or poly(styrene-ethylene-propylene-styrene) block copolymers.

2. A composite comprising: a gel denoted by G, being in adherent contact, adhesive contact, clinging contact, fastening contact, sticking contact, or physical contact with a selected material M or in combination with one or more of the same gel or a different gel forming a composite of the combination $G_nG_n$, $G_nG_nG_n$, $G_nM_n$, $G_nM_nG_n$, $M_nG_nM_n$, $M_nG_nG_n$, $M_nM_nM_nG_nM_n$, $M_nG_nG_nM_n$, $G_nM_nG_nG_n$, $G_nG_nM_nM_n$, $G_nM_nM_nG_n$, $G_nG_nM_nG_nM_nG_nG_n$, $G_nM_nG_nM_nM_n$, $M_nG_nM_nG_nM_nG_n$, $G_nG_nM_nM_nM_n$, $G_nG_nM_nG_nM_n$, $G_nG_nM_nG_nM_nG_n$, $G_nM_nG_nM_nG_n$, $M_nM_nM_nG_n$, $M_nM_nM_nG_nM_nM_nM_n$ or a permutation of one or more of said $G_n$ with $M_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity; said gel comprising: (i) 100 parts by weight of one or more block copolymers selected from poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-propylene-ethylene-styrene), poly(styrene-ethylene-ethylene-butylene)$_n$, poly(styrene-ethylene-ethylene-propylene)$_n$, poly(styrene-ethylene-ethylene-butylene$_{25}$)$_n$, poly(styrene-ethylene-propylene-ethylene)$_n$, or mixtures thereof, wherein subscript n is two or more; (ii) about 300 to about 1,600 parts by weight of one or more plasticizing oils with a selected amount of at least one said plasticizing oil(s) having an average molecular weight of about 200 and greater; said gel characterized by a gel gram Bloom of about 2 gram to about 1,800 gram Bloom; and in combination with or without (iii) a selected amount of one or more polymers or copolymers comprising poly(styrene-butadiene-styrene), poly(styrene-butadiene)$_n$, poly(styrene-isoprene)$_n$, poly(styrene-ethylene-propylene), poly(ethylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; said gel having greater fatigue resistance than gels having corresponding rigidity made from a poly(styrene-ethylene-butylene-styrene) or poly(styrene-ethylene-propylene-styrene) block copolymers.

3. A composite according to claim 1, wherein. said composite being formed into a gel hand exercising grip, a gel shape floss suitable for use as a dental floss, a gel crutch cushion, a gel cervical pillow, a gel bed wedge pillow, a gel leg rest, a gel neck cushion, a gel mattress, a gel bed pad, a gel elbow pad, a gel dermal pad, a gel wheelchair cushion, a gel helmet liner, a gel cold and hot pack, a gel exercise weight belt, a gel traction pad or belt, a gel cushion for splints, a gel sling, a gel brace for the hand, wrist, finger, forearm, knee, leg, clavicle, shoulder, foot, ankle, neck, back, rib, a gel sole for orthopedic shoe, a gel shaped toy article, a gel optical cladding for cushioning optical fibers from bending stresses, a gel swab tip, a gel fishing bait, a gel seal against pressure, a gel thread, a gel strip, a gel yarn, a gel tape, a weaved gel cloth, a gel fabrics, a gel balloon for valvuloplasty of the mitral valve, a gel trointestinal balloon dilator, a gel esophageal balloon dilator, a gel dilating balloon catheter use in coronary angiogram, a gel condom, a gel toy balloon, a gel surgical and examination glove, a self sealing enclosures for splicing electrical and telephone cables and wires, a gel film, or a gel liner.

4. A composite of claim 2 shaped in the form of a gel liner for lower limb or above the knee amputee prosthesis formed by injection molding, extruding, spinning, casting, or dipping of said gel.

5. A composite of claim 1 shaped in the form of a gel liner for lower limb or above the knee amputee prosthesis formed by injection molding, extruding, spinning, casting, or dipping of said gel.

6. A composite comprising a gel $G_n$ with a selected material $M_n$; said gel formed from (I) 100 parts by weight of one or more linear, branched, star-shaped (radial), or multiarm block copolymers or mixtures of two or more such block copolymers, said block copolymers having one or more midblock segments, said midblock segments comprising one or more polyethylene segments and with (i) one or more amorphous midblocks or (ii) without amorphous midblocks, and in combination with or without a selected amount of one or more (II) polymers or copolymers, and selected amounts of (III) one or more plasticizing oils with a selected amount of at least one said plasticizing oil(s) having an average molecular weight of about 200 and greater; said plasticizing oil(s) being of sufficient amount to achieve gel rigidities of from less than about 2 gram Bloom to about 1,800 gram Bloom, with the proviso when said (I) block copolymers without any amorphous midblock segments are combined with at least one block copolymer having at least one amorphous midblock segments, that said midblock segment(s) of said (I) block copolymers forming said gel comprises a polyethylene midblock segment; said (II) polymer or compolymer selected from poly(styrene-butadiene-styrene), poly(styrene-butadiene)$_n$, poly(styrene-isoprene)$_n$, poly(styrene-ethylene-propylene), poly(ethylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and wherein said composite formed from the combination $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with a material $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity; said $G_n$ and $M_n$ combination(s) being in one or more the same or different selected adherent contact, adhesive contact, clinging contact, fastening contact, sticking contact, or physical contact.

7. A composite comprising a gel $G_n$ with a selected material $M_n$, said gel formed from
(i) 100 parts by weight of one or more block copolymers of the formula poly(styrene-ethylene-ethylene-propylene-styrene), having greater tear resistance than a gel of corresponding rigidity made from a poly(styrene-ethylene-propylene-styrene) block copolymer, wherein said (i) block copolymer is a high viscosity copolymer having a viscosity value at 5 weight percent solution in toluene at 30° C. of about 90 mPa.S and higher which corresponds to a viscosity at 10 weight percent of about 5800 mPa.S and higher which corresponds to a viscosity at 20 weight percent solids solution in toluene at 25° C. of at about 80,000 mPa.S and higher, and from
(ii) about 300 to about 1,600 parts by weight of one or more plasticizing oils with a selected amount of at least one said plasticizing oil(s) having a viscosity of about 4 cSt at 40° C. and greaer; said gelatinous elastomer compositions characterized by a gel gram Bloom rigidity of about 20 to about 800 gram bloom; and in combination with or without
(iii) a selected amount of one or more polymers or copolymers of poly(styrene-butadiene-styrene), poly(styrene-butadiene)$_n$, poly(styrene-isoprene)$_n$, poly(styrene-ethylene-propylene), poly(styrene-ethylene-butylene), poly(styrene-ethylene-propylene)$_n$, poly(styrene-ethylene-butylene)$_n$, polystyrene, polybutylene, poly(ethylene-styrene), poly(ethylene-propylene), poly(ethylene-butylene), polypropylene, or polyethylene, wherein said selected copolymer is a linear, radial, star-shaped, branched or multiarm copolymer, wherein n is greater than one; and wherein said composite formed from the combination $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_{Mn}G_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, $M_nG_nM_nG_{nMn}G_n$, $G_nG_nM_nM_nG_n$, $G_nG_nM_nG_nM_nG_n$, a sequential addition or a permutation of one or more of said $G_n$ with one or more $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

8. A composite comprising a gel $G_n$ with a selected material $M_n$; said gel formed from
(i) 100 parts by weight of one or more block copolymers of poly(styrene-ethylene-ethylene-propylene-styrene), and from
(ii) about 300 to about 1,600 parts by weight of one or more plasticizing oils with a selected amount of at least one said plasticizing oil(s) having an average molecular weight of less than about 200 and greater; said gelatinous elastomer compositions characterized by a gel gram Bloom of about 20 to about 800 gram bloom; and in combination with or without
(iii) a selected amount of one or more polymers or copolymers of poly(styrene-butadiene-styrene), poly(styrene-butadiene)$_n$, poly(styrene-isoprene)$_n$, poly(styrene-ethylene-propylene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and wherein said composite formed from the combination $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_{Mn}G_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

9. A composite comprising a gel $G_n$ with a selected material $M_n$; said gel formed from
(i) 100 parts by weight of one or more block copolymers having a polyethylene midblock of the formula poly(styrene-ethylene-ethylene-propylene-styrene) exhibiting stress induced necking at high elongations not exhibited by gels having corresponding rigidity made from a poly(styrene-ethylene-butylene-styrene) or poly(styrene-ethylene-propylene-styrene) block copolymers wherein said block copolymer is a high viscosity copolymer having a viscosity value at 5 weight percent solution in toluene at 30° C. of about 90 cps and higher which corresponds to a viscosity at 10 weight percent of about 5800 cps and higher which corresponds to a viscosity at 20 weight percent solids solution in toluene at 25° C. of at about 80,000 cps and higher, and from
(ii) about 300 to about 1,600 parts by weight of one or more plasticizing oils with a selected amount of at least one said plasticizing oil(s) having an average molecular weight of less than about 200 to greater than about 700; said gelatinous elastomer compositions characterized by a gel gram Bloom of about 20 to about 800 gram bloom; and in combination with or without one or more of
(iii) a selected amount of one or more block copolymers of poly(styrene-butadiene-styrene), poly(styrene-butadiene)$_n$, poly(styrene-isoprene)$_n$, poly(styrene-ethylene-propylene )$_n$, or poly(styrene-ethylene-butylene)$_n$; a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene); a selected amount of a hydrocarbon resins including polystyrene, polypropylene, or polyethylene; a selected amount of polybutylene; a selected amount of rubbers of poly(ethylene-propylene) or poly(ethylene-butylene); a selected amount of a flame retardant; a selected amount of one or more internal and external non-adhering, non-sticking modifiers selected from amorphous silica, talc, zinc sterate, aluminum sterate, mica, and silicon dioxide; a selected amount of microspheres or aggregation of gas bubbles; a selected amount of microspheres or aggregation of gas bubbles; wherein said selected copolymer is a linear, radial, star-shaped, branched or multiarm copolymer, wherein n is greater than one; and wherein said composite formed from the combination $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_{Mn}G_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, $M_nG_nM_nG_{nMn}G_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

10. A composite comprising a gel $G_n$ with a selected material $M_n$; said gel formed from
  (i) 100 parts by weight of one or more block copolymers of poly(styrene-ethylene-ethylene-propylene-styrene), and from
  (ii) about 300 to about 1,600 parts by weight of one or more plasticizing oils with a selected amount of at least one said plasticizing oil(s) having a viscosity of about 4 cSt at 40° C. and greaer; said gelatinous elastomer compositions characterized by a gel gram Bloom of about 20 to about 800 gram bloom; and in combination with or without one or more of
  (iii) a selected amount of one or more block copolymers of poly(styrene-butadiene-styrene), poly(styrene-butadiene)$_n$, poly(styrene-isoprene)$_n$, poly(styrene-ethylene-propylene)$_n$, or poly(styrene-ethylene-butylene)$_n$; a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene); a selected amount of a hydrocarbon resins including polystyrene, polypropylene, or polyethylene; a selected amount of polybutylene; a selected amount of rubbers of poly(ethylene-propylene) or poly(ethylene-butylene); a selected amount of a flame retardant; a selected amount of one or more internal and external non-adhering, non-sticking modifiers selected from amorphous silica, talc, zinc sterate, aluminum sterate, mica, and silicon dioxide; a selected amount of microspheres or aggregation of gas bubbles; wherein said selected copolymer is a linear, radial, star-shaped, branched or multiarm copolymer, wherein n is greater than one; and wherein said composite formed from the combination $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_{Mn}G_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, $M_nG_nM_nG_{nMn}G_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

11. A composite comprising a gel $G_n$ with a selected material $M_n$; said gel formed from
  (i) 100 parts by weight of one or more block copolymers of poly(styrene-ethylene-ethylene-propylene-styrene), and from
  (ii) about 300 to about 1,600 parts by weight of one or more plasticizing oils with a selected amount of at least one said plasticizing oil(s) having a viscosity of about 4 cSt at 40° C. and greaer; said gelatinous elastomer compositions characterized by a gel gram Bloom of about 20 to about 800 gram bloom; and in combination with or without one or more of
  (iii) a selected amount of one or more block copolymers of poly(styrene-butadiene-styrene), poly(styrene-butadiene)$_n$, poly(styrene-isoprene)$_n$, poly(styrene-ethylene-propylene)$_n$, poly(ethylene-styrene), or poly(styrene-ethylene-butylene)n; a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene); a selected amount of a hydrocarbon resins including.polystyrene, polypropylene, or polyethylene; a selected amount of polybutylene; a selected amount of rubbers of poly(ethylene-propylene) or poly(ethylene-butylene); a selected amount of a flame retardant; a selected amount of non-adhering, non-sticking modifiers selected from amorphous silica, talc, zinc sterate, aluminum sterate, mica, and silicon dioxide; a selected amount of microspheres or aggregation of gas bubbles; wherein said selected copolymer is a linear, radial, star-shaped, branched or multiarm copolymer, wherein n is greater than one; and wherein said composite formed from the combination $G_nM_n$, $G_nM_nG_n$, $M_nG_nM_n$, $M_nG_nG_n$, $G_nG_nM_n$, $M_nM_nM_nG_nM_nM_n$, $M_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

12. A composite comprising a gel $G_n$ with a selected material $M_n$; said gel formed from
  (i) 100 parts by weight of one or more block copolymers poly(styrene-ethylene-ethylene-propylene-styrene), and from
  (ii) about 300 to about 1,600 parts by weight of one or more plasticizing oils with a selected amount of at least one said plasticizing oil(s) having a viscosity of about 4 cSt at 40° C. and greaer; said gelatinous elastomer compositions characterized by a gel gram Bloom of about 20 to about 800 gram bloom; and in combination with or without one more of (iii–xii):

(iii) a selected amount of one or more block copolymers of poly(styrene-butadiene-styrene), poly(styrene-butadiene)$_n$, poly(styrene-isoprene)$_n$, poly(styrene-ethylene-propylene)$_n$, poly(ethylene-styrene), or poly(styrene-ethylene-butylene)$_n$;

(iv) a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene);

(v) a selected amount of a hydrocarbon resins including polystyrene, polypropylene, or polyethylene, or polybutylene;

(vi) a selected amount of rubbers of poly(ethylene-propylene) or poly(ethylene-butylene);

(vii) a selected amount of a flame retardant;

(viii) a selected amount of non-adhering, non-sticking additives comprising antiblocking agents including tetrakis[methylene 3,-(3'5'-di-tertbutyl-4"-hydroxyphenyl)propionate]methane, octadecyl 3-(3", 5"-di-tert-butyl-4"-hydroxyphenyl)propionate, distearyl-pentaerythritol-diproprionate, thiodiethylene bis-(3,5-ter-butyl-4-hydroxy)hydrocinnamate, (1,3,5-trimethyl-2,4,6-tris[3,5-di-tert-butyl-4-hydroxybenzyl] benzene), 4,4"-methylenebis(2,6-di-tert-butylphenol), additives of stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes, and silicone fluids;

(ix) a selected amount of microspheres, aggregation of gas bubbles, or blowing agents;

(x) one or more additives selected from the group consisting of polyisobutylene including polybutene, hydrocarbon resins including polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon, polyalphamethylstyrene/vinyl toluene copolymer, polystyrene, and elastomeric diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-butadiene)$_n$, poly(styrene-isoprene)$_n$, poly(styrene-ethylene-propylene)$_n$, poly(styrene-ethylene-butylene)$_n$, poly(styrene-ethylene-propylene), poly(styrene-ethylene-butylene);

(xi) one or more additives selected from the group consisting of hydrocarbon resins, butyl rubber, polyisobutylene, additional block copolymers of poly(styrene-isoprene-styrene), poly(styrene-butadiene-styrene), poly(styrene-butadiene)$_n$, poly(styrene-isoprene)$_n$, poly(styrene-ethylene-propylene)$_n$, poly(styrene-ethylene-butylene)$_n$, polystyrene, polybutylene, poly(ethylene-propylene), poly(ethylene-butylene), polypropylene, polyethylene, diblock copolymers of poly(styrene-ethylene-propylene), poly(styrene-ethylene-butylene), stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes, and silicone fluids, magnetic particle materials, carbon blacks, silicon dioxide, silica, mica, talc, zinc sterate, amorphous silica, silica, silicon dioxide, aluminum sterate, fine metallic powder, metal flakes, clay, feldspar, glass microspheres, barium ferrite, wollastonite, hydrocarbon resins of polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon; wherein said selected copolymer is a linear, radial, star-shaped, branched or multiarm copolymer, wherein n is greater than one; and wherein said composite formed from the combination:

(xii) layers of $G_nM_n$, $M_nG_nM_n$, $M_nM_nG_n$, $M_nM_nG_nM_nM_n$, $G_nM_nG_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, and $G_nG_nM_nG_nM_nG_n$, a sequential addition or a permutation of one or more of said Gn with Mn; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

13. A composite comprising a gel $G_n$ with a selected material $M_n$, characterized by a gel gram Bloom rigidity of about 20 to about 1,800 gram bloom, said composite made from (i) 100 parts by weight of one or more block copolymers;

(ii) about 300 to about 1,600 parts by weight of one or more selected plasticizing oils with a selected amount of at least one said plasticizing oil(s) having a viscosity of about 4 cSt at 40° C. and greaer, with or without one or more of (iii) an additive;

wherein said (i), (ii), and (iii) are combined to form said gelatinous elastomeric composition; wherein said block copolymer comprises A—B—A blocks having a weight average molecular weight of at least about 300,000 or more corresponding to a measurable solution viscosity at 5 wt % solids in 95% toluene at 25° C. which solution remains a solid at 20 wt % solids in 80% toluene at 25° C. which corresponds to a viscosity value at 5 weight percent solution in toluene at 30° C. of about 90 cps and higher which corresponds to a viscosity at 10 weight percent of about 5800 cps and higher which corresponds to a viscosity at 20 weight percent solids solution in toluene at 25° C. of about 80,000 cps and higher; said A being selected from monoalkenylarene polymers including polystyrene; said B being a hydrogenated polymer comprising a plurality of covalently linked conjugated diene monomers including a hydrogenated polymer of isoprene/butadiene; wherein said (i) block copolymer is of the formula poly(styrene-ethylene-ethylene-propylene-styrene);

(1) said composite having layers of $G_nM_n$, $G_nM_nM_n$, or $M_nM_nG_nM_nM_n$, $M_nG_nM_n$, $G_nM_nG_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, or permutation of one or more of said $G_n$ with $M_n$; wherein said additive is:

(2) an additive selected from the group consisting of aggregation of gas bubbles formed by inert gases, and blowing agents including water, (3) an additive selected from the group consisting of internatal and external tack modifiers including, anti-blocking agents, non-adhering, non-sticking modifiers including tetrakis[methylene 3,-(3'5'-di-tertbutyl-4"-hydroxyphenyl)propionate]methane, octadecyl 3-(3", 5"-di-tert-butyl-4"-hydroxyphenyl)propionate, distearyl-pentaerythritol-diproprionate, thiodiethylene bis-(3,5-ter-butyl-4-hydroxy)hydrocinnamate, (1,3,5-trimethyl-2,4,6-tris[3,5-di-tert-butyl-4-hydroxybenzyl] benzene), 4,4"-methylenebis(2,6-di-tert-butylphenol), additives of stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes, mica, talc, zinc sterate, amorphous silica, silica, silicon dioxide, aluminum sterate, fine metallic powder, metal flakes, and silicone fluids, (4) an additive selected from the group consisting of polyisobutylene including polybutene, hydrocarbon resins including polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon, polyalphamethylstyrene/vinyl toluene copolymer, polystyrene, and elastomeric diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-butadiene)$_n$, poly(styrene-isoprene)$_n$, poly (styrene-ethylene-propylene)$_n$, or poly(styrene-ethylene-butylene)$_n$, poly(styrene-ethylene-propylene), poly(styrene-ethylene-butylene), (5) an additive selected from the group consisting of flame retardants, (6) an additive selected from the group consisting of hydrocarbon resins, polyisobutylene including polybutene, additional block copolymers of poly(styrene-isoprene-styrene), poly(styrene-butadiene-styrene), poly(styrene-butadiene)$_n$, poly(styrene-isoprene)$_n$, poly(styrene-ethylene-propylene)$_n$, poly(ethylene-styrene), poly(styrene-ethylene-butylene)$_n$, particulate fillers, microspheres, butadiene rubber, poly(ethylene/propylene), and poly(ethylene/butylene), (7) an additive selected from the group consisting of poly(styrene-butadiene-styrene), polystyrene, polybutylene, poly(ethylene-propylene), poly(ethylene-butylene), polypropylene, polyethylene, diblock copolymers of poly(styrene-butadiene)$_n$, poly(styrene-isoprene)$_n$, poly(styrene-ethylene-propylene), poly(styrene-ethylene-butylene), poly(styrene-ethylene-propylene)$_n$, poly(styrene-ethylene-butylene)$_n$, stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes, and silicone fluids, and (8) an additive selected from the group consisting of hydrocarbon resins of polystyrene, polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon, particulate fillers, and microspheres;

said gel having a hydrophobic or hydrophilic surface depending on said additive (3) selected.

14. A composite comprising a gel $G_n$ and selected material $M_n$, formed from
(i) 100 parts by weight of one or more block copolymers with a polyethylene midblock segment of the formula poly(styrene-ethylene-ethylene-propylene-styrene) exhibiting a measurable amount of polyethylene crystallinity characterized by stress induced crystallinity not exhibited by gels having corresponding rigidity made from a poly(styrene-ethylene-butylene-styrene) or poly(styrene-ethylene-propylene-styrene) block copolymers wherein said block copolymer is a high viscosity copolymer having a viscosity value at 5 weight percent solution in toluene at 30° C. of about 90 cps and higher which corresponds to a viscosity at 10 weight percent of about 5800 cps and higher which corresponds to a viscosity at 20 weight percent solids solution in toluene at 25° C. of at about 80,000 cps and higher, and from
(ii) about 300 to about 1,600 parts by weight of one or more plasticizing oils with a selected amount of at least one said plasticizing oil(s) having a viscosity of about 4 cSt at 40° C. and greater; said gelatinous elastomer compositions characterized by a gel gram Bloom of about 20 to about 800 gram bloom; and in combination with or without
(iii) a selected amount of one or more block copolymers of poly(styrene-butadiene-styrene), poly(styrene-butadiene)$_n$, poly(styrene-isoprene)$_n$, poly(styrene-ethylene-propylene)$_n$, or poly(styrene-ethylene-butylene)n; a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene); a selected amount of a hydrocarbon resins including polystyrene, polypropylene, or polyethylene; a selected amount of polybutylene; a selected amount of rubbers of poly(ethylene-propylene) or poly(ethylene-butylene); a selected amount of a flame retardant; a selected amount of non-adhering, non-sticking modifiers; a selected amount of microspheres or aggregation of gas bubbles; wherein said selected copolymer is a linear, radial, star-shaped, branched or multiarm copolymer, wherein n is greater than one; and wherein said composite formed from the combination $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_n$ $G_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

15. A composite of claim 7, shaped in the form of a gel liner for lower extremity, above or below the knee prosthesis devices as described by one or more codes L5664, L5665, or L5667 of the American Orthotic and Prosthetic Association, said gel liner formed by injection molding, extruding, spinning, casting, or dipping of said gel $G_n$ of selected rigidity with a selected said material $M_n$.

16. A composite of claim 8, shaped in the form of a gel liner for lower extremity, above or below the knee prosthesis devices as described by one or more codes L5664, L5665, or L5667 of the American Orthotic and Prosthetic Association, said gel liner formed by injection molding, extruding, spinning, casting, or dipping of said gel $G_n$ of selected rigidity with a selected said material $M_n$.

17. A composite of claim 7, wherein said composite being formed into a composite article into a gel hand exercising grip, a gel shape floss suitable for use as a dental floss, a gel crutch cushion, a gel cervical pillow, a gel bed wedge pillow, a gel leg rest, a gel neck cushion, a gel mattress, a gel bed pad, a gel elbow pad, a gel dermal pad, a gel wheelchair cushion, a gel helmet liner, a gel cold and hot pack, a gel exercise weight belt, a gel traction pad or belt, a gel cushion for splints, a gel sling, a gel brace for the hand, wrist, finger, forearm, knee, leg, clavicle, shoulder, foot, ankle, neck, back, rib, a gel sole for orthopedic shoe, a gel shaped toy article, a gel optical cladding for cushioning optical fibers from bending stresses, a gel swab tip, a gel fishing bait, a gel seal against pressure, a gel thread, a gel strip, a gel yarn, a gel tape, a weaved gel cloth, a gel fabrics, a gel balloon for valvuloplasty of the mitral valve, a gel trointestinal balloon dilator, a gel esophageal balloon dilator, a gel dilating balloon catheter use in coronary angiogram, a gel condom, a gel toy balloon, a gel surgical and examination glove, a self sealing enclosures for splicing electrical and telephone cables and wires, a gel film, or a gel liner.

* * * * *

UNITED STATES PATENT AND TRADEMARK OFFICE
CERTIFICATE OF CORRECTION

| | |
|---|---|
| PATENT NO. | : 6,867,253 C1 |
| APPLICATION NO. | : 90/011018 |
| DATED | : March 15, 2005 |
| INVENTOR(S) | : John Y. Chen |

It is certified that error appears in the above-identified patent and that said Letters Patent is hereby corrected as shown below:

Col. 54-55, delete claim 1:

"1. A composite comprising: a gel denoted by G, being [in adherent contact, adhesive contact, clinging contact, fastening contact, sticking contact, or]*formed by heat into a composite* in physical contact with a selected material M forming the combination $G_n M_n$, $G_n M_n G_n$, $M_n G_n M_n$, $M_n G_n G_n M_n$, $G_n M_n M_n G_n$, $G_n M_n G_n M_n G_n M_n M_n M_n G_n M_n M_n M_n G_n M_n M_n M_n$ or a permutation of one or more of said $G_n$ with $M_n$; wherein when n is a subscript of M, n is the same or different selected from the group consisting of paper, foam, plastic, fabric, metal, metal foil, [metalic flakes,]concrete, wood, glass, [glass fibers]ceramics, synthetic resin, synthetic fibers or refractory materials; and wherein when n is a subscript of G, n denotes the same or a different gel rigidity; said gel comprising: (i) 100 parts by weight of one or more block copolymers selected from poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-propylene-ethylene-styrene), poly(styrene-ethylene-ethylene-butylene)$_n$; [poly(styrene-ethylene-ethylene-propylene)$_n$,] poly(styrene-ethylene-ethylene-butylene$_{25}$)$_n$, [poly(styrene-ethylene-propylene-ethylene)$_n$,]or mixtures thereof, wherein subscript n is two or more; (ii) about 300 to about 1,600 parts by weight of one or more plasticizing oils with a selected amount of at least one said plasticizing oil(s) having a viscosity [of about]*greater than* 4 cSt at 40° C. [and greater]; said gel characterized by a gel gram Bloom of about 2 gram to about 1,800 gram Bloom; and in combination with or without (iii) a selected amount of one or more polymers or copolymers comprising poly(styrene-butadiene-styrene), poly(styrene-butadiene)$_n$, poly(styrene-isoprene)$_n$, poly(ethylene-styrene), poly(styrene-ethylene-propylene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; said gel having greater tear resistance than gels having corresponding rigidity made from a poly(styrene-ethylene-butylene-styrene) or poly(styrene-ethylene-propylene-styrene) block copolymers."

Signed and Sealed this
Twenty-sixth Day of July, 2011

David J. Kappos
*Director of the United States Patent and Trademark Office*

CERTIFICATE OF CORRECTION (continued)
U.S. Pat. No. 6,867,253 C1

Col. 54-55, claim 1 should read as follows:

-- 1. A composite comprising: a gel denoted by G, being *formed by heat into a composite* [in adherent contact, adhesive contact, clinging contact, fastening contact, sticking contact, or] in physical contact *and physically interlocked* with a selected material M forming the combination $G_n M_n$, $G_n M_n G_n$, $M_n G_n M_n$, $M_n G_n G_n M_n$, $G_n M_n M_n G_n$, $G_n M_n G_n M_n G_n$, $M_n M_n M_n G_n$, $M_n M_n M_n G_n M_n M_n M_n$ or a permutation of one or more of said $G_n$ with $M_n$; wherein when n is a subscript of M, n is the same or different selected from the group consisting of paper, foam, plastic, fabric, metal, metal foil, [metalic flakes,] concrete, wood, glass, [glass fibers,] ceramics, synthetic resin, synthetic fibers or refractory materials; and wherein when n is a subscript of G, n denotes the same or a different gel rigidity; said gel comprising: (i) 100 parts by weight of one or more block copolymers selected from poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-propylene-ethylene-styrene), poly(styrene-ethylene-ethylene-butylene)$_n$, [poly(styrene-ethylene-ethylene-propylene)$_n$,] poly(styrene-ethylene-ethylene-butylene$_{25}$)$_n$, [poly(styrene-ethylene-propylene-ethylene)$_n$,]or mixtures thereof, wherein subscript n is two or more; (ii) about 300 to about 1,600 parts by weight of one or more plasticizing oils with a selected amount of at least one said plasticizing oil(s) having a viscosity *greater than* [of about] 4 cSt at 40° C. [and greater]; said gel characterized by a gel gram Bloom of about 2 gram to about 1,800 gram Bloom; and in combination with or without (iii) a selected amount of one or more polymers or copolymers comprising poly(styrene-butadiene-styrene), poly(styrene-butadiene)$_n$, poly(styrene-isoprene)$_n$, poly(ethylene-styrene), poly(styrene-ethylene-propylene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; said gel having greater tear resistance than gels having corresponding rigidity made from a poly(styrene-ethylene-butylene-styrene) or poly(styrene-ethylene-propylene-styrene) block copolymers. --

Col. 55, delete claim 2:

"2. A composite comprising: a gel denoted by G, being *formed by heat into a composite* [in adherent contact, adhesive contact, clinging contact, fastening contact, sticking contact, or] in physical contact with a selected material M or in combination with one or more of the same gel or a different gel forming a composite of the combination $G_n G_n$, $G_n G_n G_n$, $G_n M_n$, $G_n M_n G_n$, $M_n G_n M_n$, $M_n G_n G_n$, $M_n M_n M_n G_n M_n$, $M_n G_n G_n M_n$, $G_n M_n G_n G_n$, $G_n G_n M_n M_n$, $G_n M_n M_n G_n$, $G_n G_n M_n G_n M_n G_n G_n$, $G_n M_n G_n M_n M_n$, $M_n G_n M_n G_n M_n G_n$, $G_n G_n M_n M_n G_n$, $G_n G_n M_n G_n M_n$, $G_n G_n M_n G_n M_n G_n$, $G_n M_n G_n M_n G_n$, $M_n M_n M_n G_n$, $M_n M_n M_n G_n M_n M_n M_n$ or a permutation of one or more of said $G_n$ with $M_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity; said gel comprising: (i) 100 parts by weight of one or more block copolymers selected from poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-propylene-ethylene-styrene), poly(styrene-ethylene-ethylene-butylene)$_n$, [poly(styrene-ethylene-ethylene-propylene)$_n$,] poly(styrene-ethylene-ethylene-butylene$_{25}$)$_n$, [poly(styrene-ethylene-propylene-ethylene)$_n$,] or mixtures thereof, wherein subscript n is two or more; (ii) about 300 to about 1,600 parts by weight of one or more plasticizing oils with a selected amount of at least one said plasticizing oil(s) having an average molecular weight of about 200 and greater; said gel characterized by a gel gram Bloom of about 2 gram to about 1,800 gram Bloom; and in combination with or without (iii) a selected amount of one or more polymers or copolymers comprising poly(styrene-butadiene-styrene), poly(styrene-butadiene)$_n$, poly(styrene-isoprene)$_n$, poly(styrene-ethylene-propylene), poly(ethylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; said gel having greater fatigue resistance than gels having corresponding rigidity made from a poly(styrene-ethylene-butylene-styrene) or poly(styrene-ethylene-propylene-styrene) block copolymers."

Col. 55, claim 2 should read as follows:

-- 2. A composite comprising: a gel denoted by G, being *formed by heat into a composite* [in adherent contact, adhesive contact, clinging contact, fastening contact, sticking contact, or] in physical contact *and physically interlocked* with a selected material M or in combination with one or more of the same gel or a different gel forming a composite of the combination $G_n\ G_n$, $G_n\ G_n\ G_n$, $G_n\ M_n$, $G_n\ M_n\ G_n$, $M_n\ G_n\ M_n$, $M_n\ G_n\ G_n$, $M_n\ M_n\ M_n\ G_n\ M_n$, $M_n\ G_n\ G_n\ M_n$, $G_n\ M_n\ G_n\ G_n$, $G_n\ G_n\ M_n\ M_n$, $G_n\ M_n\ M_n\ G_n$, $G_n\ G_n\ M_n\ G_n\ M_n\ G_n\ G_n$, $G_n\ M_n\ G_n\ M_n\ M_n$, $M_n\ G_n\ M_n\ G_n\ M_n\ G_n$, $G_n\ G_n\ M_n\ M_n\ G_n$, $G_n\ G_n\ M_n\ G_n\ M_n$, $G_n\ G_n\ M_n\ G_n\ M_n\ G_n$, $G_n\ M_n\ G_n\ M_n\ G_n$, $M_n\ M_n\ M_n\ G_n$, $M_n\ M_n\ M_n\ G_n\ M_n\ M_n\ M_n$ or a permutation of one or more of said $G_n$ with $M_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity; said gel comprising: (i) 100 parts by weight of one or more block copolymers selected from poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-propylene-ethylene-styrene), poly(styrene-ethylene-ethylene-butylene)$_n$, [poly(styrene-ethylene-ethylene-propylene)$_n$,] poly(styrene-ethylene-ethylene-butylene$_{25}$)$_n$, [poly(styrene-ethylene-propylene-ethylene)$_n$,] or mixtures thereof, wherein subscript n is two or more; (ii) about 300 to about 1,600 parts by weight of one or more plasticizing oils with a selected amount of at least one said plasticizing oil(s) having an average molecular weight of about 200 and greater; said gel characterized by a gel gram Bloom of about 2 gram to about 1,800 gram Bloom; and in combination with or without (iii) a selected amount of one or more polymers or copolymers comprising poly(styrene-butadiene-styrene), poly(styrene-butadiene)$_n$, poly(styrene-isoprene)$_n$, poly(styrene-ethylene-propylene), poly(ethylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; said gel having greater fatigue resistance than gels having corresponding rigidity made from a poly(styrene-ethylene-butylene-styrene) or poly(styrene-ethylene-propylene-styrene) block copolymers. --

(12) EX PARTE REEXAMINATION CERTIFICATE (8314th)
United States Patent
Chen

(10) Number: US 6,867,253 C1
(45) Certificate Issued: Jun. 7, 2011

(54) TEAR RESISTANT, CRYSTALLINE MIDBLOCK COPOLYMER GELS AND ARTICLES

(76) Inventor: John Y. Chen, Pacifica, CA (US)

Reexamination Request:
No. 90/011,018, May 28, 2010

Reexamination Certificate for:
Patent No.: 6,867,253
Issued: Mar. 15, 2005
Appl. No.: 09/721,213
Filed: Nov. 21, 2000

Related U.S. Application Data

(63) Continuation-in-part of application No. 09/285,809, filed on Apr. 1, 1999, now abandoned, and a continuation-in-part of application No. 09/274,498, filed on Mar. 28, 1999, now Pat. No. 6,420,475, and a continuation-in-part of application No. 09/130,545, filed on Aug. 8, 1998, now Pat. No. 6,627,275, and a continuation-in-part of application No. 08/984,459, filed on Dec. 3, 1997, now Pat. No. 6,324,703, and a continuation-in-part of application No. 08/909,487, filed on Jul. 12, 1997, now Pat. No. 6,050,871, and a continuation-in-part of application No. 08/863,794, filed on May 27, 1997, now Pat. No. 6,117,176, and a continuation-in-part of application No. PCT/US97/17534, filed on Sep. 30, 1997, and a continuation-in-part of application No. 08/719,817, filed on Sep. 30, 1996, now Pat. No. 6,148,830, and a continuation-in-part of application No. 08/665,343, filed on Jun. 17, 1996, which is a continuation-in-part of application No. 08/612,586, filed on Mar. 8, 1996, now Pat. No. 6,552,109, and a continuation-in-part of application No. PCT/US94/04278, filed on Apr. 19, 1994, and a continuation-in-part of application No. PCT/US94/07314, filed on Jun. 27, 1994, and a continuation-in-part of application No. 08/288,690, filed on Aug. 11, 1994, now Pat. No. 5,633,286, and a continuation-in-part of application No. 08/581,188, filed on Dec. 29, 1995, and a continuation-in-part of application No. 08/581,191, filed on Dec. 29, 1995, now Pat. No. 5,760,117, and a continuation-in-part of application No. 08/581,125, filed on Dec. 29, 1995, now Pat. No. 5,962,527, which is a continuation-in-part of application No. 08/288,690, and a continuation-in-part of application No. PCT/US94/07314, which is a continuation-in-part of application No. PCT/US94/04278, said application No. 08/581,191, is a continuation-in-part of application No. 08/288,690, and a continuation-in-part of application No. PCT/US94/07314, which is a continuation-in-part of application No. PCT/US94/04278.

(51) Int. Cl.
| A61C 15/00 | (2006.01) |
|---|---|
| A61C 15/04 | (2006.01) |
| C08L 51/00 | (2006.01) |
| C08L 53/00 | (2006.01) |
| C08L 53/02 | (2006.01) |

(52) U.S. Cl. .................. 524/505; 524/507; 524/508; 524/513; 524/515; 623/59; 623/61; 623/63

(58) Field of Classification Search .................. None
See application file for complete search history.

(56) References Cited

U.S. PATENT DOCUMENTS

| 3,676,387 A | 7/1972 | Lindlof |
|---|---|---|
| 3,827,999 A | 8/1974 | Crossland |
| 4,369,284 A | 1/1983 | Chen |
| 4,842,931 A | 6/1989 | Zook |
| 4,942,270 A * | 7/1990 | Gamarra ..................... 174/93 |
| 5,442,004 A | 8/1995 | Sutherland et al. |
| 5,603,122 A | 2/1997 | Kania |
| 5,633,286 A | 5/1997 | Chen |
| 5,760,117 A | 6/1998 | Chen |
| 5,830,237 A | 11/1998 | Kania |
| 5,884,639 A | 3/1999 | Chen |
| 5,962,572 A | 10/1999 | Chen |
| 6,117,176 A | 9/2000 | Chen |
| 6,148,830 A | 11/2000 | Chen |
| 6,324,703 B1 | 12/2001 | Chen |
| 6,420,475 B1 | 7/2002 | Chen |
| 6,552,109 B1 | 4/2003 | Chen |
| 6,627,275 B1 | 9/2003 | Chen |

FOREIGN PATENT DOCUMENTS

| EP | 108518 A2 * | 5/1984 |
|---|---|---|
| WO | 199323472 | 11/1993 |
| WO | 199629033 | 9/1996 |

OTHER PUBLICATIONS

US Securities Exchange Commission Form 10–K Dec. 31, 2004 Langer, Inc. pp. 1, 4, & 24.
Kania Declaration in Reexam 90/008,277 From Pair File Dec. 28, 2007 pp. 1–5.
ANTEC '99 Proceedings Deited by SPE Staff/pp. 1725. PW–90 Oil, (1999).
Septon Technical Information G–3–4 Dec. 3, 1992 Kuraray Co., Ltd., Property of Septon–4055, Septon 8008/oil Compound.
Septon 4055 Material Safety Data Sheet, dated Apr. 25, 1991.
Affidavit of Septon Company of America, *Edizone* v. *Cloud Nine,* Civil Case No. 1:04cv00117TS, Oct. 11, 2006.
EPA Premanufacture Notice for Septon 4055, dated Aug. 10, 1990.
Septon 4055 Material Safety Data Sheet, dated May 1, 1995.
Septon 4055 Material Safety Data Sheet, dated Apr. 30, 2001.
Prosthetics/Orthotics Silipos Advanced Polymer Technology of SEBS tri–block polymer gel product catalogue (4 bi–folds Knit–Rite distribution date of 1993).

* cited by examiner

*Primary Examiner* — Alan Diamond

(57) ABSTRACT

Novel gels and articles are formed from one or more multi-block copolymers having at least one block segment of poly (ethylene) and selected amounts of one or more low viscosity plasticizers, said gels having an amount of crystallinity, glassy components, selected amounts of plasticizers, with or without other additives sufficient to achieve improvements in one or more physical properties including improved crack propagation resistance, improved tea resistance, improved resistance to fatigue and resistance to catastrophic failure not obtainable in amorphous gels and exceptionally lower and/or no tack.

_US 6,867,253 C1_

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE
SPECIFICATION AFFECTED BY AMENDMENT
ARE PRINTED HEREIN.

Column 37, after line 18:

*An example of the above mentioned toy is a Humdinger spinning toy of the related co-pending filed patent application Ser. No. 08/211,781 filed PCT on Apr. 19, 1994, now U.S. Patent 6,033,283 and incorporated in US 6,867,253 by reference, which describes the structure and operation of Humdinger spinning toy as follows:*

*When a gel body is set into rotation of at least 100 r.p.m. (revolutions per minute) to as high as 1,000 r.p.m. and higher, the forces can be significant. The following examples can best illustrate the forces involved.*

*The inward pulling forces generated by a pair of twisting stings as measured on a spring scale for a 2.00" (5.08 mm) dia. times.0.50" (12.70 mm) thickness spinning circular gel body can range from an extreme of less than one pound to forty pounds and greater. The typical range for such a spinning gel body may range from between less than five pounds to twenty pounds and greater. As another example, the measured pulling forces for a (smaller) 1.75" (44.46 mm) dia..times.0.60" (15.24 mm) spinning circular gel body can range from an extreme of less than one pound to twenty-five pounds and greater. The typical range for such as a smaller body is between less than three pounds to about eight pounds and greater.*

*For the purpose of the invention, an indirect measure of the shearing forces generated during play is measured (in pounds) by the inward pulling forces of the twisting strings 5 on a spring balance during dynamic spinning. The typical values can range from less than one pound to fifty pounds and greater. String puling forces for various shapes (large and small) of spinning bodies having measured values of 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 . . . 40, 50, 60, 70, 80 pounds and greater can be achieved and such values are typical. During spinning, the measured pulling force is read as a dynamic measurement which starts from a low value and rise as the string(s) are pulled apart forcing the body to reaching a maximum spin rate (i.e. maximum measured pulling force value).*

*The dynamic variables due to the centrifugal force of rotation of the bodies, such as elongation, stress and shear forces, under extreme high torque conditions, and the accelerations and de-accelerations involved are ever changing during play.*

*The bodies of the invention when rotated about an axis of rotation will experiece increased deformation from their original shapes with increase rates of rotation. Irrespective of the original shapes of the bodies, when subjected to rotation forces, the bodies will deform in a highly elastic, predetermined, non-uniform, and non-radial manner. Because of the high deformations resulting from rotational forces, the bodies 2 will distribute their mass outwardly by elongating perpendicularly with respect to its axis of rotation. The gel material at the extreme outer parts (equator) of the bodies will experience greater and greater centrifugal force as the bodies rotate and elongate more and more. The bodies if not properly designed will be pulled apart by the increasing centrifugal force of rotation. For example, the centrifugal force of a rotating body having a mass of about 50 grams and an elongated mass about the body's equator of about 10 centimeter may produce from less than about 50 to at about 250 pound-force or higher.*

*If the hole separation distance is zero, then the torque will also be zero. Therefore, a suitable separation distance is needed to separate the holes from each other and the holes 6 from the selected axis of rotation. The holes should be separated approximately equal distance from the axis of rotation. A suitable distance, x, may be selected based on various factors, including the moment of inertia, axis of rotation, and the necessary torque need to rotate the bodies about its axis of rotation by the action of the twisting string. If the separations between the holes with respect to the axis of rotation is slightly off, then the torque applied to the bodies will be unbalanced. The unbalanced rotation would not be totally disastrous, but may produce a desirable off-balanced effect. While the humdinger may still adequately operate, it will be more difficult to keep the wobbling humdinger rotating in the unbalanced state.*

*As the bodies rotate, the moment of inertia will change and the point of the applied torque will also change. The moment of inertia of the bodies changes because the shape of the bodies changes with increased rate of rotation. Due to the highly elastic nature of the gel bodies, as their shape changes, so will the position of the holes with respect to each other and with respect to their distances from the axis of rotation. Any off-centering of the placement of the holes with respect to the axis of rotation will be greatly magnified by the centrifugal force acting on the body, since the original placement of the holes will aslo be changed due to elastic stretching. The torque acting on the bodies will greatly vary as the centrifugal force further separates the holes 6 from each other and from the axis of rotation.*

*Moreover, the over all original shape of a body will also affect the position of the holes as the body is set into rotation. The change in separations between the holes and the change in distance between the holes and the axis of rotation due to the centrifugal force acting on the body is also affected by the shape of the original body as a whole. In other words, the configuration of the original shape of the elastic body directly affects the amount and direction of the elastic deformation about the holes caused by the centrifugal force. A stretching or elastic deformation of one part of a body will directly affect other parts of the body as well. Therefore, any deformation by an applied force on any part of the body will correspondingly cause deformation to other parts of the body. The holes and the shape of the bodies are always in a state of flux due to the forces generated during rotation. The holes freely move about as the shape of the body is changed by the force of rotation. This is the nature of bodies under dynamic motion as opposed to rigid bodies.*

*The string is passed through the two holes of the gel body and tied into a loop. For gel bodies having three or more holes, the individual strings may be passed through the holes and tied together at opposite ends. The gel body is set into continuous alternating rotating motion with an initial twirl of the body followed by alternately pulling and releasing the* string while holding it in opposite directions which keeps it spinning. Between the second and fourth full reversal of rotation of the gel body, the string will have sufficient twist to shear off, and cut into or through the gel material separating the holes. Gel material of low strength cannot resist the tremendous shearing action of the twisting strings between the holes. The twisting action of the strings generated by the spinning gel body can exhibit a first order twist, a second order twist, or higher order twists. A first order twist refers to one or more twists of a pair of strings (i.e. a pair of strings when twisted together forms a small tight binding helix). A second order twist refers to one or more large binding helixes built up by a pair of strings that have been twisted beyond the maximum number of twists which normally produces small tight binding helixes of the first order kind. Similarly, a third order twist refers to a much larger tightly binding helix built up by the maximum number of second order twists produced by the pair of twisting strings. The third order twist may be manifested by the appearance of a branch of two or more twist of the first order twisting strings.

The shear force created by the static twisting of the string, however, is substantially different than the shear force generated under dynamic twisting of the strings. This can be demonstrated by taking a sample of any of the soft gel bodies and subject it to static twisting between a pair of strings under a static spring load of 20, 30, and 40 lbs for twenty four hours and compare the condition of the sample to samples of the same gel body subject under dynamic twist spring load of less than 20 lbs. (e.g. 5, 8, 10, 12, 16, 18, etc.). The results show that the shear force produce by a dynamic twist spring load of less than 20 lbs will easily cut a soft gel body or any low strength material body while the same sample will remain substantially uncut under a higher static twist spring load. Therefore, it is important to take into consideration the drastic effects of the shear force produced by the dynamic twisting of a pair of strings.

Suitable interlocking materials (that helps resist the shear force of the twisting strings) for use in the humdingers of the invention include: open cell foams, other polymeric or elastomeric (Kraton) materials, porous materials, multi-layered coatings, and single layered, and composite layered materials. As an example, opened cell foam when dipped into the instant composition will form an interpenetrating physical networks (interlocking of gel composition and foam composite). Such composite will exhibit greater rigidity and resistance to the shear force generated by a first, a second, a third, or a higher order dynamic twisting of a pair of strings. Furthermore, the interlocking materials surrounding the holes of the gel bodies may be made from flexible materials, such as fibers and fabrics of cotton, flax, and silk. Other flexible materials include: elastomers, fiber-reinforced composites, mohair, and wool. Useful synthetic fibers include: acetate, acrylic, aramid, glass, modacrylic polyethylene, nylon, olefin, polyester, rayon, spandex, carbon, sulfar, polybenzimidazole, and combinations of the above.

As taught in parent patent US 6,033,283, the following commercial elastomers can be formed with oil and in combination with other polymers into suitable gels for use in making the bodies of the invention, which includes Kuraray (SEP), (SEPS) or (SEB/EPS) Nos. 1001 (SEP), 2002 (SEPS), 2063 (SEPS), 2023 (SEPS), 2043 (SEPS), 2063 (SEPS), 2005 (SEPS), 2006 (SEPS), 2050 (SEPS), 2103 (SEPS), 2104 (SEPS), 2105 (SEPS), and 4055 (SEB/EPS) (styrene-ethylene-butylene/ethylene-propylene-styrene) block polymer made from hydrogenated styrene isoprene/butadiene styrene block copolymer or more specifically made from hydrogenated styrene block polymer with 2-methyl-1,3-butadiene and 1,3-butadiene. Where the ethylene (E) of the ethylene-butylene (EB) segment of the midblock (EB/EP) of the (SEB/EPS) block polymer is substantially greater than butylene (B) so as to exhibit ethylene crystallinity, (SEB/EPS) may be denoted as (SE/EPS) or denoted as (SEEPS) block polymer for the sake of simplicity.

In the operation of the humdingers of the invention, the string's twisting action imparts rotation to the gel body so as to elongate the gel body during rotation. The elongated gel body will reach a maximum elongation due to centrifugal force of 50% or more. Elongations of 100%, 200%, 300%, 400%, 500%, 600%, 700% and higher are possible depending on the amount of tension of the pull of the humdinger's strings. Gel bodies of the invention can be designed to withstand elongations higher than 1,000%, which can occur at extreme high rates of rotation of 500 r.p.m. and higher. Spinning rates can span from a low of 10 r.p.m. to a high of over 1,000 r.p.m. Spinning rates of 50, 100, 150, 200, 25, 300, 350, 400, 500, 600, 700, 800, 900, 1,000, 1,200, and 1,400 r.p.m. values are routinely achieved.

The operation of the humdingers of the invention can be ready observed under strobe light. The number of revolutions per minute may be counted in this way. The changes in radius can be measured. The change in gel body shape can be observed and measured. The centrifugal force acting on the rotating gel body can be likewise determined at any instant of time, at any instant rate of rotation, and at any instant change in gel body shape. The perpendicular-axis elongation effect of the gel body can be viewed under strobe light; its regions of deformation and re-distribution of mass can be viewed, measured and readily determined by ruled grid markings on the gel body.

AS A RESULT OF REEXAMINATION, IT HAS BEEN DETERMINED THAT:

Claims 1, 2, 7, 8, 10-12 and 14 are determined to be patentable as amended.

Claims 3-5 and 15-17, dependent on amended claim, are determined to be patentable.

New claims 18-20 are added and determined to be patentable.

Claims 6, 9 and 13 were not reexamined.

1. A composite comprising: a gel denoted by G, being [in adherent contact, adhesive contact, clinging contact, fastening contact, sticking contact, or] *formed by heat into a composite* in physical contact with a selected material M forming the combination $G_n M_n$, $G_n M_n G_n$, $M_n G_n M_n$, $M_n G_n G_n M_n$, $G_n M_n M_n G_n$, $G_n$, $M_n G_n M_n G_n M_n M_n M_n G_n M_n M_n M_n G_n M_n M_n M_n$ or a permutation of one or more of said $G_n$ with $M_n$; wherein when n is a subscript of M, n is the same or different selected from the group consisting of paper, foam, plastic, fabric, metal, metal foil, [metalic flakes,] concrete, wood, glass, [glass fibers,] ceramics, synthetic resin, synthetic fibers or refractory materials; and wherein when n is a subscript of G, n denotes the same or a different gel rigidity; said gel comprising: (i) 100 parts by weight of one or more block copolymers selected from poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-propylene-ethylene-styrene), poly(styrene-ethylene-ethylenebutylene)$_n$; [poly(styrene-ethylene-ethylene-propylene)$_n$,] poly(styrene-ethylene-ethylene-butylene$_{25}$)$_n$, [poly(styrene-ethylene-propylene-ethylene)$_n$,] or mixtures thereof, wherein subscript n is two or more; (ii) about 300 to about 1,600 parts by weight of one or more plasticizing oils with a selected amount of at least one said plasticizing oil(s) having a viscosity [of about] *greater than* 4 cSt at 40° C. [and greater]; said gel characterized by a gel gram Bloom of about 2 gram to about 1,800 gram Bloom; and in combination with or without (iii) a selected amount of one or more polymers or copolymers comprising poly(styrene-butadiene-styrene), poly(styrene-butadiene)$_n$, poly(styrene-isoprene)$_n$, poly(ethylene-styrene), poly(styrene-ethylene-propylene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; said gel havig greater tear resistance than gels having corresponding rigidity made from a poly(styrene-ethylene-butylene-styrene) or poly(styrene-ethylene-propylene-styrene) block copolymers.

2. A composite comprising: a gel denoted by G, being [in adherent contact, adhesive contact, clinging contact, fastening contact, sticking contact, or] *formed by heat into a composite* in physical contact with a selected material M or in combination with one or more of the same gel or a different gel forming a composite of the combination $G_n\ G_n$, $G_n\ G_n$ $G_n$, $G_n\ M_n$, $G_n\ M_n\ G_n$, $M_n\ G_n\ M_n$, $M_n\ G_n\ G_n$, $M_n\ M_n\ M_n\ G_n$ $M_n$, $M_n\ G_n\ G_n\ M_n$, $G_n\ M_n\ G_n\ G_n$, $G_n\ G_n\ M_n\ M_n$, $G_n\ M_n\ M_n$ $G_n$, $G_n\ G_n\ M_n\ G_n\ M_n\ G_n\ G_n$, $G_n\ M_n\ G_n\ M_n\ M_n$, $M_n\ G_n\ M_n\ G_n$ $M_n\ G_n$, $G_n\ G_n\ M_n\ M_n\ G_n$, $G_n\ G_n\ M_n\ G_n\ M_n$, $G_n\ G_n\ M_n\ G_n\ M_n$ $G_n$, $G_n\ M_n\ G_n\ M_n\ G_n$, $M_n\ M_n\ M_n\ G_n$, $M_n\ M_n\ M_n\ G_n\ M_n\ M_n$ $M_n$ or a permutation of one or more of said $G_n$ with $M_n$; wherein when n is a subscript of M, n is the same or different selected from the group consisting of paper, foam, plastic, fabric, metal, metal foil, concrete, wood, glass, glass fibers, ceramics, synthetic resin, synthetic fibers or refractory materials; and wherein when n is a subscript of G, n denotes the same or a different gel rigidity; said gel comprising: (i) 100 parts by weight of one or more block copolymers selected from poly(styrene-ethylene-ethylene-butylene-styrene), poly(styrene-ethylene-ethylene-propylene-styrene), poly(styrene-ethylene-ethylene-butylene$_{25}$-styrene), poly(styrene-ethylene-propylene-ethylene-styrene), poly(styrene-ethylene-ethylene-butylene)$_n$, [poly(styrene-ethylene-ethylene-propylene)$_n$,] poly(styrene-ethylene-ethylene-butylene$_{25}$)$_n$, [poly(styrene-ethylene-propylene-ethylene)$_n$,] or mixtures thereof, wherein subscript n is two or more; (ii) about 300 to about 1,600 parts by weight of one or more plasticizing oils with a selected amount of at least one said plasticizing oil(s) having an average molecular weight of about 200 and greater; said gel characterized by a gel gram Bloom of about 2 gram to about 1,800 gram Bloom; and in combination with or without (iii) a selected amount of one or more polymers or copolymers comprising poly(styrene-butadiene-styrene), poly(styrene-butadiene)$_n$, poly(styrene-isoprene)$_n$, poly(styrene-ethylene-propylene), poly(ethylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; said gel havig greater tear resistance than gels having corresponding rigidity made from a poly(styrene-ethylene-butylene-styrene), or poly(styrene-ethylene-propylene-styrene) block copolymers.

7. A composite comprising a gel $G_n$ which is *formed into a composite by heat and physically interlocked* with a selected material $M_n$, said gel formed from (i) 100 parts by weight of one or more block copolymers of the formula poly(styrene-ethylene-ehtylene-propylene-styrene) having greater tear resistance than a gel of corresponding rigidity made from a poly(styrene-ethylene-propylene-styrene), block copolymer, wherein said (i) block copolymer is a high viscosity copolymer having a viscosity value at 5 weight percent solution in toluene at 30° C. of about 90 mPa.S and higher which corresponds to a viscosity at 10 weight percent of about 5800 mPa.S and higher which corresponds to a viscosity at 20 weight percent solids solution in toluene at 25° C. of at about 80,000 mPa.S and higher, and from (ii) about 300 to about 1,600 parts by weight of one or more plasticizing oils with a selected amount of at least one said plasticizing oil(s) having a viscosity [of about] *greater than* 4 cSt at 40° C. [and greaer]; said gelatinous elastomer compositions characterized by a gel gram Bloom rigidity of about 20 to about 800 gram bloom; and in combination with or without (iii) a selected amount of one or more polymers or copolymers of poly(styrene-butadiene-styrene), poly(styrene-butadiene)$_n$, poly(styrene-isoprene)$_n$, poly(styrene-ethylene-propylene), poly(styrene-ethylene-butylene), poly(ethylene-styrene-)$_n$, poly(styrene-ethylene-butylene)$_n$, polystyrene, polybutylene, poly(styrene-ethylene-propylene), poly(ethylene-propylene), poly(ethylene-butylene), polypropylene, or polyethylene, wherein said selected copolymer is a linear, radial, star-shaped, branched or multiarm copolymer, wherein n is greater than one; and wherein said composite formed from the combination $G_n\ M_n$, $G_n\ M_n\ G_n$, $M_n\ G_n\ M_n$, $M_n\ G_n\ G_n$, $G_n$ $G_n\ M_n$, $M_n\ M_n\ M_n\ G_n$, $M_n\ M_n\ M_n\ G_n\ M_n$, $M_n\ G_n\ G_n\ M_n$, $G_n$ $M_n\ G_n\ G_n$, $G_n\ M_n\ M_n\ G_n$, $G_n\ M_n\ M_n\ G_n$, $G_n\ G_n\ M_n\ M_n$, $G_n$ $G_n\ M_n\ G_n\ M_n$, $G_n\ M_n\ G_n\ G_n$, $G_n\ G_n\ M_n$, $G_n\ M_n\ G_n\ M_n\ M_n$, $M_n\ G_n\ M_n\ G_n\ M_n\ G_n$, $G_n\ G_n\ M_n\ M_n\ G_n$, $G_n\ G_n\ M_n\ G_n\ M_n\ G_n$, a sequential addition or a permutation of one or more of said $G_n$ with one or more $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

8. A composite comprising a gel $G_n$ which is *formed into a composite by heat and physically interlocked* with a selected material $M_n$; said gel formed from (i) 100 parts by weight of one or more block copolymers of poly(styrene-ethylene-propylene-styrene), and from (ii) about 300 to about 1,600 parts by weight of one or more plasticizing oils with a selected amount of at least one said plasticizing oil(s) having an average molecular weight of less than about 200 and greater; said gelatinous elastomer compositions characterized by a gel gram Bloom of about 20 to about 800 gram bloom; and in combination with or without (iii) a selected amount of one or more polymers or copolymers of poly(styrene-butadiene-styrene), poly(styrene-butadiene)$_n$, poly(styrene-isoprene)$_n$, poly(styrene-ethylene-propylene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and wherein said composite formed from the combination $G_n\ M_n$, $G_n\ M_n\ G_n$, $M_n\ G_n\ M_n$, $M_n$ $G_n$ $G_n$, $G_n$ $G_n$ $M_n$, $M_n$ $M_n$ $M_n$ $G_n$, $M_n$ $M_n$ $M_n$ $G_n$ $M_n$, $M_n$ $G_n$ $G_n$ $M_n$, $G_n$ $M_n$ $G_n$ $G_n$, $G_n$ $M_n$ $M_n$ $G_n$, $G_n$ $M_n$ $M_n$ $G_n$, $G_n$ $G_n$ $M_n$ $M_n$, $G_n$ $G_n$ $M_n$ $G_n$ $M_n$, $G_n$ $M_n$ $G_n$ $G_n$, $G_n$ $G_n$ $M_n$, $G_n$ $M_n$ $G_n$ $M_n$ $M_n$, $M_n$ $G_n$ $M_n$ $G_n$ $M_n$ $G_n$ , $G_n$ $G_n$ $M_n$ $M_n$ $G_n$, $G_n$ $G_n$ $M_n$ $G_n$ $M_n$ $G_n$, a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

10. A composite comprising a gel $G_n$ *which is formed into a composite by heat and physically interlocked* with a selected material $M_n$; said gel formed from (i) 100 parts by weight of one or more block copolymers of poly(styrene-ethylene-ethylene-propylene-styrene), and from (ii) about 300 to about 1,600 parts by weight of one or more plasticizing oils with a selected amount of at least one said plasticizing oil(s) having a viscosity [of about] *greater than* 4 cSt and 40° C. [and greaer]; said gelatinous elastomer compositions characterized by a gel gram Bloom of about 20 to about 800 gram bloom; and in combination with or without one or more of (iii) a selected amount of one or more block copolymers of poly(styrene-butadiene-styrene), poly(styrene-butadiene)$_n$, poly(styrene-isoprene)$_n$, poly(styrene-ethylene-propylene)$_n$, or poly(styrene-ethylene-butylene)$_n$; a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene); a selected amount of a hydrocarbon resins including polystyrene, polypropylene, or polyethylene; a selected amount of polybutylene; a selected amount of rubbers of poly(ethylene-propylene) or poly(ethylene-butylene); a selected amount of a flame retardant; a selected amount of one or more internal and external non-adhering, non-sticking modifiers selected from amorphous silica, talc, zinc sterate, aluminum sterate, mica, and silicon dioxide; a selected amount of microspheres or aggregation of gas bubbles; wherein said selected copolymer is a linear, radial, star-shaped, branched or multiarm copolymer, wherein n is greater than one; and wherein said composite formed from the combination $G_n$ $M_n$, $G_n$ $M_n$ $G_n$, $M_n$ $G_n$ $M_n$, $M_n$ $G_n$ $G_n$, $G_n$ $G_n$ $M_n$, $M_n$ $M_n$ $M_n$ $G_n$, $M_n$ $M_n$ $M_n$ $G_n$ $M_n$, $M_n$ $G_n$ $G_n$ $M_n$, $G_n$ $M_n$ $G_n$ $G_n$, $G_n$ $M_n$ $M_n$ $G_n$, $G_n$ $M_n$ $G_n$ $G_n$, $G_n$ $M_n$ $M_n$ $G_n$, $G_n$ $M_n$ $G_n$ $M_n$, $G_n$ $M_n$ $G_n$ $M_n$ $M_n$, $M_n$ $G_n$ $M_n$ $G_n$ $M_n$ $G_n$, $M_n$ $G_n$ $M_n$ $M_n$, $G_n$ $M_n$ $G_n$ $M_n$ $G_n$ $M_n$, $G_n$, $G_n$ $G_n$ $M_n$ $M_n$ $G_n$, $G_n$ $G_n$ $M_n$ $G_n$ $M_n$ $G_n$, a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

11. A composite comprising a gel $G_n$ *which is formed into a composite by heat and physically interlocked* with a selected material $M_n$; said gel formed from (i) 100 parts by weight of one or more block copolymers of poly(styrene-ethylene-ethylene-propylene-styrene), and from (ii) about 300 to about 1,600 parts by weight of one or more plasticizing oils with a selected amount of at least one said plasticizing oil(s) having a viscosity [of about] *greater than* 4 cSt at 40° C. [and greaer]; said gelatinous elastomer compositions characterized by a gel gram Bloom of about 20 to about 800 gram bloom; and in combination with or without one or more of (iii) a selected amount of one or more block copolymers of poly(styrene-butadiene-styrene), poly(styrene-butadiene)$_n$, poly(styrene-isoprene)$_n$, poly(styrene-ethylene-propylene)$_n$, poly(ethylene-styrene); or poly(styrene-ethylene-butylene)$_n$; a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene); a selected amount of a hydrocarbon resins including polystyrene, polypropylene, or polyethylene; a selected amount of polybutylene; a selected amount of rubbers of poly(ethylene-propylene) or poly(ethylene-butylene); a selected amount of a flame retardant; a selected amount of non-adhering, non-sticking modifiers selected from amorphous silica, talc, zinc sterate, aluminum sterate, mica, and silicon dioxide; a selected amount of microspheres or aggregation of gas bubbles; wherein said selected copolymer is a linear, radial, star-shaped, branched or multiarm copolymer, wherein n is greater than one; and wherein said composite formed from the combination $G_n$ $M_n$, $G_n$ $M_n$ $G_n$, $M_n$ $G_n$ $M_n$, $M_n$ $G_n$ $G_n$, $G_n$ $G_n$ $M_n$, $M_n$ $M_n$ $M_n$ $G_n$, $M_n$ $M_n$ $M_n$ $G_n$ $M_n$, $M_n$ $G_n$ $G_n$ $M_n$, $G_n$ $M_n$ $G_n$ $G_n$, $G_n$ $M_n$ $M_n$ $G_n$, $G_n$ $M_n$ $G_n$ $G_n$, $G_n$ $M_n$ $M_n$ $G_n$, $G_n$ $M_n$ $G_n$ $M_n$, $G_n$ $M_n$ $G_n$ $M_n$ $M_n$, $M_n$ $G_n$ $M_n$ $G_n$ $M_n$ $G_n$, $M_n$ $G_n$ $G_n$, $G_n$ $G_n$ $M_n$, $G_n$ $M_n$ $G_n$ $M_n$ $M_n$, $M_n$ $G_n$ $M_n$ $G_n$ $M_n$ $G_n$ , $G_n$ $G_n$ $M_n$ $M_n$ $G_n$, $G_n$ $G_n$ $M_n$ $G_n$ $M_n$ $G_n$, a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

12. A composite comprising a gel $G_n$ *which is formed into a composite by heat and physically interlocked* with a selected material $M_n$; said gel formed from (i) 100 parts by weight of one or more block copolymers poly(styrene-ethylene-ethylene-propylene-styrene), and from (ii) about 300 to about 1,600 parts by weight of one or more plasticizing oils with a selected amount of at least one said plasticizing oil(s) having a viscosity [of about] *greater than* 4 cSt at 40° C. [and greater]; said gelatinous elastomer compositions characterized by a gel gram Bloom of about 20 to about 800 gram bloom; and in combination with or without one or more of (iii-xii): (iii) a selected amount of one or more block copolymers of poly(styrene-butadiene-styrene), poly(styrene-butadiene)$_n$, poly(styrene-isoprene)$_n$, poly(styrene-ethylene-propylene)$_n$, poly(ethylene-styrene); or poly(styrene-ethylene-butylene)$_n$; (iv) a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene); (v) a selected amount of a hydrocarbon resins including polystyrene, polypropylene, or polyethylene, or polybutylene; (vi)a selected amount of rubbers of polybutylene; (vi) a selected amount of rubbers of poly(ethylene-propylene) or poly(ethylene-butylene); (viii) a selected amount of a flame retardant; (viii) a selected amount of non-adhering, non-sticking additives comprising antiblocking agents including tetrakis [methylene 3, -(3'5'-di-tertbutyl-4"-hydroxyphenyl)propionate]methane, octadecyl 3, -(3"5"-di-tert-butyl-4"-hydroxyphenyl)propionate, distearyl-pentaerythritol-diproprionate, thiodiethylene bis-(3,5-ter-butyl-4-hydroxy)hydrocinnamate, (1,3,5-trimethyl-2,4,6-tris[3,5-di-tert-butyl-4-hydroxybenzyl]benzene), 4,4"-methylenebis(2,6-di-tert-butylphenol), additives of stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes, and silicone fluids; (ix) a selected amount of microspheres, aggregation of gas bubbles, or blowing agents; (x) one or more additives selected from the group consisting of polyisobutylene including polybutene, hydrocarbon resins including polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon, polycarbon, polyalphamethylstyrene/vinyl toluene copolymer, polystyrene, and elastomeric diblock copolymers of poly(styrene-butadiene)$_n$, poly(styrene-isoprene)$_n$, poly(styrene-ethylene-propylene)$_n$, or poly(-ethylene-butylene)$_n$, poly(styrene-butadiene)$_n$, poly(styrene-styrene)$_n$, poly(styrene-ethylene-propylene)$_n$, poly(styrene-ethylene-butylene)$_n$, poly(ethylene-propylene), poly(styrene-ethylene-butylene); (xi) one or more additives selected from the group consisting of hydrocarbon resins, butyl rubber, polyisobutylene, additional block copolymers of poly(styrene-isoprene-styrene), poly(styrene-butadiene-styrene), poly(styrene-butadiene)$_n$, poly(styrene-isoprene)$_n$, poly(styrene-ethylene-propylene)$_n$, poly(styrene-ethylene-butylene)$_n$, polystyrene, polybutylene, poly(ethylene-propylene), poly(ethylene-butylene), polypropylene, polyethylene, diblock copolymers of poly(styrene-ethylene-propylene), poly(styrene-ethylene-butylene), stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, waxes, and silicone fluids, magnetic particle materials, carbon blacks, silicon dioxide, silica, mica, talc, zinc sterate, amorphous silica, silica, silicon dioxide, aluminum sterate, fine metallic powder, metal flakes, clay, feldspar, glass microspheres, barium ferrite, wollastonite, hydrocarbon resins of polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon; wherein said selected copolymer is a linear, radial, star-shaped, branched or multi-arm copolymer, wherein n is greater than one; and wherein said composite formed from the combination: (xii) layers of $G_n M_n, G_n M_n G_n, M_n G_n M_n, M_n G_n G_n, G_n G_n M_n, M_n M_n, M_n G_n, M_n M_n M_n G_n M_n, M_n G_n G_n M_n, G_n M_n G_n G_n, G_n M_n M_n G_n, G_n M_n M_n G_n, G_n G_n M_n M_n, G_n G_n M_n G_n M_n, G_n M_n G_n G_n, G_n G_n M_n, G_n M_n G_n M_n M_n, M_n G_n M_n G_n, M_n G_n, G_n G_n M_n M_n G_n,$ and $G_n G_n M_n G_n M_n G_n,$ a sequential addition or a permutation of one or more of said $G_n$ with $M_n$; wherein when n is a subscript of M, n is the same or different selected from the group consisting of foam; plastic, fabric, glass, ceramics, synthetic resin, or synthetic fibers; and wherein n is a subscript of G, n denotes the same or a different gel rigidity.

14. A composite comprising a gel $G_n$ [and] *which is formed into a composite by heat and physically interlocked with a selected material $M_n$,* formed from (i) 100 parts by weight of one or more block copolymers with a polyethylene midblock segment of the formula poly(styrene-ethylene-ethylene-propylene-styrene) exhibiting a measurable amount of polyethylene crystallinity characterized by stress induced crystallinity not exhibited by gels having corresponding rigidity made from a poly(styrene-ethylene-butylene-styrene) or poly(styrene-ethylene-propylene-styrene) block copolymers wherein said block copolymer is a high viscosity copolymer having a viscosity value at 5 weight percent solution in toluene at 30° C. of about 90 cps and higher which corresponds to a viscosity at 10 weight percent of about 5800 cps and higher which corresponds to a viscosity at 20 weight percent solids solution in toluene at 25° C. of at about 80,000 cps and higher, and from (ii) about 300 to about 1,600 parts by weight of one or more plasticizing oils with a selected amount of at least one said plasticizing oil(s) having a viscosity [of about] *greater than* 4 cSt at 40° C. [and greater]; said gelatinous elastomer compositions characterized by a gel gram Bloom of about 20 to about 800 gram bloom; and in combination with or without (iii) a selected amount of one or more block copolymers of poly-(styrene-butadiene-styrene), poly(styrene-butadiene)$_n$, poly-(styrene-isoprene)$_n$, poly(styrene-ethylene-propylene)$_n$, or poly(styrene-ethylene-butylene)$_n$; a selected amount of one or more diblock copolymers of poly(styrene-butadiene)$_n$, poly(styrene-isoprene)$_n$, poly(styrene-ethylene-propylene)$_n$, or poly(styrene-ethylene-butylene)$_n$, poly(styrene-ethylene-propylene), poly(styrene-ethylene-butylene); a selected amount of a hydrocarbon resins including polystyrene, polypropylene, or polyethylene; a selected amount of polybutylene; a selected amount of rubbers of poly(ethylene-propylene) or poly(ethylene-butylene); a selected amount of a flame retardant; a selected amount of non-adhering, non-sticking modifiers; a selected amount of microspheres or aggregation of gas bubbles; wherein said selected copolymer is a linear, radial, star-shaped, branched or multiarm copolymer, wherein n is greater than one; and wherein said composite formed from the combination $G_n M_n, G_n M_n G_n, M_n G_n M_n, M_n G_n G_n, G_n G_n M_n, M_n M_n M_n G_n, M_n M_n M_n G_n M_n, M_n G_n G_n M_n, G_n M_n G_n G_n, G_n M_n M_n G_n, G_n M_n M_n G_n, G_n G_n M_n M_n, G_n G_n M_n G_n M_n, G_n M_n G_n G_n, G_n G_n M_n, G_n M_n G_n M_n M_n, M_n G_n M_n G_n M_n G_n, G_n G_n M_n M_n G_n, G_n G_n M_n G_n M_n G_n,$ a sequential addition or a permutation of one or more of said $G_n$ with $M_n$; wherein when n is a subscript of M, n is the same or different selected from the group consisting of foam, plastic, fabric, glass, ceramics, synthetic resin, or synthetic fibers; and wherein when n is a subscript of G, n denotes the same or a different gel rigidity.

*18. A composite gel liner comprising a gel $G_n$ which is formed into a composite by heat and physically interlocked with a selected material $M_n$; said gel formed from (i) 100 parts by weight of one or more block copolymers of poly(styrene-ethylene-ethylene-propylene-styrene), and from (ii) about 300 to about 1,600 parts by weight of one or more plasticizing oils with a selected amount of at least one said plasticizing oil(s) having an average molecular weight of less than about 200 and greater; said gelatinous elastomer compositions characterized by a gel gram Bloom of about 20 to about 800 gram bloom; and in combination with or without (iii) a selected amount of one or more polymers or copolymers of poly(styrene-butadiene-styrene), poly(styrene-butadiene)$_n$, poly(styrene-isoprene)$_n$, poly(styrene-ethylene-propylene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and wherein said composite formed from the combination $G_n M_n, G_n M_n G_n, M_n G_n M_n, M_n G_n G_n, G_n G_n M_n, M_n M_n M_n G_n, M_n M_n M_n G_n M_n, M_n G_n G_n M_n, G_n M_n G_n G_n, G_n M_n M_n G_n, G_n M_n M_n G_n, G_n G_n M_n M_n, G_n G_n M_n G_n M_n, G_n M_n G_n G_n, G_n G_n M_n, G_n M_n G_n M_n M_n, M_n M_n M_n G_n M_n G_n M_n G_n, G_n G_n M_n M_n G_n, G_n G_n M_n G_n M_n G_n,$ a sequential addition or a permutation of one or more of said $G_n$ with $M_n$; wherein when n is a subscript of M, n is the same or different selected from the group consisting of foam, plastic, fabric, ceramics, synthetic resin, or syn-*

*thetic fibers; and wherein when n is a subscript of G, n denotes the same or a different gel rigidity.*

*19. A composite gel liner comprising a gel $G_n$ which is formed into a composite by heat and physically interlocked with a selected material $M_n$; said gel formed from (i) 100 parts by weight of one or more block copolymers of poly(styrene-ethylene-ethylene-propylene-styrene), and from (ii) about 300 to about 1,600 parts by weight of one or more plasticizing oils with a selected amount of at least one said plasticizing oil(s) having an average molecular weight of less than about 200 and greater; said gelatinous elastomer compositions characterized by a gel gram Bloom of about 20 to about 800 gram bloom: wherein n is greater than one: and wherein said composite formed from the combination $G_n M_n$, $G_n M_n G_n$, $M_n G_n M_n$, $M_n M_n M_n G_n$, $M_n M_n M_n G_n M_n$, $M_n$ $G_n G_n M_n$, $G_n M_n G_n G_n$, $G_n M_n M_n G_n$, a sequential addition or a permutation of one or more of said $G_n$ with $M_n$; wherein when n is a subscript of M, n is the same or different selected from the group consisting of foam, plastic, fabric, synthetic resin, or synthetic fibers; and wherein when n is a subscript of G, n denotes the same or a different gel rigidity.*

*20. A composite gel liner comprising a gel $G_n$ which is formed into a composite by heat and physically interlocked with a selected material $M_n$; said gel formed from (i) 100 parts by weight of one or more block copolymers of poly(styrene-ethylene-ethylene-propylene-styrene), and from (ii) about 300 to about 1,600 parts by weight of one or more plasticizing oils with a selected amount of at least one said plasticizing oil(s) having an average molecular weight of less than about 200 and greater; said gelatinous elastomer compositions characterized by a gel gram Bloom of about 20 to about 800 gram bloom; wherein said selected copolymer is a linear, radial, star-shaped, branched or multiarm copolymer, wherein n is greater than one; and wherein said composite formed from the combination $G_n M_n$, $G_n M_n G_n$, $M_n G_n M_n$, a sequential addition or a permutation of one or more of said $G_n$ with $M_n$; wherein when n is a subscript of M, n is the same or different selected from the group consisting of foam, plastic or fabric; and wherein when n is a subscript of G, n denotes the same or a different gel rigidity.*

\* \* \* \* \*